(12) United States Patent
Hauptmann et al.

(10) Patent No.: US 6,294,352 B1
(45) Date of Patent: Sep. 25, 2001

(54) TNF RECEPTORS, TNF BINDING PROTEINS AND DNAS CODING FOR THEM

(75) Inventors: Rudolf Hauptmann, Ebreichsdorf; Adolf Himmler, Vienna; Ingrid Maurer-Fogy, A-1238 Vienna; Christian Stratowa, Vienna, all of (AT)

(73) Assignee: Amgen Inc.

( * ) Notice: Subject to any disclaimer, the term of this patent is extended or adjusted under 35 U.S.C. 154(b) by 0 days.

(21) Appl. No.: 08/383,676

(22) Filed: Feb. 1, 1995

Related U.S. Application Data

(63) Continuation of application No. 08/153,287, filed on Nov. 17, 1993, now abandoned, which is a continuation of application No. 07/821,750, filed on Jan. 2, 1992, now abandoned, which is a division of application No. 07/511,430, filed on Apr. 30, 1990, now abandoned.

(30) Foreign Application Priority Data

| Apr. 21, 1989 | (DE) | 93 13 101 |
| Jun. 21, 1989 | (DE) | 39 20 282 |
| Apr. 6, 1990 | (EP) | 90106624 |

(51) Int. Cl.[7] ........................................ C12N 15/00

(52) U.S. Cl. .................. 435/69.1; 435/320.1; 435/69.5; 435/252.3; 536/23.5

(58) Field of Search .................... 530/351; 435/69.5, 435/69.8, 240.1, 320.1, 252.3, 69.1; 536/23.51

(56) References Cited

U.S. PATENT DOCUMENTS

| 4,289,690 | * | 9/1981 | Pestka et al. | 260/112 |
| 4,560,649 | * | 12/1985 | Saxena et al. | 435/7 |
| 4,578,335 | * | 3/1986 | Urdal et al. | 435/65 |
| 4,609,546 | * | 9/1986 | Hiratani | 424/83 |
| 4,675,285 | * | 6/1987 | Clark et al. | 435/6 |
| 4,789,658 | * | 12/1988 | Yoshimoto et al. | 514/12 |
| 4,902,502 | * | 2/1990 | Nitecki et al. | 424/83 |
| 4,904,584 | * | 2/1990 | Shaw et al. | 435/69.4 |
| 4,931,544 | * | 6/1990 | Katre et al. | 530/351 |
| 4,935,233 | * | 6/1990 | Bell et al. | 424/85.5 |
| 4,966,888 | * | 10/1990 | Saxena et al. | 514/2 |
| 5,089,261 | * | 2/1992 | Nitecki et al. | 424/85.2 |
| 5,116,964 | * | 5/1992 | Capon et al. | 536/27 |
| 5,136,021 | * | 8/1992 | Dembinski et al. | 530/350 |
| 5,153,265 | * | 10/1992 | Shadle et al. | 525/54.1 |
| 5,162,430 | * | 11/1992 | Rhee et al. | 525/54.1 |
| 5,214,131 | * | 5/1993 | Sano et al. | 530/345 |
| 5,252,714 | * | 10/1993 | Harris et al. | 530/391.9 |
| 5,344,915 | * | 9/1994 | LeMaire et al. | 530/350 |
| 5,359,037 | * | 10/1994 | Wallach et al. | 530/388.22 |
| 5,382,657 | * | 1/1995 | Karasiewicz et al. | 530/351 |
| 5,395,760 | * | 3/1995 | Smith et al. | 435/240.1 |
| 5,478,925 | * | 12/1995 | Wallach et al. | 530/351 |
| 5,512,544 | * | 4/1996 | Wallach et al. | 514/12 |
| 5,605,690 | * | 2/1997 | Jacobs et al. | |
| 5,610,279 | * | 3/1997 | Brockhaus et al. | 530/387.3 |
| 5,633,145 | * | 5/1997 | Feldmann et al. | |
| 5,695,953 | * | 12/1997 | Wallach et al. | |
| 5,712,155 | * | 1/1998 | Smith et al. | |
| 5,808,029 | * | 9/1998 | Brockhaus et al. | |
| 5,811,261 | * | 9/1998 | Wallach et al. | |
| 5,843,791 | * | 12/1998 | Hauptmann et al. | |
| 5,863,786 | * | 1/1999 | Feldmann et al. | |

FOREIGN PATENT DOCUMENTS

| 3913101 | * | 4/1989 | (DE) . |
| 03 920 282 | * | 6/1989 | (DE) . |
| 0 154 316 A2 | * | 9/1985 | (EP) . |
| 0162699 | * | 11/1985 | (EP) . |
| 0 225 579 A3 | * | 6/1987 | (EP) . |
| 0 247 860 A2 | * | 12/1987 | (EP) . |
| 0 259 863 A2 | * | 3/1988 | (EP) . |
| 0308378 | * | 3/1989 | (EP) . |
| 0 154 316 B1 | * | 9/1989 | (EP) . |
| 0 334 165 A2 | * | 9/1989 | (EP) . |
| 0 393 438 A2 | * | 10/1990 | (EP) . |
| 0 398 327 A1 | * | 11/1990 | (EP) . |
| 412486 | * | 2/1991 | (EP) . |
| 0 418 014 A1 | * | 3/1991 | (EP) . |
| 0 422 339 | * | 4/1991 | (EP) . |
| 0 512 528 A2 | * | 11/1992 | (EP) . |
| 0 526 905 A2 | * | 2/1993 | (EP) . |
| 2218101 | * | 11/1989 | (GB) . |
| 2 246 569 | * | 2/1992 | (GB) . |
| WO 91/03553 | * | 3/1991 | (WO) . |
| WO9201002 | * | 1/1992 | (WO) . |
| WO 92/01474 | * | 2/1992 | (WO) . |
| WO 92/07076 | * | 4/1992 | (WO) . |
| WO 92/13095 | * | 8/1992 | (WO) . |
| WO 92/15682 | * | 9/1992 | (WO) . |
| WO 92/16221 | * | 10/1992 | (WO) . |
| WO 94/06476 | * | 3/1994 | (WO) . |

OTHER PUBLICATIONS

Leung et al. 1987 Nature 330:537–543.*

(List continued on next page.)

*Primary Examiner*—Gabnette D. Draper
(74) *Attorney, Agent, or Firm*—McDonnell Boehnen Hulbert & Berghoff

(57) ABSTRACT

DNA sequences coding for a TNF-binding protein and for the TNF receptor of which this protein constitutes the soluble domain. The DNA sequence can be used for preparing recombinant DNA molecules in order to produce TNF-binding protein and TNF receptor. Recombinant TNF-binding protein is used in pharmaceutical preparations for treating indications in which TNF has a harmful effect. With the aid of the TNF receptor or fragments thereof or with the aid of suitable host organisms transformed with recombinant DNA molecules containing the DNA which codes for the TNF receptor or fragments or modifications thereof, it is possible to investigate substances for their interaction with the TNF receptor and/or for their effect on the biological activity of TNF.

63 Claims, 22 Drawing Sheets

OTHER PUBLICATIONS

Figure 2:
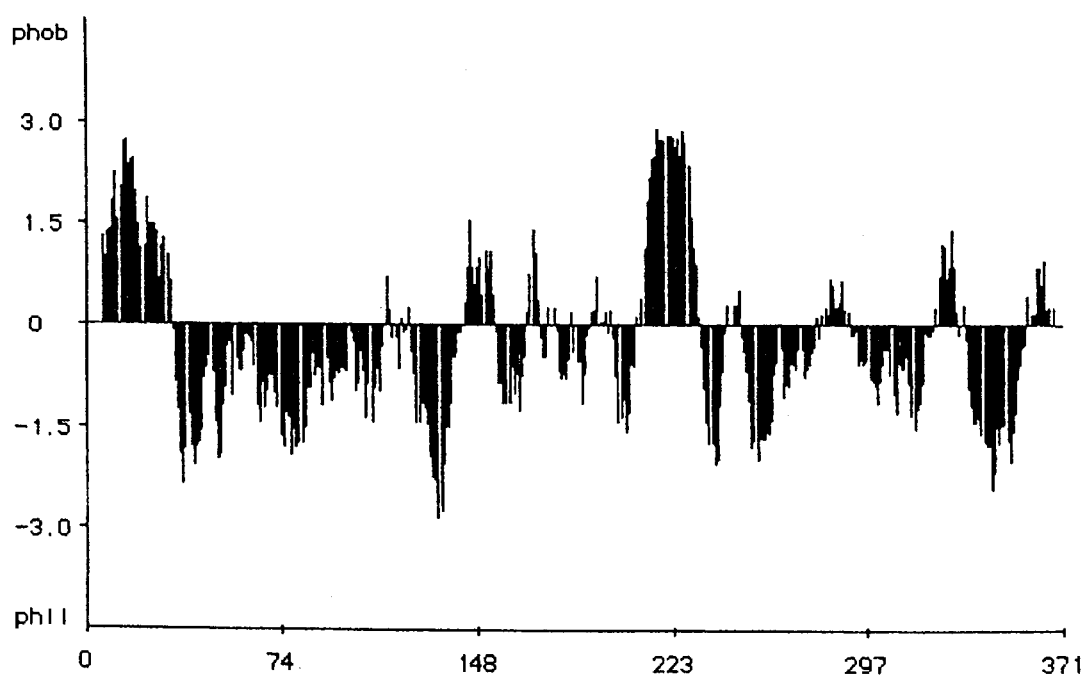

Socher et al 1987 PNAS 84:8829–8833.*
Aggarwal, B. et al., *Nature* 318:665–667 (1985).*
Brockhaus, M. et al., *Proc. Natl. Acad. Sci. USA* 87:3127–3131 (1990).*
Creasey, A. et al., *Proc. Natl. Acad. Sci. USA* 84:3293–3297 (1987).*
Engelmann, H. et al., *J. Biol. Chem.* 264:11974–11980 (1989).*
Engelmann, H. et al., *J. Biol. Chem.* 265(3) :1531–1536, (1990).*
Espevik, T. et al., *J. Exp. Med.* 171:415–426 (1990).*
Frohman, M. et al., *Proc. Natl. Acad. Sci. USA* 85:8998–9002 (1988).*
Gray P.W. et al. *PNAS* 87 (19):7380–7384 (1990).*
Hass et al., *J. Biol. Chem.* 260(22):12214–12218 (1985).*
Himmler A. et al., *DNA and Cell Biology* 9(10):705–715 (1990).*
Hohmann, H.P. et al., *J. Biol. Chem.* 264:14927–14934 (1989).*
Kull et al., *PNAS* 82:5756–5760 (1985).*
Loetscher, H. et al., *Cell* 61:351–359 (1990).*
Olsson, I. et al., *Eur. J. Haematol.* 42:270–275 (1989).*
Peetre, C. et al., *Eur. J. Haematol* 41:414–419 (1988).*
Schall, T.J. et al., *Cell* 61:361–370 (1990).*
Scheurich et al., *Int. J. Cancer* 38:127–133 (1986).*
Seckinger, P. et al., *J. Biol. Chem.* 264:11966–11973 (1989).*
Smith et al., *Science* 248:1019–1023 (1990).*
Stauber, G. et al., *J. Biol. Chem.* 263(35):19098–19104 (1988).*
Stauber, G.B. et al.,*J. Biol. Chem.* 264:3573–3576 (1989).*
European Search Report for the corresponding European Application No. EP90106624.1 corresponding to U.S. application No. 07/511,430.*
Anderson et al., "Quantative Filter Hybridisation," *Nucleic Acid Hybridization: A Practical Approach*, Hawes et al. (ed.), pp. 73–111 (1985).*
Baglioni et al., "Binding of Human Tumor Necrosis Factor to High Affinity Receptors on HeLa and Lymphoblastoid Cells Sensitive to Growth Inhibition," *J. Biol. Chem.* 260(25):13395–13397 (1985).*
Bakouche et al., "Plasma Membrane–Associated Tumor Necrosis Factor, A Non–Integral Membrane Protein Possibly Bound to Its Own Receptor," *J. Immunol.* 140:1142–1147 (1988).*
Beutler et al., "Passive Immunization against Cachetin/Tumor Necrosis Factor Protects Mice from Lethal Effect of Endotoxin," *Science* 229:869–871 (1985).*
Bowie et al., "Deciphering the Message in Protein Sequences: Tolerance to Amino Acid Substitutions," *Science*, 247:1306–1310 (1990).*
Brennan et al., Lancet, vol. 2 (8657), pp. 244–247 (1989).*
Capaldi et al., "Changes in Order of Migration of Polypeptides in Complex III and Cytochrome c Oxidase under Different Conditions of SDS Polyacrylamide Gel Electrophoresis," *Biochem. & Biophys. Res. Commun.* 74(2):425–433 (1977).*
Carlino et al., "Use of a Sensitive Receptor Binding Assay to Discriminate Between Full–Length and Truncated Human Recombinant TNF Proteins", *J. Biol. Chem.* 262(3):958–961 (1987).*
Colletti et al., "The Production of Tumor Necrosis Factor Alpha and the Development of a Pulmonary Capillary Injury Following Hepatic Ischemia/Reperfusion," *Transplantation* 49(2):268–272 (1990).*
Dayer et al., "Purification and Characterization of Human Tumor Necrosis Factor α Inhibitor," *Chemical Abstracts* 113(38760n):454 (1990).*
Dembic et al., "Two Human TNF Receptors Have Similar Extracellular, But Distinct Intracellular, Domain Sequences," *Cytokine* 2(4):231–237 (1990).*
Engelman et al., "Antibodies to s Soluble Form of a Tumor Necrosis Factor (TNF) Receptor Have TNF–Like Activity," *J. Biol. Chem.* 265(24):14497–14504 (1990).*
Evans et al., "The Steroid and Thyroid Hormone Receptor Superfamily," *Science* 240:889–895 (1988).*
Goodson et al., "Site–Directed Pegylation of Recombinant Interleukin–2 At Its Glycosylation Site," *BioTechnology* 8:343–346 (1990).*
Goodwin et al., "Molecular Cloning and Expression of the Type 1 and Type 2 Murine Receptors for Tumor Necrosis Factor," *Molecular and Cell Biology* 11(6):3020–3026 (1991).*
Grizzard et al., "Affinity–Labeled Somatomedin–C Receptors and Binding Proteins From the Human Fetus," *J. Clin. Endocrinol. & Metab.* 58(3):535–543 (1984).*
Hale et al., "Cytokines and Their Receptors: From Clonal to Clinical Investigation, Demonstration of In Vitro and In Vivo Efficacy of Two Biologically Active Human Soluble TNF Receptors Expressed in *E. Coli,*" *J. Cell Biochem. Suppl..* 15F:113 (1991).*
Hatakeyama et al., "Interleukin–2 Receptor β Chain Gene: Generation of Three Receptor Forms by Cloned Human α and β Chain cDNA's," *Science* 244:551–556 (1989).*
Hauser et al., "Cytokine Accumulations in CSF of Multiple Sclerosis Patients: Frequent Detection of Interleukin–1 and Tumor Necrosis Factor but not Interleukin–6," *Neurology* 40:1735–1739 (1990).*
Heller et al., "Complementary DNA Cloning of a Receptor for Tumor Necrosis Factor and Demonstration of a Shed Form of the Receptor," *Proc. Natl. Acad. Sci. USA* 87:6151–6155 (1990).*
Hofman et al., "Tumor Necrosis Factor Identified in Multiple Sclerosis Brain," *J. Exp. Med.* 170:607–612 (1989).*
Israel et al., "Binding of Human TNF–alpha to High–Affinity Cell Surface Receptors: Effect of IFN," *Immunol. Lett.* 12:217–224 (1986).*
Kasukabe et al., "Purification of a Novel Growth Inhibitory Factor for Partially Differentiated Myeloid Leukemic Cells," *J. Biol. Chem.* 263(11):5431–5435 (1988).*
Kohno et al., "A Second Tumor Necrosis Factor Receptor Gene Product Can Shed a Naturally Occurring Tumor Necrosis Factor Inhibitor," *Proc. Natl. Acad. Sci. USA* 87:8331–8335 (1990).*
Lantz et al., "Characterization In Vitro of a Human Tumor Necrosis Factor–Binding Protein," *J. Clin. Invest.* 86(5):1396–1402 (1990).*
Le et al., "Tumor Necrosis Factor and Interleukin 1: Cytokines with Multiple Overlapping Biological Activities," *Lab Investigation* 56(3):234–248 (1987).*
Lee et al., "Generation of cDNA Probes Directed by Amino Acid Sequence: Cloning of Urate Oxidase," *Science* 239:1288–1291 (1988).*

Lehmann et al., "Demonstration of Membrane Receptors for Human Natural and Recombinant $^{125}$I–Labeled Tumor Necrosis Factor on HeLa Cell Clones and Their Role in Tumor Cell Sensitivity," *Eur. J. Biochem.* 158:1–5 (1986).*

Liao et al., "Characterization of a Human Interleukin 1 Inhibitor," *J. Immunol.* 134(6):3882–3886 (1985).*

Liao et al., "Identification of a Specific Interleukin 1 Inhibitor in the Urine of Febrile Patients," *J. Exp. Med.* 159:126–136 (1984).*

Liblau et al., "Tumor Necrosis Factor–α and Disease Progression in Multiple Sclerosis," *New Engl. J. Med.* 326(4):272–273 (1992).*

Lindvall et al., "Modulation of the Constitutive Gene Expression of the 55 KD Tumor Necrosis Factor Receptor in Hematopoietic Cells," *Biochem. & Biophys. Res. Comm.* 172(2)557–563 (1990).*

Loetscher et al., "Recombinant 55–kDa Tumor Necrosis Factor (TNF) Receptor," *J. Biol. Chem.* 266(27):18324–18329 (1991).*

March et al., "Cloning, Sequence and Expression of Two Distinct Human Interleukin–1 Complementary DNAs," *Nature* 315:641–647 (1985).*

Neda, Hiroshi, "Analysis of the Tumor Necrosis Factor (TNF) Receptor of Various Tumor Cells," *Tumor Necrosis Factor, (TNF) Receptor* 56(2):305–317 (1987). (Abstract in English).*

Nexo et al., "Lectin–Agarose Immobilization, a New Method for Detecting Soluble Membrane Receptors," *J. Biol. Chem.* 254(18):8740–8743 (1979).*

Nophar et al., "Soluble forms of tumor necrosis factor receptors (TNF-Rs). The cDNA for the type I TNF-R, cloned using amino acid sequence data of its soluble form, encodes both the cell surface and a soluble form of the receptor," *The EMBO J.* 9(10):3269–3278 (1990).*

Novick et al., "Soluble Cytokine Receptors are Present in Normal Human Urine," *J. Exp. Med.* 170:1409–1414 (1989).*

Novick et al., "Soluble Cytokine Receptors are Present in Normal Human Urine," *The Physiological and Pathological Effects of Cytokines*, pp. 413–421 (1990).*

Novick et al., "Purification of Soluble Cytokine Receptors from Normal Human Urine by Ligand–Affinity and Immunoaffinity Chromatography," *J. Chromatog.* 510:331–337 (1990).*

Peppel et al., "A Tumor Necrosis Factor (TNF) Receptor–IgG Heavy Chain Chimeric Protein as a Bivalent Antagonist of TNF Activity," *J. Exp. Med.* 174:1483–1489 (1991).*

Piguet et al., "Tumor Necrosis Factor/Cachectin Plays a Key Role in Bleomycin–Induced Pneumopathy and Fibrosis," *J. Exp. Med.* 170:655–663 (1989).*

Powell et al., "Lymphotoxin and Tumor Necrosis Factor–alpha Production by Myelin basic Protein–Specific T Cell Clones Correlates With Encephalitogenicity," *International Immunology* 2(6):539–544 (1990).*

Rhein et al., "Another Sepsis Drug Down—Immunex[1] TNF Receptor," Biotechnology *Newswatch*, p. 1,3(Monday, Oct. 4, 1993).*

Ruddle et al., "An Antibody to Lymphotoxin and Tumor Necrosis Factor Prevents Transfer of Experimental Allergic Encephalomyelitis," *J. Exp. Med.* 172:1193–1200 (1990).*

Seckinger et al., "A Human Inhibitor of Tumor Necrosis Factor Alpha," *J. Exp. Med.* 167:1511–1516 (1988).*

Seckinger et al., "A Urine Inhibitor of Interleukin 1 Activity Affects Both Interleukin 1 α and 1 β But Not Tumor Necrosis Factor α," *J. Immunol.* 139(5):1541–1545 (1987).*

Seckinger et al., "Characterization of a Tumor Necrosis Factor α (TNF–α) Inhibitor: Evidence of Immunological Cross–Reactivity with the TNF Receptor," *Proc. Natl. Acad. Sci. USA* 87:5188–5192 (1990).*

Seckinger et al., "A Urine Inhibitor of Interleukin 1 Activity That Blocks Ligand Binding," *J. Immunol.* 139(5):1546–1549 (1987).*

Seckinger et la., "Purification and Biologic Characterization of a Specific Tumor Necrosis Factor α Inhibitor," *J. Biol. Chem.* 264(20):11966–11973 (1989).*

Selmaj et al., "Proliferation of Astrocytes In Vitro In Response to Cytokines: A Primary Role for Tumor Necrosis Factor," *J. Immunol.* 144(1):129–135 (1990).*

Selmaj et al., "Tumor Necrosis Factor Mediates Myelin and Oligodendrocyte Damage In Vitro," *Annals of Neurology* 23(4):339–346 (1988).*

Smith et al., "Species Specificity of Human and Murine Tumor Necrosis Factor," *J. Biol. Chem.* 261(32):14871–14874 (1986).*

Spinas et al., "Induction of Plasma Inhibitors of Interleukin 1 and TNF–Alpha Activity by Endotoxin Administration to Normal Humans," *Am. J. Physiol.* 259:R993–R997 (1990).*

Suffys et al., "Involvement of a Serine Protease in Tumour–Necrosis–Factor–Mediated Cytotoxicity," *Eur. J. Biochem.* 178:257–265 (1988).*

Suggs et al., "Use of Synthetic Oligonucleotides as Hybridization Probes: Isolation of Cloned cDNA Sequences for Human β2–Microglobulin," *Proc. Natl. Acad. Sci. USA* 78(11):6613–6617 (1981).*

The Cytokine Factsbook, Callard (ed.), Academic Press Inc., San Diego, CA., pp. 244–246 (1994).*

Tracey et al., "Anti–Cachectin/TNF Monoclonal Antibodies Prevent Septic Shock During Lethal Bacteraemia," *Nature* 330:662–664 (1987).*

Tracey et al., "Cachectin/Tumor Necrosis Factor Induces Cachexia, Anemia, and Inflammation," *J. Exp. Med.* 167:1211–1227 (1988).*

Tracey et al., "Metabolic Effects of Cachectin/Tumor Necrosis Factor Are Modified by Site of Production," *J. Clin. Invest.* 86:2014–2024 (1990).*

Tracey et al., "Physiological responses to cachectin," *Tumor necrosis factor and related cytotoxins.* Wiley, Chichester (Ciba Foundation Symposium 131), pp. 88–108 (1987).*

Tsujimoto et al., "Characterization and Affinity Crosslinking of Receptors for Tumor Necrosis Factor on Human Cells," *Archives of Biochem. & Biophys.* 249(2):563–568 (1986).*

Unglaub et al., "Downregulation of Tumor Necrosis Factor (TNF) Sensitivity Via Modulation of TNF Binding Capacity by Protein Kinase C Activators," *J. Exp. Med.* 166:1788–1797 (1987).*

Vilcek et al., "Tumor Necrosis Factor: Receptor Binding and Mitogenic Action in Fibroblasts," *J. Cell. Physio. Supplement* 5:57–61 (1987).*

Vitt et al., "Biological and Structural Characterization of the Tumor Necrosis Factor Receptor on Multiple Cell Types: Relationship to Function," Fed. Proc. 78th Annual Meeting of the American Society of Biological Chemists 46(6):2117 (1987).*

Wallach et al., "Mechanisms Which Take Part in Regulation of the Response to Tumor Necrosis Factor," *Lymphokine Research* 8(3):359–363 (1989).*

Wallach, David, "Preparations of Lymphotoxin Induce Resistance to Their Own Cytotoxic Effect," *J. Immunol.* 132(5):2464–2469 (1984).*

Wallach et al., "Regulation of the Response to Tumor Necrosis Factor," Bonavida, Gifford, Kirchner, Old (eds), Tumor Necrosis Factor/Cachectin and Related Cytokines Int. Conf. Tumor Necrosis Factor and Related Cytotoxins, Heidelberg 1987, pp. 134–147 (1988).*

Walsh et al., "Isolation and Purification of ILS, an Interleukin 1 Inhibitor Produced by Human Gingival Epithelial Cells," *Clin. Exp. Immunol.* 68:366–374 (1987).*

Weber et al., "Production of an Epidermal Growth Factor Receptor–Related Protein," *Science* 224:294–297 (1984).*

Yoshie et al., "Binding and Crosslinking of $^{125}$I–Labeled Recombinant Human Tumor Necrosis Factor to Cell Surface Receptors," *J. Biochem.* 100:531–541 (1986).*

Zeigler, Elizabeth J., "Tumor Necrosis Factor in Humans," *New Engl. J. Med.* 318(23):1533–1535 (1988).*

Shi muzu et al., "Three Human Transforming Genes Are Related to the Viral ras Oncogenes, " *Proc. Natl. Acad. Sci. U.S.A.* 80:2112–16 (1983).

* cited by examiner

FIG. 1A

```
                                    GAATTCTCTGGACTGAGGCTCCAGTTCTGGCCTTTGGGG
TTCAAGATCACTGGGACCAGGCCGTGATCTCTATGCCCGAGTCTCAACCCTCAACTGTC
ACCCCAAGGCACTTGGGACGTCCTGGACAGACCGAGTCCCGGGAAGCCCCAGCACTGCC
                                                   ***
GCTGCCACACTGCCCTGAGCCCAAATGGGGGAGTGAGAGGCCA TAG CTG TCT GGC
```

| | S1 | | | S5 | | | | | S10 | | | | S15 | |
|---|---|---|---|---|---|---|---|---|---|---|---|---|---|---|
| | Met | Gly | Leu | Ser | Thr | Val | Pro | Asp | Leu | Leu | Leu | Pro | Leu | Val | Leu |
| | ATG | GGC | CTC | TCC | ACC | GTG | CCT | GAC | CTG | CTG | CTG | CCA | CTG | GTG | CTC |
| | 216 | | | 225 | | | 234 | | | 243 | | | 252 | | |

| | | | | S20 | | | | | S25 | | | | S29 | 1 |
|---|---|---|---|---|---|---|---|---|---|---|---|---|---|---|
| Leu | Glu | Leu | Leu | Val | Gly | Ile | Tyr | Pro | Ser | Gly | Val | Ile | Gly | Leu |
| CTG | GAG | CTG | TTG | GTG | GGA | ATA | TAC | CCC | TCA | GGG | GTT | ATT | GGA | CTG |
| 261 | | | 270 | | | 279 | | | 288 | | | 297 | | |

| | | 5 | | | | 10 | | | | 15 | |
|---|---|---|---|---|---|---|---|---|---|---|---|
| Val | Pro | His | Leu | Gly | Asp | Arg | Glu | Lys | Arg | Asp | Ser | Val | Cys | Pro |
| GTC | CCT | CAC | CTA | GGG | GAC | AGG | GAG | AAG | AGA | GAT | AGT | GTG | TGT | CCC |
| 306 | | | 315 | | | 324 | | | 333 | | | 342 | | |

| | | 20 | | | | 25 | | | | 30 | |
|---|---|---|---|---|---|---|---|---|---|---|---|
| Gln | Gly | Lys | Tyr | Ile | His | Pro | Gln | Asn | Asn | Ser | Ile | Cys | Cys | Thr |
| CAA | GGA | AAA | TAT | ATC | CAC | CCT | CAA | AAT | AAT | TCG | ATT | TGC | TGT | ACC |
| 351 | | | 360 | | | 369 | | | 378 | | | 387 | | |

| | | 35 | | | | 40 | | | | 45 | |
|---|---|---|---|---|---|---|---|---|---|---|---|
| Lys | Cys | His | Lys | Gly | Thr | Tyr | Leu | Tyr | Asn | Asp | Cys | Pro | Gly | Pro |
| AAG | TGC | CAC | AAA | GGA | ACC | TAC | TTG | TAC | AAT | GAC | TGT | CCA | GGC | CCG |
| 396 | | | 405 | | | 414 | | | 423 | | | 432 | | |

| | | 50 | | | | 55 | | | | 60 | |
|---|---|---|---|---|---|---|---|---|---|---|---|
| Gly | Gln | Asp | Thr | Asp | Cys | Arg | Glu | Cys | Glu | Ser | Gly | Ser | Phe | Thr |
| GGG | CAG | GAT | ACG | GAC | TGC | AGG | GAG | TGT | GAG | AGC | GGC | TCC | TTC | ACC |
| 441 | | | 450 | | | 459 | | | 468 | | | 477 | | |

| | | 65 | | | | 70 | | | | 75 | |
|---|---|---|---|---|---|---|---|---|---|---|---|
| Ala | Ser | Glu | Asn | His | Leu | Arg | His | Cys | Leu | Ser | Cys | Ser | Lys | Cys |
| GCT | TCA | GAA | AAC | CAC | CTC | AGA | CAC | TGC | CTC | AGC | TGC | TCC | AAA | TGC |
| 486 | | | 495 | | | 504 | | | 513 | | | 522 | | |

| | | 80 | | | | 85 | | | | 90 | |
|---|---|---|---|---|---|---|---|---|---|---|---|
| Arg | Lys | Glu | Met | Gly | Gln | Val | Glu | Ile | Ser | Ser | Cys | Thr | Val | Asp |
| CGA | AAG | GAA | ATG | GGT | CAG | GTG | GAG | ATC | TCT | TCT | TGC | ACA | GTG | GAC |
| 531 | | | 540 | | | 549 | | | 558 | | | 567 | | |

FIG. 1B

```
            95                         100                        105
Arg Asp Thr Val Cys Gly Cys Arg Lys Asn Gln Tyr Arg His Tyr
CGG GAC ACC GTG TGT GGC TGC AGG AAG AAC CAG TAC CGG CAT TAT
576         585         594         603         612

110                        115                        120
Trp Ser Glu Asn Leu Phe Gln Cys Phe Asn Cys Ser Leu Cys Leu
TGG AGT GAA AAC CTT TTC CAG TGC TTC AAT TGC AGC CTC TGC CTC
621         630         639         648         657

125                        130                        135
Asn Gly Thr Val His Leu Ser Cys Gln Glu Lys Gln Asn Thr Val
AAT GGG ACC GTG CAC CTC TCC TGC CAG GAG AAA CAG AAC ACC GTG
666         675         684         693         702

140                        145                        150
Cys Thr Cys His Ala Gly Phe Phe Leu Arg Glu Asn Glu Cys Val
TGC ACC TGC CAT GCA GGT TTC TTT CTA AGA GAA AAC GAG TGT GTC
711         720         729         738         747

155                        160                        165
Ser Cys Ser Asn Cys Lys Lys Ser Leu Glu Cys Thr Lys Leu Cys
TCC TGT AGT AAC TGT AAG AAA AGC CTG GAG TGC ACG AAG TTG TGC
756         765         774         783         792

170                        175                        180
Leu Pro Gln Ile Glu Asn Val Lys Gly Thr Glu Asp Ser Gly Thr
CTA CCC CAG ATT GAG AAT GTT AAG GGC ACT GAG GAC TCA GGC ACC
801         810         819         828         837

185                        190                        195
Thr Val Leu Leu Pro Leu Val Ile Phe Phe Gly Leu Cys Leu Leu
ACA GTG CTG TTG CCC CTG GTC ATT TTC TTT GGT CTT TGC CTT TTA
846         855         864         873         882

200                        205                        210
Ser Leu Leu Phe Ile Gly Leu Met Tyr Arg Tyr Gln Arg Trp Lys
TCC CTC CTC TTC ATT GGT TTA ATG TAT CGC TAC CAA CGG TGG AAG
891         900         909         918         927

215                        220                        225
Ser Lys Leu Tyr Ser Ile Val Cys Gly Lys Ser Thr Pro Glu Lys
TCC AAG CTC TAC TCC ATT GTT TGT GGG AAA TCG ACA CCT GAA AAA
936         945         954         963         972

230                        235                        240
Glu Gly Glu Leu Glu Gly Thr Thr Thr Lys Pro Leu Ala Pro Asn
GAG GGG GAG CTT GAA GGA ACT ACT ACT AAG CCC CTG GCC CCA AAC
981         990         999         1008        1017
```

FIG. 1C

```
                      245                           250                           255
       Pro Ser Phe Ser Pro Thr Pro Gly Phe Thr Pro Thr Leu Gly Phe
       CCA AGC TTC AGT CCC ACT CCA GGC TTC ACC CCC ACC CTG GGC TTC
       1026            1035            1044            1053            1062

260                           265                           270
       Ser Pro Val Pro Ser Ser Thr Phe Thr Ser Ser Ser Thr Tyr Thr
       AGT CCC GTG CCC AGT TCC ACC TTC ACC TCC AGC TCC ACC TAT ACC
       1071            1080            1089            1098            1107

275                           280                           285
       Pro Gly Asp Cys Pro Asn Phe Ala Ala Pro Arg Arg Glu Val Ala
       CCC GGT GAC TGT CCC AAC TTT GCG GCT CCC CGC AGA GAG GTG GCA
       1116            1125            1134            1143            1152

290                           295                           300
       Pro Pro Tyr Gln Gly Ala Asp Pro Ile Leu Ala Thr Ala Leu Ala
       CCA CCC TAT CAG GGG GCT GAC CCC ATC CTT GCG ACA GCC CTC GCC
       1161            1170            1179            1188            1197

305                           310                           315
       Ser Asp Pro Ile Pro Asn Pro Leu Gln Lys Trp Glu Asp Ser Ala
       TCC GAC CCC ATC CCC AAC CCC CTT CAG AAG TGG GAG GAC AGC GCC
       1206            1215            1224            1233            1242

320                           325                           330
       His Lys Pro Gln Ser Leu Asp Thr Asp Asp Pro Ala Thr Leu Tyr
       CAC AAG CCA CAG AGC CTA GAC ACT GAT GAC CCC GCG ACG CTG TAC
       1251            1260            1269            1278            1287

335                           340
       Ala Val Val Glu Asn Val Pro Pro Leu Arg Trp
       GCC GTG GTG GAG AAC GTG CCC CCG TTG CGC TGG AA GGAATTC
       1296            1305            1314            1323       1332
```

FIG. 6A pAD-CMV1 : 6414 bp

| | | | | | |
|---|---|---|---|---|---|
| TCGACATTGA | TTATTGACTA | GTTATTAATA | GTAATCAATT | ACGGGGTCAT | TAGTTCATAG | 60 |
| CCCATATATG | GAGTTCCGCG | TTACATAACT | TACGGTAAAT | GGCCCGCCTG | GCTGACCGCC | 120 |
| CAACGACCCC | CGCCCATTGA | CGTCAATAAT | GACGTATGTT | CCCATAGTAA | CGCCAATAGG | 180 |
| GACTTTCCAT | TGACGTCAAT | GGGTGGAGTA | TTTACGGTAA | ACTGCCCACT | TGGCAGTACA | 240 |
| TCAAGTGTAT | CATATGCCAA | GTACGCCCCC | TATTGACGTC | AATGACGGTA | AATGGCCCGC | 300 |
| CTGGCATTAT | GCCCAGTACA | TGACCTTATG | GGACTTTCCT | ACTTGGCAGT | ACATCTACGT | 360 |
| ATTAGTCATC | GCTATTACCA | TGGTGATGCG | GTTTTGGCAG | TACATCAATG | GGCGTGGATA | 420 |
| GCGGTTTGAC | TCACGGGGAT | TTCCAAGTCT | CCACCCCATT | GACGTCAATG | GGAGTTTGTT | 480 |
| TTGGCACCAA | AATCAACGGG | ACTTTCCAAA | ATGTCGTAAC | AACTCCGCCC | CATTGACGCA | 540 |
| AATGGGCGGT | AGGCGTGTAC | GGTGGGAGGT | CTATATAAGC | AGAGCTCTCT | GGCTAACTAG | 600 |
| AGAACCCACT | GCTTAACTGG | CTTATCGAAA | TTAATACGAC | TCACTATAGG | GAGACCCAAG | 660 |
| CTTCTGCAGG | TCGACATCGA | TGGATCCGGT | ACCTCGAGCG | CGAATTCTCT | AGAGGATCTT | 720 |
| TGTGAAGGAA | CCTTACTTCT | GTGGTGTGAC | ATAATTGGAC | AAACTACCTA | CAGAGATTTA | 780 |
| AAGCTCTAAG | GTAAATATAA | AATTTTTAAG | TGTATAATGT | GTTAAACTAC | TGATTCTAAT | 840 |
| TGTTTGTGTA | TTTTAGATTC | CAACCTATGG | AACTGATGAA | TGGGAGCAGT | GGTGGAATGC | 900 |
| CTTTAATGAG | GAAAACCTGT | TTTGCTCAGA | AGAAATGCCA | TCTAGTGATG | ATGAGGCTAC | 960 |
| TGCTGACTCT | CAACATTCTA | CTCCTCCAAA | AAGAAGAGA | AAGGTAGAAG | ACCCCAAGGA | 1020 |
| CTTTCCTTCA | GAATTGCTAA | GTTTTTTGAG | TCATGCTGTG | TTTAGTAATA | GAACTCTTGC | 1080 |
| TTGCTTTGCT | ATTTACACCA | CAAAGGAAAA | AGCTGCACTG | CTATACAAGA | AAATTATGGA | 1140 |
| AAAATATTTG | ATGTATAGTG | CCTTGACTAG | AGATCATAAT | CAGCCATACC | ACATTTGTAG | 1200 |
| AGGTTTTACT | TGCTTTAAAA | AACCTCCCAC | ACCTCCCCCT | GAACCTGAAA | CATAAAATGA | 1260 |
| ATGCAATTGT | TGTTGTTAAC | TTGTTTATTG | CAGCTTATAA | TGGTTACAAA | TAAAGCAATA | 1320 |
| GCATCACAAA | TTTCACAAAT | AAAGCATTTT | TTTCACTGCA | TTCTAGTTGT | GGTTTGTCCA | 1380 |
| AACTCATCAA | TGTATCTTAT | CATGTCTGGA | TCAATTCTGA | GAAACTAGCC | TTAAAGACAG | 1440 |

FIG. 6B

```
ACAGCTTTGT TCTAGTCAGC CAGGCAAGCA TATGTAAATA AAGTTCCTCA GGGAACTGAG   1500

GTTAAAAGAT GTATCCTGGA CCTGCCAGAC CTGGCCATTC ACGTAAACAG AAGATTCCGC   1560

CTCAAGTTCC GGTTAACAAC AGGAGGCAAC GAGATCTCAA ATCTATTACT TCTAATCGGG   1620

TAATTAAAAC CTTTCAACTA AAACACGGAC CCACGGATGT CACCCACTTT TCCTTCCCCG   1680

GCTCCGCCCT TCTCAGTACT CCCCACCATT AGGCTCGCTA CTCCACCTCC ACTTCCGGGC   1740

GCGACACCCA CGTGCCCTCT CCCACCCGAC GCTAACCCCG CCCCTGCCCG TCTGACCCCG   1800

CCCACCACCT GGCCCCGCCC CGTTGAGGAC AGAAGAAACC CCGGGCAGCC GCAGCCAAGG   1860

CGGACGGGTA GACGCTGGGG GCGCTGAGGA GTCGTCCTCT ACCTTCTCTG CTGGCTCGGT   1920

GGGGGACGCG GTGGATCTCA GGCTTCCGGA AGACTGGAAG AACCGGCTCA GAACCGCTTG   1980

TCTCCGCGGG GCTTGGGCGG CGGAAGAATG GCCGCTAGAC GCGGACTTGG TGCGAGGCAT   2040

CGCAGGATGC AGAAGAGCAA GCCCGCCGGG AGCGCGCGGC TGTACTACCC CGCGCCTGGA   2100

GCGGCCACGC CGGACTGGGC GGGGCCGGCC TGGTGGAGGC GGAGTCTGAC CTCGTGGAGG   2160

CGGGGCCTCT GATGTTCAAA TAGGATGCTA GGCTTGTTGA GGCGTGGCCT CCGATTCACA   2220

AGTGGGAAGC AGCGCCGGGC GACTGCAATT TCGCGCCAAA CTTGGGGGAA GCACAGCGTA   2280

CAGGCTGCCT AGGTGATCGC TGCTGCTGTC ATGGTTCGAC CGCTGAACTG CATCGTCGCC   2340

GTGTCCCAGA ATATGGGCAT CGGCAAGAAC GGAGACCTTC CCTGGCCAAT GCTCAGGTAC   2400

TGGCTGGATT GGGTTAGGGA AACCGAGGCG GTTCGCTGAA TCGGGTCGAG CACTTGGCGG   2460

AGACGCGCGG GCCAACTACT TAGGGACAGT CATGAGGGGT AGGCCCGCCG GCTGCTGCCC   2520

TTGCCCATGC CCGCGGTGAT CCCCATGCTG TGCCAGCCTT TGCCCAGAGG CGCTCTAGCT   2580

GGGAGCAAAG TCCGGTCACT GGGCAGCACC ACCCCCCGGA CTTGCATGGG TAGCCGCTGA   2640

GATGGAGCCT GAGCACACGT GACAGGGTCC CTGTTAACGC AGTGTTTCTC TAACTTTCAG   2700

GAACGAGTTC AAGTACTTCC AAAGAATGAC CACCACCTCC TCAGTGGAAG GTAAACAGAA   2760

CCTGGTGATT ATGGGCCGGA AAACCTGGTT CTCCATTCCT GAGAAGAATC GACCTTTAAA   2820

GGACAGAATT AATATAGTTC TCAGTAGAGA GCTCAAGGAA CCACCACAAG GAGCTCATTT   2880

TCTTGCCAAA AGTCTGGACC ATGCCTTAAA ACTTATTGAA CAACCAGAGT TAGCAGATAA   2940

AGTGGACATG GTTTGGATAG TTGGAGGCAG TTCCGTTTAC AAGGAAGCCA TGAATCAGCC   3000
```

FIG. 6C

```
AGGCCATCTC AGACTCTTTG TGACAAGGAT CATGCAGGAA TTTGAAAGTG ACACGTTCTT    3060

CCCAGAAATT GATTTGGAGA AATATAAACT TCTCCCAGAG TACCCAGGGG TCCTTTCTGA    3120

AGTCCAGGAG GAAAAAGGCA TCAAGTATAA ATTTGAAGTC TATGAGAAGA AAGGCTAACA    3180

GAAAGATACT TGCTGATTGA CTTCAAGTTC TACTGCTTTC CTCCTAAAAT TATGCATTTT    3240

TACAAGACCA TGGGACTTGT GTTGGCTTTA GATCCTGTGC ATCCTGGGCA ACTGTTGTAC    3300

TCTAAGCCAC TCCCCAAAGT CATGCCCCAG CCCCTGTATA ATTCTAAACA ATTAGAATTA    3360

TTTTCATTTT CATTAGTCTA ACCAGGTTAT ATTAAATATA CTTTAAGAAA CACCATTTGC    3420

CATAAAGTTC TCAATGCCCC TCCCATGCAG CCTCAAGTGG CTCCCCAGCA GATGCATAGG    3480

GTAGTGTGTG TACAAGAGAC CCCAAAGACA TAGAGCCCCT GAGAGCATGA GCTGATATGG    3540

GGGCTCATAG AGATAGGAGC TAGATGAATA AGTACAAAGG GCAGAAATGG GTTTTAACCA    3600

GCAGAGCTAG AACTCAGACT TTAAAGAAAA TTAGATCAAA GTAGAGACTG AATTATTCTG    3660

CACATCAGAC TCTGAGCAGA GTTCTGTTCA CTCAGACAGA AAATGGGTAA ATTGAGAGCT    3720

GGCTCCATTG TGCTCCTTAG AGATGGGAGC AGGTGGAGGA TTATATAAGG TCTGGAACAT    3780

TTAACTTCTC CGTTTCTCAT CTTCAGTGAG ATTCCAAGGG ATACTACAAT TCTGTGGAAT    3840

GTGTGTCAGT TAGGGTGTGG AAAGTCCCCA GGCTCCCCAG CAGGCAGAAG TATGCAAAGC    3900

ATGCATCTCA ATTAGTCAGC AACCAGGTGT GGAAAGTCCC CAGGCTCCCC AGCAGGCAGA    3960

AGTATGCAAA GCATGCATCT CAATTAGTCA GCAACCATAG TCCCGCCCCT AACTCCGCCC    4020

ATCCCGCCCC TAACTCCGCC CAGTTCCGCC CATTCTCCGC CCCATGGCTG ACTAATTTTT    4080

TTTATTTATG CAGAGGCCGA GGCGCCTCTG AGCTATTCCA GAAGTAGTGA GGAGGCTTTT    4140

TTGGAGGCCT AGGCTTTTGC AAAAAAGCTA ATTCAGCCTG AATGGCGAAT GGGACGCGCC    4200

CTGTAGCGGC GCATTAAGCG CGGCGGGTGT GGTGGTTACG CGCAGCGTGA CCGCTACACT    4260

TGCCAGCGCC CTAGCGCCCG CTCCTTTCGC TTTCTTCCCT TCCTTTCTCG CCACGTTCGC    4320

CGGCTTTCCC CGTCAAGCTC TAAATCGGGG GCTCCCTTTA GGGTTCCGAT TTAGTGCTTT    4380

ACGGCACCTC GACCCCAAAA ACTTGATTAG GGTGATGGTT CACGTAGTGG GCCATCGCCC    4440

TGATAGACGG TTTTTCGCCC TTTGACGTTG GAGTCCACGT TCTTTAATAG TGGACTCTTG    4500

TTCCAAACTG GAACAACACT CAACCCTATC TCGGTCTATT CTTTTGATTT ATAAGGGATT    4560
```

FIG. 6D

```
TTGCCGATTT CGGCCTATTG GTTAAAAAAT GAGCTGATTT AACAAAAATT TAACGCGAAT   4620
TTTAACAAAA TATTAACGTT TACAATTTCA GGTGGCACTT TTCGGGGAAA TGTGCGCGGA   4680
ACCCCTATTT GTTTATTTTT CTAAATACAT TCAAATATGT ATCCGCTCAT GAGACAATAA   4740
CCCTGATAAA TGCTTCAATA ATATTGAAAA AGGAAGAGTA TGAGTATTCA ACATTTCCGT   4800
GTCGCCCTTA TTCCCTTTTT TGCGGCATTT TGCCTTCCTG TTTTTGCTCA CCCAGAAACG   4860
CTGGTGAAAG TAAAAGATGC TGAAGATCAG TTGGGTGCAC GAGTGGGTTA CATCGAACTG   4920
GATCTCAACA GCGGTAAGAT CCTTGAGAGT TTTCGCCCCG AAGAACGTTT TCCAATGATG   4980
AGCACTTTTA AAGTTCTGCT ATGTGGCGCG GTATTATCCC GTATTGACGC CGGGCAAGAG   5040
CAACTCGGTC GCCGCATACA CTATTCTCAG AATGACTTGG TTGAGTACTC ACCAGTCACA   5100
GAAAAGCATC TTACGGATGG CATGACAGTA AGAGAATTAT GCAGTGCTGC CATAACCATG   5160
AGTGATAACA CTGCGGCCAA CTTACTTCTG ACAACGATCG GAGGACCGAA GGAGCTAACC   5220
GCTTTTTTGC ACAACATGGG GGATCATGTA ACTCGCCTTG ATCGTTGGGA ACCGGAGCTG   5280
AATGAAGCCA TACCAAACGA CGAGCGTGAC ACCACGATGC CTGTAGCAAT GGCAACAACG   5340
TTGCGCAAAC TATTAACTGG CGAACTACTT ACTCTAGCTT CCCGGCAACA ATTAATAGAC   5400
TGGATGGAGG CGGATAAAGT TGCAGGACCA CTTCTGCGCT CGGCCCTTCC GGCTGGCTGG   5460
TTTATTGCTG ATAAATCTGG AGCCGGTGAG CGTGGGTCTC GCGGTATCAT TGCAGCACTG   5520
GGGCCAGATG GTAAGCCCTC CCGTATCGTA GTTATCTACA CGACGGGGAG TCAGGCAACT   5580
ATGGATGAAC GAAATAGACA GATCGCTGAG ATAGGTGCCT CACTGATTAA GCATTGGTAA   5640
CTGTCAGACC AAGTTTACTC ATATATACTT TAGATTGATT TAAAACTTCA TTTTTAATTT   5700
AAAAGGATCT AGGTGAAGAT CCTTTTTGAT AATCTCATGA CCAAAATCCC TTAACGTGAG   5760
TTTTCGTTCC ACTGAGCGTC AGACCCCGTA GAAAAGATCA AAGGATCTTC TTGAGATCCT   5820
TTTTTTCTGC GCGTAATCTG CTGCTTGCAA ACAAAAAAAC CACCGCTACC AGCGGTGGTT   5880
TGTTTGCCGG ATCAAGAGCT ACCAACTCTT TTTCCGAAGG TAACTGGCTT CAGCAGAGCG   5940
CAGATACCAA ATACTGTCCT TCTAGTGTAG CCGTAGTTAG GCCACCACTT CAAGAACTCT   6000
GTAGCACCGC CTACATACCT CGCTCTGCTA ATCCTGTTAC CAGTGGCTGC TGCCAGTGGC   6060
GATAAGTCGT GTCTTACCGG GTTGGACTCA AGACGATAGT TACCGGATAA GGCGCAGCGG   6120
```

FIG. 6E

```
TCGGGCTGAA CGGGGGGTTC GTGCACACAG CCCAGCTTGG AGCGAACGAC CTACACCGAA    6180

CTGAGATACC TACAGCGTGA GCATTGAGAA AGCGCCACGC TTCCCGAAGG GAGAAAGGCG    6240

GACAGGTATC CGGTAAGCGG CAGGGTCGGA ACAGGAGAGC GCACGAGGGA GCTTCCAGGG    6300

GGAAACGCCT GGTATCTTTA TAGTCCTGTC GGGTTTCGCC ACCTCTGACT TGAGCGTCGA    6360

TTTTTGTGAT GCTCGTCAGG GGGCGGAGC CTATGGAAAA ACGCCAGCAA CGCC
```

FIG. 8A raTNF-R

```
GAATTCCTTT TCTCCGAGTT TTCTGAACTC TGGCTCATGA TCGGGCTTAC TGGATACGAG      60
AATCCTGGAG, GACCGTACCC TGATTTCCAT CTACCTCTGA CTTTGAGCCT TTCTAACCCG     120
GGGCTCACGC TGCCAACACC CGGGCCACCT GGTCCGATCG TCTTACTTCA TTCACCAGCG     180
TTGCCAATTG CTGCCCTGTC CCCAGCCCCA ATGGGGAGT GAGAGAGGCC ACTGCCGGCC      240
GGAC
```

```
245/1                                        275/11
ATG GGT CTC CCC ATC GTG CCT GGC CTG CTG CTG TCA CTG GTG CTC CTG GCT CTG CTG ATG
Met Gly Leu Pro Ile Val Pro Gly Leu Leu Leu Ser Leu Val Leu Leu Ala Leu Leu Met
305/21                                       335/31
GGG ATA CAC CCA TCA GGG GTC ACC GGA CTG GTT CCT TCT CTT GGT GAC CGG GAG AAG AGG
Gly Ile His Pro Ser Gly Val Thr Gly Leu Val Pro Ser Leu Gly Asp Arg Glu Lys Arg
365/41                                       395/51
GAT AAT TTG TGT CCC CAG GGA AAG TAT GCC CAT CCA AAG AAT AAT TCC ATC TGC TGC ACC
Asp Asn Leu Cys Pro Gln Gly Lys Tyr Ala His Pro Lys Asn Asn Ser Ile Cys Cys Thr
425/61                                       455/71
AAG TGC CAC AAA GGA ACC TAC TTG GTG AGT GAC TGT CCA AGC CCA GGG CAG GAA ACA GTC
Lys Cys His Lys Gly Thr Tyr Leu Val Ser Asp Cys Pro Ser Pro Gly Gln Glu Thr Val
485/81                                       515/91
TGC GAG CTC TCT CAT AAA GGC ACC TTT ACA GCT TCG CAG AAC CAC GTC AGA CAG TGT CTC
Cys Glu Leu Ser His Lys Gly Thr Phe Thr Ala Ser Gln Asn His Val Arg Gln Cys Leu
545/101                                      575/111
AGT TGC AAG ACA TGT CGG AAA GAA ATG TTC CAG GTG GAG ATT TCT CCT TGC AAA GCT GAC
Ser Cys Lys Thr Cys Arg Lys Glu Met Phe Gln Val Glu Ile Ser Pro Cys Lys Ala Asp
605/121                                      635/131
ATG GAC ACC GTG TGT GGC TGC AAG AAG AAC CAA TTC CAG CGC TAC CTG AGT GAG ACG CAT
Met Asp Thr Val Cys Gly Cys Lys Lys Asn Gln Phe Gln Arg Tyr Leu Ser Glu Thr His
665/141                                      695/151
TTC CAG TGT GTG GAC TGC AGC CCC TGC TTC AAT GGC ACC GTG ACA ATC CCC TGT AAG GAG
Phe Gln Cys Val Asp Cys Ser Pro Cys Phe Asn Gly Thr Val Thr Ile Pro Cys Lys Glu
725/161                                      755/171
AAA CAG AAC ACC GTG TGT AAC TGC CAC GCA GGA TTC TTT CTA AGC GGA AAT GAG TGC ACC
Lys Gln Asn Thr Val Cys Asn Cys His Ala Gly Phe Phe Leu Ser Gly Asn Glu Cys Thr
785/181                                      815/191
CCT TGC AGC CAC TGC AAG AAA AAT CAG GAA TGT ATG AAG CTG TGC CTA CCT CCA GTT GCA
Pro Cys Ser His Cys Lys Lys Asn Gln Glu Cys Met Lys Leu Cys Leu Pro Pro Val Ala
845/201                                      875/211
AAT GTC ACA AAC CCC CAG GAC TCA GGT ACT GCC GTG CTG TTG CCT CTG GTT ATC TTC CTA
Asn Val Thr Asn Pro Gln Asp Ser Gly Thr Ala Val Leu Leu Pro Leu Val Ile Phe Leu
905/221                                      935/231
GGT CTT TGC CTT TTA TTC TTT ATC TGC ATC AGT CTA CTG TGC CGA TAT CCC CAG TGG AGG
Gly Leu Cys Leu Leu Phe Phe Ile Cys Ile Ser Leu Leu Cys Arg Tyr Pro Gln Trp Arg
965/241                                      995/251
CCC AGG GTC TAC TCC ATC ATT TGT AGG GAT TCA GCT CCT GTC AAA GAG GTG GAG GGT GAA
Pro Arg Val Tyr Ser Ile Ile Cys Arg Asp Ser Ala Pro Val Lys Glu Val Glu Gly Glu
1025/261                                     1055/271
GGA ATT GTT ACT AAG CCC CTA ACT CCA GCC TCT ATC CCA GCC TTC AGC CCC AAC CCC GGC
Gly Ile Val Thr Lys Pro Leu Thr Pro Ala Ser Ile Pro Ala Phe Ser Pro Asn Pro Gly
1085/281                                     1115/291
TTC AAC CCC ACT CTG GGC TTC AGC ACC ACC CCA CGC TTC AGT CAT CCT GTC TCC AGT ACC
Phe Asn Pro Thr Leu Gly Phe Ser Thr Thr Pro Arg Phe Ser His Pro Val Ser Ser Thr
1145/301                                     1175/311
CCC ATC AGC CCC GTC TTC GGT CCT AGT AAC TGG CAC AAC TTC GTG CCA CCT GTA AGA GAG
Pro Ile Ser Pro Val Phe Gly Pro Ser Asn Trp His Asn Phe Val Pro Pro Val Arg Glu
1205/321                                     1235/331
GTG GTC CCA ACC CAG GGT GCT GAC CCT CTC CTC TAC GGA TCC CTC AAC CCT GTG CCA ATC
Val Val Pro Thr Gln Gly Ala Asp Pro Leu Leu Tyr Gly Ser Leu Asn Pro Val Pro Ile
```

FIG. 8B

```
1265/341                              1295/351
CCC GCC CCT GTT CGG AAA TGG GAA GAC GTC GTC GCG GCC CAG CCA CAA CGG CTT GAC ACT
Pro Ala Pro Val Arg Lys Trp Glu Asp Val Val Ala Ala Gln Pro Gln Arg Leu Asp Thr
1325/361                              1355/371
GCA GAC CCT GCG ATG CTG TAT GCT GTG GTG GAT GGC GTG CCT CCG ACA CGC TGG AAG GAG
Ala Asp Pro Ala Met Leu Tyr Ala Val Val Asp Gly Val Pro Pro Thr Arg Trp Lys Glu
1385/381                              1415/391
TTC ATG CGG CTC CTG GGG CTG AGC GAG CAC GAG ATC GAG CGG CTG GAG CTG CAG AAC GGG
Phe Met Arg Leu Leu Gly Leu Ser Glu His Glu Ile Glu Arg Leu Glu Leu Gln Asn Gly
1445/401                              1475/411
CGT TGC CTC CGC GAG GCT CAT TAC AGC ATG CTG GAA GCC TGG CGG CGC CGC ACA CCG CGA
Arg Cys Leu Arg Glu Ala His Tyr Ser Met Leu Glu Ala Trp Arg Arg Arg Thr Pro Arg
1505/421                              1535/431
CAC GAG GCC ACG CTG GAC GTA GTG GGC CGC GTG CTT TGC GAC ATG AAC CTG CGT GGC TGC
His Glu Ala Thr Leu Asp Val Val Gly Arg Val Leu Cys Asp Met Asn Leu Arg Gly Cys
1565/441                              1595/451
CTG GAG AAC ATC CGC GAG ACT CTA GAA AGC CCT GCC CAC TCG TCC ACG ACC CAC CTC CCG
Leu Glu Asn Ile Arg Glu Thr Leu Glu Ser Pro Ala His Ser Ser Thr Thr His Leu Pro
1625/461
CGA TAA
Arg Stop
            GGCCACACCC CCACCTCAGG AACGGGACTC GAAGGACCAT CCTGCTAGAT  1680
GCCCTGCTTC CCTGTGAACC TCCTCTTTGG TCCTCTAGGG GGCAGGCTCG ATCTGGCAGG  1740
CTCGATCTGG CAGCCACTTC CTTGGTGCTA CCGACTTGGT GTACATAGCT TTTCCCAGCT  1800
GCCGAGGACA GCCTGTGCCA GCCACTTGTG CATGGCAGGG AAGTGTGCCA TCTGCTCCCA  1860
GACAGCTGAG GGTGCCAAAA GCCAGGAGAG GTGATTGTGG AGAAAAAGCA CAATCTATCT  1920
GATACCCACT TGGGATGCAA GGACCCAAAC AAAGCTTCTC AGGGCCTCCT CAGTTGATTT  1980
CTGGGCCCTT TTCACAGTAG ATAAAACAGT CTTTGTATTG ATTATATCAC ACTAATGGAT  2040
GAACGGTTGA ACTCCCTAAG GTAGGGCAA GCACAGAACA GTGGGGTCTC CAGCTGGAGC  2100
CCCCGACTCT TGTAAATACA CTAAAAATCT AAAAGTGAAA AAAAAAAAA AAAAAAAAA    2160
AAAAAAGGAA TTC
```

FIG. 9A huTNF-R

```
GAATTCTCTG GACTGAGGCT CCAGTTCTGG CCTTTGGGGT TCAAGATCAC TGGGACCAGG    60
CCGTGATCTC TATGCCCGAG TCTCAACCCT CAACTGTCAC CCCAAGGCAC TTGGGACGTC   120
CTGGACAGAC CGAGTCCCGG GAAGCCCCAG CACTGCCGCT GCCACACTGC CCTGAGCCCA   180
AATGGGGGAG TGAGAGGCCA TAGCTGTCTG GC
```

```
213/1                                       243/11
ATG GGC CTC TCC ACC GTG CCT GAC CTG CTG CTG CCA CTG GTG CTC CTG GAG CTG TTG GTG
Met Gly Leu Ser Thr Val Pro Asp Leu Leu Leu Pro Leu Val Leu Leu Glu Leu Leu Val
273/21                                      303/31
GGA ATA TAC CCC TCA GGG GTT ATT GGA CTG GTC CCT CAC CTA GGG GAC AGG GAG AAG AGA
Gly Ile Tyr Pro Ser Gly Val Ile Gly Leu Val Pro His Leu Gly Asp Arg Glu Lys Arg
333/41                                      363/51
GAT AGT GTG TGT CCC CAA GGA AAA TAT ATC CAC CCT CAA AAT AAT TCG ATT TGC TGT ACC
Asp Ser Val Cys Pro Gln Gly Lys Tyr Ile His Pro Gln Asn Asn Ser Ile Cys Cys Thr
393/61                                      423/71
AAG TGC CAC AAA GGA ACC TAC TTG TAC AAT GAC TGT CCA GGC CCG GGG CAG GAT ACG GAC
Lys Cys His Lys Gly Thr Tyr Leu Tyr Asn Asp Cys Pro Gly Pro Gly Gln Asp Thr Asp
453/81                                      483/91
TGC AGG GAG TGT GAG AGC GGC TCC TTC ACC GCT TCA GAA AAC CAC CTC AGA CAC TGC CTC
Cys Arg Glu Cys Glu Ser Gly Ser Phe Thr Ala Ser Glu Asn His Leu Arg His Cys Leu
513/101                                     543/111
AGC TGC TCC AAA TGC CGA AAG GAA ATG GGT CAG GTG GAG ATC TCT TCT TGC ACA GTG GAC
Ser Cys Ser Lys Cys Arg Lys Glu Met Gly Gln Val Glu Ile Ser Ser Cys Thr Val Asp
573/121                                     603/131
CGG GAC ACC GTG TGT GGC TGC AGG AAG AAC CAG TAC CGG CAT TAT TGG AGT GAA AAC CTT
Arg Asp Thr Val Cys Gly Cys Arg Lys Asn Gln Tyr Arg His Tyr Trp Ser Glu Asn Leu
633/141                                     663/151
TTC CAG TGC TTC AAT TGC AGC CTC TGC CTC AAT GGG ACC GTG CAC CTC TCC TGC CAG GAG
Phe Gln Cys Phe Asn Cys Ser Leu Cys Leu Asn Gly Thr Val His Leu Ser Cys Gln Glu
693/161                                     723/171
AAA CAG AAC ACC GTG TGC ACC TGC CAT GCA GGT TTC TTT CTA AGA GAA AAC GAG TGT GTC
Lys Gln Asn Thr Val Cys Thr Cys His Ala Gly Phe Phe Leu Arg Glu Asn Glu Cys Val
753/181                                     783/191
TCC TGT AGT AAC TGT AAG AAA AGC CTG GAG TGC ACG AAG TTG TGC CTA CCC CAG ATT GAG
Ser Cys Ser Asn Cys Lys Lys Ser Leu Glu Cys Thr Lys Leu Cys Leu Pro Gln Ile Glu
813/201                                     843/211
AAT GTT AAG GGC ACT GAG GAC TCA GGC ACC ACA GTG CTG TTG CCC CTG GTC ATT TTC TTT
Asn Val Lys Gly Thr Glu Asp Ser Gly Thr Thr Val Leu Leu Pro Leu Val Ile Phe Phe
873/221                                     903/231
GGT CTT TGC CTT TTA TCC CTC CTC TTC ATT GGT TTA ATG TAT CGC TAC CAA CGG TGG AAG
Gly Leu Cys Leu Leu Ser Leu Leu Phe Ile Gly Leu Met Tyr Arg Tyr Gln Arg Trp Lys
933/241                                     963/251
TCC AAG CTC TAC TCC ATT GTT TGT GGG AAA TCG ACA CCT GAA AAA GAG GGG GAG CTT GAA
Ser Lys Leu Tyr Ser Ile Val Cys Gly Lys Ser Thr Pro Glu Lys Glu Gly Glu Leu Glu
993/261                                     1023/271
GGA ACT ACT ACT AAG CCC CTG GCC CCA AAC CCA AGC TTC AGT CCC ACT CCA GGC TTC ACC
Gly Thr Thr Thr Lys Pro Leu Ala Pro Asn Pro Ser Phe Ser Pro Thr Pro Gly Phe Thr
1053/281                                    1083/291
CCC ACC CTG GGC TTC AGT CCC GTG CCC AGT TCC ACC TTC ACC TCC AGC TCC ACC TAT ACC
Pro Thr Leu Gly Phe Ser Pro Val Pro Ser Ser Thr Phe Thr Ser Ser Ser Thr Tyr Thr
1113/301                                    1143/311
CCC GGT GAC TGT CCC AAC TTT GCG GCT CCC CGC AGA GAG GTG GCA CCA CCC TAT CAG GGG
Pro Gly Asp Cys Pro Asn Phe Ala Ala Pro Arg Arg Glu Val Ala Pro Pro Tyr Gln Gly
1173/321                                    1203/331
GCT GAC CCC ATC CTT GCG ACA GCC CTC GCC TCC GAC CCC ATC CCC AAC CCC CTT CAG AAG
Ala Asp Pro Ile Leu Ala Thr Ala Leu Ala Ser Asp Pro Ile Pro Asn Pro Leu Gln Lys
```

FIG. 9B

```
1233/341                                 1263/351
TGG GAG GAC AGC GCC CAC AAG CCA CAG AGC CTA GAC ACT GAT GAC CCC GCG ACG CTG TAC
Trp Glu Asp Ser Ala His Lys Pro Gln Ser Leu Asp Thr Asp Asp Pro Ala Thr Leu Tyr
1293/361                                 1323/371
GCC GTG GTG GAG AAC GTG CCC CCG TTG CGC TGG AAG GAA TTC GTG CGG CGC CTA GGG CTG
Ala Val Val Glu Asn Val Pro Pro Leu Arg Trp Lys Glu Phe Val Arg Arg Leu Gly Leu
1353/381                                 1383/391
AGC GAC CAC GAG ATC GAT CGG CTG GAG CTG CAG AAC GGG CGC TGC CTG CGC GAG GCG CAA
Ser Asp His Glu Ile Asp Arg Leu Glu Leu Gln Asn Gly Arg Cys Leu Arg Glu Ala Gln
1413/401                                 1443/411
TAC AGC ATG CTG GCG ACC TGG AGG CGG CGC ACG CCG CGG CGC GAG GCC ACG CTG GAG CTG
Tyr Ser Met Leu Ala Thr Trp Arg Arg Arg Thr Pro Arg Arg Glu Ala Thr Leu Glu Leu
1473/421                                 1503/431
CTG GGA CGC GTG CTC CGC GAC ATG GAC CTG CTG GGC TGC CTG GAG GAC ATC GAG GAG GCG
Leu Gly Arg Val Leu Arg Asp Met Asp Leu Leu Gly Cys Leu Glu Asp Ile Glu Glu Ala
1533/441                                 1563/451
CTT TGC GGC CCC GCC GCC CTC CCG CCC GCG CCC AGT CTT CTC AGA TGA           1580
Leu Cys Gly Pro Ala Ala Leu Pro Pro Ala Pro Ser Leu Leu Arg Stop GGCTGCGCCC CTGCGGGCAG CTCTAAGGAC CGTCCTGCGA   1620
GATCGCCTTC CAACCCCACT TTTTTCTGGA AAGGAGGGGT CCTGCAGGGG CAAGCAGGAG  1680
CTAGCAGCCG CCTACTTGGT GCTAACCCCT CGATGTACAT AGCTTTTCTC AGCTGCCTGC  1740
GCGCCGCCGA CAGTCAGCGC TGTGCGCGCG GAGAGAGGTG CGCCGTGGGC TCAAGAGCCT  1800
GAGTGGGTGG TTTGCGAGGA TGAGGGACGC TATGCCTCAT GCCCGTTTTG GGTGTCCTCA  1860
CCAGCAAGGC TGCTCGGGGG CCCCTGGTTC GTCCCTGAGC CTTTTTCACA GTGCATAAGC  1920
AGTTTTTTTT GTTTTTGTTT TGTTTTGTTT TGTTTTTAAA TCAATCATGT TACACTAATA  1980
GAAACTTGGC ACTCCTGTGC CCTCTGCCTG GACAAGCACA TAGCAAGCTG AACTGTCCTA  2040
AGGCAGGGGC GAGCACGGAA CAATGGGGCC TTCAGCTGGA GCTGTGGACT TTTGTACATA  2100
CACTAAAATT CTGAAGTTAA AAAAAAAAA AAAAGGAATT C                       2141
```

TNF RECEPTORS, TNF BINDING PROTEINS AND DNAS CODING FOR THEM

This application is a continuation of application No. 08/153,287, filed Nov. 17, 1993 now abandoned, which is a continuation of Ser. No. 07/821,750, filed Jan. 1, 1992 now abandoned, and which is a division of Ser. No. 02/511,430 filed Apr. 30, 1990, now abandoned.

FIELD OF THE INVENTION

The invention is in the field of recombinant genetics. In particular, the invention relates to a TNF receptor and to a TNF binding protein produced by recombinant means.

BACKGROUND OF THE INVENTION

Tumour necrosis factor (TNF-α) was first found in the serum of mice and rabbits which had been infected with Bacillus Calmette-Guerin and which had been injected with endotoxin, and was recognized on the basis of its cytotoxic and antitumor properties (Carswell, E. A., et al., *Proc. Natl. Acad. Sci.* 25: 3666–3670 (1975)). It is produced particularly by activated macrophages and monocytes.

Numerous types of cells which are targets of TNF have surface receptors with a high affinity for this polypeptide (Old, L. J., *Nature* 326:330–331 (1987)); it was assumed that lymphotoxin (TNF-β) binds to the same receptor (Aggarwal, B. B., et al., *Nature* 318:655–667 (1985); Gullberg, U., et al., *Eur. J. Haematol.* 39:241–251 (1987)). TNF-α is identical to a factor referred to as cachectin (Beutler, B., et al., *Nature* 316:552–554 (1985)) which suppresses lipoprotein lipase and results in hypertriglyceridaemia in chronically inflammatory and malignant diseases (Torti, F. M. et al., *Nature* 229:867–869 (1985); Mahoney, J. R., et al., *J. Immunol.* 134:1673–1675 (1985)). TNF-α would appear to be involved in growth regulation and in the differentiation and function of cells which are involved in inflammation, immune processes and hematopoieses.

TNF can have a positive effect on the host organism by stimulating neutrophils (Shalaby, M. R., et al., *J. Immunol.* 135:2069–2073 (1985); Klebanoff, S. J., et al., *J. Immunol.* 136:4220–4225 (1986)) and monocytes and by inhibiting the replication of viruses (Mestan, J., et al., *Nature* 323:816–819 (1986); Wong, G. H. W., et al., *Nature* 323:819–822 (1986)). Moreover, TNF-α activates the immune defenses against parasites and acts directly and/or indirectly as a mediator in immune reactions, inflammatory processes and other processes in the body, although the mechanisms by which it works have not yet been clarified in a number of cases. However, the administration of TNF-α (Cerami, A., et al., *Immunol. Today* 9:28–31 (1988)) can also be accompanied by harmful phenomena (Tracey, K. J., et al., *Science* 234:470–474 (1986)) such as shock and tissue damage, which can be remedied by means of antibodies against TNF-α (Tracey, K. J., et al., *Nature* 330:662–666 (1987)).

A number of observations lead one to conclude that endogenously released TNF-α is involved in various pathological conditions. Thus, TNF-α appears to be a mediator of cachexia which can occur in chronically invasive, e.g. parasitic, diseases. TNF-α also appears to play a major part in the pathogenesis of shock caused by gram negative bacteria (endotoxic shock); it would also appear to be implicated in some if not all the effects of lipopolysaccharides (Beutler B., et al., *Ann. Rev. Biochem.* 57:505–18 (1988)). TNF has also been postulated to have a function in the tissue damage which occurs in inflammatory processes in the joints and other tissues, and in the lethality and morbidity of the graft-versus-host reaction (GVHR, Transplant Rejection (Piguet, P. F., et al., *Immunobiol.* 175:27 (1987)). A correlation has also been reported between the concentration of TNF in the serum and the fatal outcome of meningococcal diseases (Waage, A., et al., *Lancet* ii:355–357 (1987)).

It has also been observed that the administration of TNF-α over a lengthy period causes a state of anorexia and malnutrition which has symptoms similar to those of cachexia, which accompany neoplastic and chronic infectious diseases (Oliff A., et al., *Cell* 555–63 (1987)).

It has been reported that a protein derived from the urine of fever patients has a TNF inhibiting activity; the effect of this protein is presumed to be due to a competitive mechanism at the level of the receptors (similar to the effect of the interleukin-1 inhibitor (Seckinger, P., et al., *J. Immunol.* 139:1546–1549 (1987); Seckinger P., et al., *J. Exp. Med.*, 1511–16 (1988)).

EP-A2 308 378 describes a TNF inhibiting protein obtained from human urine. Its activity was demonstrated in the urine of healthy and ill subjects and determined on the basis of its ability to inhibit the binding of TNF-α to its receptors on human HeLa cells and FS 11 fibroblasts and the cytotoxic effect of TNF-α on murine A9 cells. The protein was purified until it became substantially homogeneous and characterized by its N-ending. This patent publication does indeed outline some theoretically possible methods of obtaining the DNA coding for the protein and the recombinant protein itself; however, there is no concrete information as to which of the theoretically possible solutions is successful.

SUMMARY OF THE INVENTION

The invention relates to DNA coding for a TNF receptor protein or a fragment thereof. In particular, the invention relates to DNA coding for the TNF receptor protein having the formula

ATG GGC CTC TCC ACC GTG CCT GAC CTG CTG CTG CCA CTG

GTG CTC CTG GAG CTG TTG GTG GGA ATA TAC CCC TCA GGG

GTT ATT GGA CTG GTC CCT CAC CTA GGG GAC AGG GAG AAG

AGA GAT AGT GTG TGT CCC CAA GGA AAA TAT ATC CAC CCT

CAA AAT AAT TCG ATT TGC TGT ACC AAG TGC CAC AAA GGA

ACC TAC TTG TAC AAT GAC TGT CCA GGC CCG GGG CAG GAT

ACG GAC TGC AGG GAG TGT GAG AGC GGC TCC TTC ACC GCT

TCA GAA AAC CAC CTC AGA CAC TGC CTC AGC TGC TCC AAA

TGC CGA AAG GAA ATG GGT CAG GTG GAG ATC TCT TCT TGC

ACA GTG GAC CGG GAC ACC GTG TGT GGC TGC AGG AAG AAC

CAG TAC CGG CAT TAT TGG AGT GAA AAC CTT TTC CAG TGC

TTC AAT TGC AGC CTC TGC CTC AAT GGG ACC GTG CAC CTC

TCC TGC CAG GAG AAA CAG AAC ACC GTG TGC ACC TGC CAT

GCA GGT TTC TTT CTA AGA GAA AAC GAG TGT GTC TCC TGT

AGT AAC TGT AAG AAA AGC CTG GAG TGC ACG AAG TTG TGC

CTA CCC CAG ATT GAG AAT GTT AAG GGC ACT GAG GAC TCA

-continued

```
GGC ACC ACA GTG CTG TTG CCC CTG GTC ATT TTC TTT GGT

CTT TGC CTT TTA TCC CTC CTC TTC ATT GGT TTA ATG TAT

CGC TAC CAA CGG TGG AAG TCC AAG CTC TAC TCC ATT GTT

TGT GGG AAA TCG ACA CCT GAA AAA GAG GGG GAG CTT GAA

GGA ACT ACT ACT AAG CCC CTG GCC CCA AAC CCA AGC TTC

AGT CCC ACT CCA GGC TTC ACC CCC ACC CTG GGC TTC AGT

CCC GTG CCC AGT TCC ACC TTC ACC TCC AGC TCC ACC TAT

ACC CCC GGT GAC TGT CCC ACC TTT GCG GCT CCC CGC AGA

GAG GTG GCA CCA CCC TAT CAG GGG GCT GAC CCC ATC CTT

GCG ACA GCC CTC GCC TCC GAC CCC ATC CCC AAC CCC CTT

CAG AAG TGG GAG GAC AGC GCC CAC AAG CCA CAG AGC CTA

GAC ACT GAT GAC CCC GCG ACG CTG TAC GCC GTG GTG GAG

AAC GTG CCC CCG TTG CGC TGG AAG GAA TTC GTG CGG CGC

CTA GGG CTG AGC GAC CAC GAG ATC GAT CGG CTG GAG CTG

CAG AAC GGG CGC TGC CTG CGC GAG GCG CAA TAC AGC ATG

CTG GCG ACC TGG AGG CGG CGC ACG CCG CGG CGC GAG GCC

ACG CTG GAG CTG CTG GGA CGC GTG CTC CGC GAC ATG GAC

CTG CTG GGC TGC CTG GAG GAC ATC GAG GAG GCG CTT TGC

GGC CCC GCC GCC CTC CCG CCC GCG CCC AGT CTT CTC AGA

TGA
``` or a fragment or a degenerate variant thereof.

The invention also relates to DNA coding for a secretable TNF-binding protein having the formula

```
R²  GAT AGT GTG TGT CCC CAA GGA AAA TAT ATC CAC CCT

CCA AAT AAT TCG ATT TGC TGT ACC AAG TGC CAC AAA GGA

ACC TAC TTG TAC AAT GAC TGT CCA GGC CCG GGG CAG GAT

ACG GAC TGC AGG GAG TGT GAG AGC GGC TCC TTC ACC GCT

TCA GAA AAC CAC CTC AGA CAC TGC CTC AGC TGC TCC AAA

TGC CGA AAG GAA ATG GGT CAG GTG GAG ATC TCT TCT TGC

ACA GTG GAC CGG GAC ACC GTG TGT GGC TGC AGG AAG AAC

CAG TAC CGG CAT TAT TGG AGT GAA AAC CTT TTC CAG TGC

TTC AAT TGC AGC CTC TGC CTC AAT GGG ACC GTG CAC CTC

TCC TGC CAG GAG AAA CAG AAC ACC GTG TGC ACC TGC CAT

GCA GGT TTC TTT CTA AGA GAA AAC GAG TGT GTC TCC TGT

AGT AAC TGT AAG AAA AGC CTG GAG TGC ACG AAG TTG TGC

CTA CCC CAG ATT GAG AAT
``` wherein R² is optionally absent or represents DNA coding for a polypeptide which can be cleaved in vivo; or a degenerate variant thereof.

The invention also relates to nucleic acid which hybridizes with the DNA of the invention under conditions of low stringency and which codes for a polypeptide having the ability to bind TNF.

The invention also relates to a recombinant DNA molecule, comprising the DNA molecules of the invention.

The invention also relates to host cells transformed with the recombinant DNA molecules of the invention.

The invention also relates to the substantially pure recombinant TNF receptor polypeptides of the invention. In particular, the invention relates to a TNF receptor of formula

```
met gly leu ser thr val pro asp leu leu leu pro leu val leu leu glu leu leu val gly ile tyr pro ser gly val ile gly leu val pro his leu gly asp arg glu lys arg asp ser val cys pro gln gly lys tyr ile his pro gln asn asn ser ile cys cys thr lys cys his lys gly thr tyr leu tyr asn asp cys pro gly pro gly gln asp thr asp cys arg glu cys glu ser gly ser phe thr ala ser glu asn his leu arg his cys leu ser cys ser lys cys arg lys glu met gly gln val glu ile ser ser cys thr val asp arg asp thr val cys gly cys arg lys asn gln tyr arg his tyr trp ser glu asn leu phe gln cys phe asn cys ser leu cys leu asn gly thr val his leu ser cys gln glu lys gln asn thr val cys thr cys his ala gly phe phe leu arg glu asn glu cys val ser cys ser asn cys lys lys ser leu glu cys thr lys leu cys leu pro gln ile glu asn val lys gly thr glu asp ser gly thr thr val leu leu pro leu val ile phe phe gly leu cys leu leu ser leu leu phe ile gly leu met tyr arg tyr gln arg trp lys ser lys leu tyr ser ile val cys gly lys ser thr pro glu lys glu gly glu leu glu gly thr thr thr lys pro leu ala pro asn pro ser phe ser pro thr pro gly phe thr pro thr leu gly phe ser pro val pro ser ser thr phe thr ser ser ser thr tyr thr pro gly asp cys pro asn phe ala ala pro arg arg glu val ala pro pro tyr gln gly ala asp pro ile leu ala thr ala leu ala ser asp pro ile pro asn pro leu gln lys trp glu asp ser ala his lys pro gln ser leu asp thr asp asp pro ala thr leu tyr ala val val glu asn val pro pro leu arg trp lys glu phe val arg arg leu gly leu ser asp his glu ile asp arg leu glu leu gln asn gly arg cys leu arg glu ala gln tyr ser met leu ala thr trp arg arg arg thr pro arg arg glu ala thr leu glu leu leu gly arg val leu arg asp met asp leu leu gly cys leu glu asp ile glu glu ala leu cys gly pro ala ala leu pro pro ala pro ser leu leu arg
``` or a fragment thereof which binds to TNF.

The invention also relates to the TNF binding protein of the formula

```
asp ser val cys pro gln gly lys tyr ile his pro gln
asn asn ser ile cys cys thr lys cys his lys gly thr
tyr leu tyr asn asp cys pro gly pro gly gln asp thr
asp cys arg glu cys glu ser gly ser phe thr ala ser
glu asn his leu arg his cys leu ser cys ser lys cys
arg lys glu met gly gln val glu ile ser ser cys thr
val asp arg asp thr val cys gly cys arg lys asn gln
tyr arg his tyr trp ser glu asn leu phe gln cys phe
asn cys ser leu cys leu asn gly thr val his leu ser
cys gln glu lys gln asn thr val cys thr cys his ala
gly peh phe leu arg glu asn glu cys val ser cys ser
asn cys lys lys ser leu glu cys thr lys leu cys leu
pro gln ile glu asn
``` or a functional derivative or fragment thereof having the ability to bind TNF.

The invention also relates to a process for preparing a recombinant TNF receptor protein, or a functional derivative thereof which is capable of binding to TNF, comprising cultivating a host cell of the invention and isolating the expressed recombinant TNF receptor protein.

The invention also relates to pharmaceutical compositions comprising a TNF receptor protein, or a functional derivative or fragment thereof, and a pharmaceutically acceptable carrier.

The invention also relates to a method for ameliorating the harmful effects of TNF in an animal, comprising administering to an animal in need of such treatment a therapeutically effective amount of a TNF receptor polypeptide, or fragment thereof which binds to TNF.

The invention also relates to a method for the detection of TNF in a biological sample, comprising contacting said sample with an effective amount of a TNF receptor polypeptide, or fragment thereof which binds to TNF, and detecting whether a complex is formed.

DESCRIPTION OF THE FIGURES

FIGS. 1A–1C depict the complete nucleotide sequence of 1334 bases of the cDNA insert of λTNF-BP15 and pTNF-BP15.

FIG. 2 depicts a hydrophobicity profile which was produced using the Mac Molly program.

FIG. 3 depicts the scheme used for the construction of plasmid pCMV-SV40.

FIG. 4 depicts the scheme used for the construction of plasmid pSV2gptDHFR Mut2.

FIG. 5 depicts the scheme used for the construction of plasmids pAD-CMV1 and pAD-CMV2.

FIGS. 6A–6E depict the full nucleotide sequence of the 6414 bp plasmid pADCMV1.

FIGS. 7A, 7B, 7C, and 7D depict the structure of the plasmids designated pADTNF-BP, pADBTNF-BP, pADTNF-R and pADBTNF-R.

FIGS. 8A–8B depict the complete nucleotide sequence of raTNF-R8.

FIGS. 9A–9B depict the complete coding region for human TNF-R in lTNF-R2.

FIG. 10 depicts an autoradiogram showing a singular RNA band with a length of 2.3 kb for the human TNF receptor.

BACKGROUND OF THE INVENTION

In preliminary tests for the purposes of the present invention (see Examples 1–4), a protein was identified from the dialyzed urine of uraemia patients, and this protein inhibits the biological effects of TNF-α by interacting with TNF-α to prevent it from binding to its cell surface receptor (Olsson I., et al., *Eur. J. Haematol.* 41:414–420 (1988)). This protein was also found to have an affinity for TNF-β.

The presence of this protein (hereinafter referred to as TNF-BP) in concentrated dialyzed urine was detected by competition with the binding of radioactively labelled recombinant TNF-α to a subclone of HL-60 cells, by measuring the influence of dialyzed urine on the binding of $^{125}$I-TNF-α to the cells. The binding tests carried out showed a dosage dependent inhibition of TNF-α binding to the cells by concentrated dialyzed urine (the possible interpretation that the reduction in binding observed might be caused by any TNF-α present in the urine or by TNF-β competing for the binding, was ruled out by the discovery that the reduction in binding could not be remedied by the use of TNF-α and TNF-β anti-bodies).

Analogously, in preliminary tests for the purposes of the present invention, it was demonstrated that TNF-BP also shows an affinity for TNF-β, which is about 1/50 of its affinity for TNF-α.

Gel chromatography on Sephacryl 200 showed that a substance in the urine and serum of dialysis patients and in the serum of healthy subjects forms a complex with recombinant TNF-α with a molecular weight of about 75,000.

TNF-BP was concentrated 62 times from several samples of dialyzed urine from uraemia patients by partial purification using pressure ultrafiltration, ion exchange chromatography and gel chromatography.

The preparations obtained were used to detect the biological activity of TNF-BP by inhibiting the growth-inhibiting effect of TNF-α on HL-60-10 cells. TNF-BP was found to have a dosage dependent effect on the biological activity of TNF-α. The binding characteristics of cells was also investigated by pretreatment with TNF-BP and an exclusive competition binding test. It was shown that pretreatment of the cells with TNF-BP does not affect the binding of TNF-α to the cells. This indicates that the effect of TNF-BP is not based on any binding to the cells and competition with TNF-α for the binding to the receptor.

The substantially homogeneous protein is obtained in highly purified form by concentrating urine from dialysis patients by ultrafiltration, dialyzing the concentrated urine and concentrating it four-fold in a first purification step using DEAE sephacel chromatography. Further concentration was carried out by affinity chromatography using sepharose-bound TNF-α. The final purification was carried out using reverse phase chromatography (FPLC).

It was shown that the substantially highly purified protein inhibits the cytotoxic effect of TNF-α on WEHI 164 clone 13 cells (Olsson et al., *Eur. J. Haematol.* 42:270–275 (1989)).

The N-terminal amino acid sequence of the substantially highly purified protein was analyzed. It was found to be Asp-Ser-Val-Xaa-Pro-Gln-Gly-Lys-Tyr-Ile-His-Pro-Gln (main sequence); the following N-terminal sequence was detected in traces: Leu-(Val)-(Pro)-(His)-Leu-Gly-Xaa-Arg-Glu (subsidiary sequence). A comparison of the main sequence with the N-terminal sequence of the TNF-inhibiting protein disclosed in EP-A2 308 378 shows that the two proteins are identical.

The following amino acid composition was found, given in mols of amino acid per mol of protein and in mol-% of amino acid, measured as the average of 24-hour and 48-hour hydrolysis:

|  | Mol of amino acid/ mol of protein | Mol % amino acid |
| --- | --- | --- |
| Asp + Asn | 27.5 | 10.9 |
| Thr | 15.8 | 6.3 |
| Ser | 20.7 | 8.2 |
| Glu + Gln | 35.0 | 13.8 |
| Pro | 9.5 | 3.8 |
| Gly | 16.0 | 6.3 |
| Ala | 4.2 | 1.7 |
| Cys | 32.3 | 12.8 |
| Val | 10.8 | 4.3 |
| Met | 1.1 | 0.4 |
| Ile | 7.0 | 2.8 |
| Leu | 20.2 | 8.0 |
| Tyr | 6.1 | 2.4 |
| Phe | 8.1 | 3.2 |
| His | 11.1 | 4.4 |
| Lys | 15.7 | 6.2 |
| Arg | 11.8 | 4.7 |
| Total | 252.9 | 100 |

A content of glucosamine was detected by amino acid analysis. The results of an affinoblot carried out using Concanavalin A and wheatgerm lectin also showed that TNF-BP is a glycoprotein.

The substantially homogeneous protein was digested with trypsin and the amino acid sequences of 17 of the cleavage peptides obtained were determined. The C-ending was also analyzed.

TNF-BP obviously has the function of a regulator of TNF activity with the ability to buffer the variations in concentration of free, biologically active TNF-α. TNF-BP should also affect the secretion of TNF by the kidneys because the complex formed with TNF, the molecular weight of which was measured at around 75,000 by gel permeation chromatography on Sephadex G 75, is obviously not retained by the glomerulus, unlike TNF. The TNF-BP was detected in the urine of dialysis patients as one of three main protein components which have an affinity for TNF and which are eluted together with TNF-BP from the TNF affinity chromatography column. However, the other two proteins obviously bind in a manner which does not affect the binding of TNF-α to its cell surface receptor.

The results obtained regarding the biological activity of TNF-BP, in particular the comparison of the binding constant with the binding constant described for the TNF receptor (Creasey, A. A., et al., *Proc. Natl. Acad. Sci.* 84:3293–3297 (1987)), provided a first indication that this protein might be the soluble part of a TNF receptor.

In view of its ability to inhibit the biological activity of TNF-α and TNF-β, the TNF binding protein is suitable for use in cases where a reduction in the TNF activity in the body is indicated. Functional derivatives or fragments of the TNF binding protein with the ability to inhibit the biological activity of TNF are also suitable for use in such cases.

Covalent modifications of the TNF binding proteins of the present invention are included within the scope of this invention. Variant TNF binding proteins may be conveniently prepared by in vitro synthesis. Such modifications may be introduced into the molecule by reacting targeted amino acid residues of the purified or crude protein with an organic derivatizing agent that is capable of reacting with selected side chains or terminal residues. The resulting covalent derivatives are useful in programs directed at identifying residues important for biological activity.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; 0-methylissurea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form 0-acetyl tyrosyl species and 3-nitro derivatives, respectively. Tyrosyl residues are iodinated using $^{125}I$ or $131_I$ to prepare labeled proteins for use in radioimmunoassay, the chloramine T method described above being suitable.

Carboxyl side groups (aspartyl or glutamyl) are selectively modified by reaction with carbodiimides (R'-N-C-N-R') such as 1-cyclohexyl-3-(2-morpholinyl-(4-ethyl) carbodiimide or 1-ethyl-3 (4 azonia 4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking the TNF binding proteins to water-insoluble support matrixes or surfaces for use in the method for cleaving TNF binding protein-fusion polypeptide to release and recover the cleaved polypeptide. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl) dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or theonyl residues, methylation of the α-amino groups of lysine, arginine, and histidine side chains (T. E. Creighton, *Proteins: Structure and Molecule Properties*, W.H. Freeman & Co., San Francisco, pp. 79–86 (1983)), acetylation of the N-terminal amine, and, in some instances, amidation of the C-terminal carboxyl groups.

Amino acid sequence variants of the TNF binding proteins can also be prepared by mutations in the DNA. Such variants include, for example, deletions from, or insertions or substitutions of, residues within the amino acid sequence shown in the Figures. Any combination of deletion, insertion, and substitution may also be made to arrive at the final construct, provided that the final construct possesses the desired activity (binding to TNF). Obviously, the mutations that will be made in the DNA encoding the variant must not place the sequence out of reading frame and preferably will not create complementary regions that could produce secondary mRNA structure (see EP Patent Application Publication No. 75,444).

At the genetic level, these variants ordinarily are prepared by site-directed mutagenesis of nucleotides in the DNA encoding the TNF binding proteins, thereby producing DNA encoding the variant, and thereafter expressing the DNA in recombinant cell culture. The variants typically exhibit the same qualitative biological activity as the naturally occurring analog.

While the site for introducing an amino acid sequence variation is predetermined, the mutation per se need not be predetermined. For example, to optimize the performance of a mutation at a given site, random mutagenesis may be conducted at the target codon or region and the expressed TNF binding protein variants screened for the optimal combination of desired activity. Techniques for making substitution mutations at predetermined sites in DNA having a known sequence are well known, for example, site-specific mutagenesis.

Preparation of a TNF binding protein variant in accordance herewith is preferably achieved by site-specific mutagenesis of DNA that encodes an earlier prepared variant or a nonvariant version of the protein. Site-specific mutagenesis allows the production of. TNF binding protein variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., *DNA* 2:183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira et al., *Meth. Enzymol.* 153:3 (1987)) may be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci. (USA)* 75:5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells such as JM101 cells and clones are selected that include recombinant vectors bearing the mutated sequence arrangement.

After such a clone is selected, the mutated protein region may be removed and placed in an appropriate vector for protein production, generally an expression vector of the type that may be employed for transformation of an appropriate host.

Amino acid sequence deletions may generally range from about 1 to 30 residues or 1 to 10 residues, and typically are contiguous.

Amino acid sequence insertions include amino and/or carboxyl-terminal fusions of from one residue to polypeptides of essentially unrestricted length, as well as intrasequence insertions of single or multiple amino acid residues. Intrasequence insertions (i.e., insertions within the complete hormone receptor molecule sequence) may range generally from about 1 to 10 or 1 to 5 residues. An example of a terminal insertion includes a fusion of a signal sequence, whether heterologous or homologous to the host cell, to the N-terminus of the TNF binding protein to facilitate the secretion of mature TNF binding protein from recombinant hosts.

The third group of variants are those in which at least one amino acid residue in the TNF binding protein, and preferably, only one, has been removed and a different residue inserted in its place. Such substitutions preferably are made in accordance with the following Table 1 when it is desired to modulate finely the characteristics of a hormone receptor molecule.

TABLE 1

| Original Residue | Exemplary Substitutions |
| --- | --- |
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in functional or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Most deletions and insertions, and substitutions in particular, are not expected to produce radical changes in the characteristics of the TNF binding protein. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the TNF binding protein-encoding nucleic acid, expression of the variant nucleic acid in recombinant cell culture, and, optionally, purification from the cell culture, for example, by immunoaffinity adsorption on a polyclonal anti-TNF binding protein column (to absorb the variant by binding it to at least one remaining immune epitope).

The activity of the cell lysate or purified TNF binding protein variant is then screened in a suitable screening assay for the desired characteristic. For example, a change in the binding affinity for TNF or immunological character of the TNF binding protein, such as affinity for a given antibody, is measured by a competitive type immunoassay. Changes in immunomodulation activity are measured by the appropriate assay. Modifications of such protein properties as redox or thermal stability, hydrophobicity, susceptibility to proteolytic degradation or the tendency to aggregate with carriers or into multimers are assayed by methods well known to the ordinarily skilled artisan.

TNF-BP (or the functional derivatives, variants, and active fragments thereof) may be used for the prophylactic and therapeutic treatment of the human or animal body in indications where TNF-α has a harmful effect. Such diseases include in particular inflammatory and infectious and parasitic diseases or states of shock in which endogenous TNF-α is released, as well as cachexia, GVHR, ARDS (Adult Respiratory Distress Symptom) and autoimmune diseases such as rheumatoid arthritis, etc. Also included are pathological conditions which may occur as side effects of treatment with TNF-α, particularly at high doses, such as severe hypotension or disorders of the central nervous system.

In view of its TNF binding properties, TNF-BP is also suitable as a diagnostic agent for determining TNF-α and/or TNF-β, e.g., as one of the components in radioimmunoassays or enzyme immunoassays, optionally together with antibodies against TNF.

In view of its properties, this protein is a pharmacologically useful active substance which cannot be obtained in sufficient quantities from natural sources using protein-chemical methods.

There was therefore a need to produce this protein (or related proteins with the ability to bind TNF) by recombinant methods in order that it could be made available in sufficient amounts for therapeutic use. The phrase "ability to bind TNF" within the scope of the present invention means the ability of a protein to bind to TNF-α in such a way that TNF-α is prevented from binding to the functional part of the receptor and the activity of TNF-α in humans or animals is inhibited or prevented altogether. This definition also includes the ability of a protein to bind to other proteins, e.g. to TNF-β, and inhibit their effect.

The aim of the present invention was to provide the DNA which codes for TNF-BP, in order to make it possible, on the basis of this DNA, to produce recombinant DNA molecules by means of which suitable host organisms can be transformed, with the intention of producing TNF-BP or functional derivatives and fragments thereof.

Within the scope of this objective, it was also necessary to establish whether TNF-BP is the soluble part of a TNF receptor. This assumption was confirmed, thus providing the basis for clarification of the receptor sequence.

Another objective within the scope of the present invention was to prepare the cDNA coding for a TNF receptor, for the purpose of producing recombinant human TNF receptor.

The presence of a specific receptor with a high affinity for TNF-α on various cell types was shown by a number of working groups. Recently, the isolation and preliminary characterization of a TNF-α receptor was reported for the first time (Stauber, G. B., et al., J. Biol. Chem. 263:19098–19104 (1988)). Since the binding of radioactively labelled TNF-α can be reversed by an excess of TNF-β (Aggarwal, B. B., et al., Nature 318:655–667 (1985)), it was proposed that TNF-α and TNF-β share a common receptor. On the other hand, since it was shown that certain cell types which respond to TNF-α are wholly or partly insensitive to TNF-β (Locksley, R. M., et al., J. Imunol. 139:1891–1895 (1987)), the existence of a common receptor was thrown into doubt again.

By contrast, recent results on the binding properties of TNF-β to receptors appear to confirm the theory of a common receptor (Stauber, G. B., et al., J. Biol. Chem. 264:3573–3576 (1989)), and this study proposes that there are differences between TNF-α and TNF-β in their interaction with the receptor or in addition with respect to the events which occur in the cell after the ligand-receptor interaction. Lately, there has been a report of another TNF-binding protein which is presumed to be the soluble form of a different TNF receptor (Engelmann et al., *J. Biol. Chem.* 265:1531–1536 (1990)). The availability of the DNA coding for a TNF receptor is the prerequisite for the production of recombinant receptor and consequently makes it much easier to carry out comparative investigations on different types of cell regarding their TNF-α and/or TNF-β receptors or the reactions triggered by the binding of TNF to the receptor in the cell. It also makes it possible to clarify the three-dimensional structure of the receptor and hence provide the prerequisite for a rational design for the development of agonists and antagonists for the TNF activity.

The efforts to solve the problem of the invention started from the finding that major difficulties are occasionally encountered when searching through cDNA libraries using hybridizing probes derived from amino acid sequences of short peptides, on account of the degeneration of the genetic code. In addition, this procedure is made more difficult when the researcher does not know in which tissue a particular protein, e.g. TNF-BP, is synthesized. In this case, should the method fail, it is not always possible to tell with any certainty whether the cause of the failure was the choice of an unsuitable cDNA library or the insufficient specificity of the hybridization probes.

Therefore, the following procedure was used according to the invention in order to obtain the DNA coding for TNF-BP:

The cDNA library used was a library of the fibrosarcoma cell line HS913 T which had been induced with TNFα and was present in λ gt11. In order to obtain λ DNA with TNF-BP sequences from this library, the high degree of sensitivity of the polymerase chain reaction (PCR (Saiki, R. K., *Science* 239:487–491 (1988))) was used. (Using this method it is possible to obtain, from an entire cDNA library, an unknown DNA sequence flanked by oligonucleotides which have been designed on the basis of known amino acid partial sequences and used as primers. A longer DNA fragment of this kind can subsequently be used as a hybridization probe, e.g. in order to isolate cDNA clones, particularly the original cDNA clone).

On the basis of the N-terminal amino acid sequence (main sequence) and amino acid sequences of tryptic peptides obtained from highly purified TNF-BP, hybridization probes were prepared. Using these probes, a cDNA which constitutes part of the cDNA coding for TNF-BP was obtained by PCR from the cDNA library HS913T.

This cDNA has the following nucleotide sequence:

CAG GGG AAA TAT ATT CAC CCT CAA AAT AAT TCG ATT TGC

TGT ACC AAG TGC CAC AAA GGA ACC TAC TTG TAC AAT GAC

TGT CCA GGC CCG GGG CAG GAT ACG GAC TGC AGG GAG TGT

GAG AGC GGC TTC TTC ACA GCC TCA GAA AAC AAC AAG.

This DNA is one of a number of possible variants which are suitable for hybridizing with TNF-BP DNAs or TNF-BP-RNAs (these variants include for example those DNA molecules which are obtained by PCR amplification with the aid of primers, wherein the nucleotide sequence does not coincide precisely with the desired sequence, possibly as a result of restriction sites provided for cloning purposes or because of amino acids which were not clearly identified in the amino acid sequence analysis). "TNF-BP-DNAs" and "TNF-BP-RNAs" indicate nucleic acids which code for TNF-BP or related proteins with the ability to bind TNF or which contain a sequence coding for such a protein.

TNF-BP-DNAs (or TNF-BP-RNAs) also include cDNAs derived from mRNAs which are formed by alternative splicing (or these mRNAs themselves). The phrase "alternative splicing" means the removal of introns, using splice acceptor and/or splice donor sites which are different from the same mRNA precursor. The mRNAs thus formed differ from one another by the total or partial presence or absence of certain exon sequences, and in some cases there may be a shift in the reading frame.

The cDNA (or variants thereof) initially obtained according to the invention, containing some of the sequence coding for TNF-BP, can thus be used as a hybridization probe in order to obtain cDNA clones containing TNF-BP DNAs from cDNA libraries. It may also be used as a hybridization probe for mRNA preparations, for isolating TNF-BP RNAs and for producing concentrated cDNA libraries therefrom, for example, to allow much simpler and more efficient screening. A further field of application is the isolation of the desired DNAs from genomic DNA libraries using these DNAs as hybridization probes.

The DNA defined hereinbefore (or a variant thereof) is capable of hybridizing with DNAs (or RNAs) which code for TNF-BP or contain the sequence which codes for TNF-BP. Using this DNA as probe, it is also possible to obtain cDNAs which code for proteins, the processing of which yields TNF-BP. The term "processing" means the splitting off of partial sequences in vivo. This might mean, at the N-terminus the signal sequence and/or other sequences and possibly also at the C-terminus, the transmembrane and cytoplasmic region of the receptor. Using this hybridization signal it is therefore possible to search through suitable cDNA libraries to look for any cDNA which contains the entire sequence coding for a TNF receptor (if necessary, this operation may be carried out in several steps).

According to the invention, the cDNA of the sequence defined hereinbefore, which had been obtained by PCR from the cDNA library of the TNF-α induced fibrosarcoma cell line HS913 T (in λ gt11), was used to search through the cDNA library once more, the lambda DNA was excised from the hybridizing clones, subcloned and sequenced. A 1334 base long cDNA insert was obtained which contains the sequence coding for TNF-BP.

Thus, first of all DNAs were prepared, coding for a polypeptide capable of binding TNF, or for a polypeptide in which this TNF binding protein is a partial sequence. These DNAs also include DNAs of the kind which code for parts of these polypeptides.

The complete nucleotide sequence of the longest c D N A insert obtained is shown in FIG. 1.

This nucleotide sequence has a continuous open reading frame beginning with base 213 up to the end of the 1334 bp long cDNA insert. Since there is a stop codon (TAG) in the same reading frame 4 codons before the potential translation start codon ATG (213–215), it was assumed that the start codon is actually the start of translation used in vivo.

A comparison of the amino acid sequence derived from the nucleotide sequence with the amino acid sequences determined from the amino terminal end of TNF-BP and tryptic peptides, shows a high degree of conformity. This means that the isolated cDNA contains the sequence coding for authentic TNF-BP.

Starting from the N-terminus, the first sequence which shows conformity with a tryptic cleavage peptide sequence is the sequence from fraction 12 (Leu-Val-Pro-. . .), which had also been obtained as a subsidiary sequence in the analysis of the N-terminus of TNF-BP. This N-terminal leucine corresponds to the 30th amino acid in the cDNA sequence. Since the preceding section of 29 amino acids has a strongly hydrophobic nature and TNF-BP is a secreted protein, it can be concluded that these 29 amino acids constitute the signal peptide required for the secretion process, which is split off during secretion (designated S1-S29 in FIG. 1). The amino acid sequence obtained as the main sequence in the N-terminal analysis of TNF-BP corresponds to the amino acids beginning with Asp-12 in the cDNA sequence. This aspartic acid group directly follows the basic dipeptide Lys-Arg. Since a very large number of proteins are cleaved proteolytically in vivo after this dipeptide, it can be assumed that TNF-BP with N-terminal Asp is not formed directly by the processing of a precursor in the secretion process, but that the N-terminal 11 amino acids are split off from the processed protein at a later time by extracellular proteases. The carboxyterminal end of TNF-BP had been determined as Ile-Glu-Asn (C-terminal analysis; tryptic peptide fraction 27: amino acids 159–172, tryptic peptide fraction 21: amino acids 165–172), Asn corresponding to position 172 in the cDNA sequence.

Potential N-glycosylation sites of general formula Asn-Xaa-Ser/Thr, in which Xaa may be any amino acid other than proline, are located at positions 25–27 (Asn-Asn-Ser), 116–118 (Asn-Cys-Ser) and 122–124 (Asn-Gly-Thr) of the TNF-BP cDNA sequence. (The fact that Asn-25 is glycosylated is clear from the fact that Asn could not be identified in the sequencing of the corresponding tryptic cleavage peptide at this site.)

Analysis of the nucleotide sequence or the amino acid sequence derived therefrom in conjunction with the protein-chemical investigations carried out shows that TNF-BP is a glycosylated polypeptide with 172 amino acids, which is converted by proteolytic cleaving after the 11th amino acid into a glycoprotein with 161 amino acids. The following Table shows the tryptic peptides sequenced and the corresponding amino acid sequences derived from the cDNA sequence:

| Fraction | Amino acids | |
|---|---|---|
| 12 | 1–8 | |
| 1 | 12–19 | |
| 8 | 20–32 | |
| 14/I | 36–48 | |
| 20 | 36–53 | |
| 11 | 54–67 | (Amino acids 66–67 had not been correctly determined on the peptide) |
| 14/II | 79–91 | |
| 26 | 133–146 | |
| 5 | 147–158 | |
| 27 | 159–172 | |

The cDNA obtained is the prerequisite for the preparation of recombinant TNF-BP.

As already mentioned, the cDNA initially isolated according to the invention does not contain the stop codon which could have been expected from analysis of the C-terminus after the codon for Asn-172, but the open reading frame is continued. The region between Val-183 and Met-204 is strongly hydrophobic by nature. This hydrophobic region of 22 amino acids followed by a portion containing positively charged amino acids (Arg-206, Arg-209) has the typical features of a transmembrane domain which anchors proteins in the cell membrane. The protein fraction following in the C-terminus direction on the other hand is strongly hydrophilic.

The hydrophobicity profile is shown in FIG. 2 (the hydrophobicity plot was produced using the Mac Molly program (made by Soft Gene Berlin); the window size for calculating the values was 11 amino acids. Hydrophobic regions correspond to positive values and hydrophilic regions to negative values on the ordinates. The abscissa shows the number of amino acids beginning with the start methionine S1).

The protein structure shows that the DNA coding for the soluble TNF-BP secreted is part of a DNA coding for a larger protein: this protein has the feature of a protein anchored in the cell membrane, contains TNF-BP in a manner typical of extracellular domains and has a substantial portion which is typical of cytoplasmatic domains. Soluble TNF-BP is obviously obtained from this membrane-bound form by proteolytic cleaving just outside the transmembrane domain.

The structure of the protein coded by the cDNA obtained in conjunction with the ability of TNF-BP to bind TNF confirms the assumption that TNF-BP is part of a cellular surface receptor for TNF the extracellular domains of which, responsible for the binding of TNF, can be cleaved proteolytically and retrieved in the form of the soluble TNF-BP. (The possibility should not be ruled out that, with regard to the operating capacity of the receptor, this protein may possibly be associated with one or more other proteins).

For the purposes of the production of TNF-BP on a larger scale, it is advantageous not to start from the whole cDNA, since the need to cleave TNF-BP from that part of the protein which represents the membrane-bound part of the TNF receptor must be borne in mind. Rather, as mentioned hereinbefore, a translation stop codon is expediently inserted after the codon for Asn-172 by controlled mutagenesis in order to prevent protein synthesis going beyond the C-terminal end of TNF-BP. With the cDNA which is initially obtained according to the invention and which represents a partial sequence of the DNA coding for a TNF receptor, it is possible to obtain the complete receptor sequence by amplifying the missing 3'-end, e.g. by means of modified PCR (RACE="rapid amplification of cDNA ends" (Frohman, M. A., et al., Proc. Natl. Acad. Sci. 85:8998–9002 (1988)), with the aid of a primer constructed on the basis of a sequence located as far as possible in the direction of the 3'-end of the cDNA present. An alternative method is the conventional screening of the cDNA library with the available cDNA or parts thereof as probe.

According to the invention, first of all the rat TNF receptor cDNA was isolated and with a partial sequence therefrom the complete human TNF receptor cDNA was obtained and brought to expression.

The invention relates to a human TNF receptor and the DNA coding for it. This definition also includes DNAs which code for C- and/or N-terminally shortened, e.g. processed forms or for modified forms (e.g. by changes at proteolytic cleavage sites, glycosylation sites or specific domain regions) or for fragments, e.g. the various domains, of the TNF receptor. These DNAs may be used in conjunction with the control sequences needed for expression as a constituent of recombinant DNA molecules, to which the present invention also relates, for transforming prokaryotic or eukaryotic host organisms. On the one hand this creates the prerequisite for preparing the TNF receptor or modifications or fragments thereof in larger quantities by the recombinant method, in order to make it possible for example to clarify the three-dimensional structure of the receptor. On the other hand, these DNAs can be used to transform higher eukaryotic cells in order to allow a study of the mechanisms and dynamics of the TNF/receptor interaction, signal transmission or the relevance of the various receptor domains or sections thereof.

The present invention encompasses the expression of the desired TNF binding protein in either prokaryotic or eukaryotic cells. Preferred eukaryotic hosts include yeast (especially Saccharomyces), fungi (especially Aspergillus), mammalian cells (such as, for example, human or primate cells) either in vivo, or in tissue culture.

Yeast and mammalian cells are preferred hosts of the present invention. The use of such hosts provides substantial advantages in that they can also carry out post-translational peptide modifications including glycosylation. A number of recombinant DNA strategies exist which utilize strong promoter sequences and high copy number of plasmids which can be utilized for production of the desired proteins in these hosts.

Yeast recognize leader sequences on cloned mammalian gene products and secrete peptides bearing leader sequences (i.e., pre-peptides). Mammalian cells provide post-translational modifications to protein molecules including correct folding or glycosylation at correct sites.

Mammalian cells which may be useful as hosts include cells of fibroblast origin such as VERO or CHO-K1, and their derivatives. For a mammalian host, several possible vector systems are available for the expression of the desired TNF binding protein. A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene which has a high level of expression. Alternatively, promoters from mammalian expression products, such as actin, collagen, myosin, etc., may be employed. Transcriptional initiation regulatory signals may be selected which allow for repression or activation, so that expression of the genes can be modulated. Of interest are regulatory signals which are temperature-sensitive so that by varying the temperature, expression can be repressed or initiated, or are subject to chemical regulation, e.g., metabolite.

The expression of the desired TNF binding protein in eukaryotic hosts requires the use of eukaryotic regulatory regions. Such regions will, in general, include a promoter region sufficient to direct the initiation of RNA synthesis. Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature (London)* 290:304–310 (1981)); the yeast gal4 gene promoter (Johnston, S. A., et al., *Proc. Natl. Acad. Sci. (USA)* 79:6971–6975 (1982); Silver, P. A., et al., *Proc. Natl. Acad. Sci. (USA)* 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes the desired receptor molecule does not contain any intervening codons which are capable of encoding a methionine (i.e., AUG). The presence of such codons results either in the formation of a fusion protein (if the AUG codon is in the same reading frame as the desired receptor molecule encoding DNA sequence) or a frame-shift mutation (if the AUG codon is not in the same reading frame as the desired TNF binding protein encoding sequence).

The expression of the TNF binding proteins can also be accomplished in procaryotic cells. Preferred prokaryotic hosts include bacteria such as *E. coli*, Bacillus, Streptomyces, Pseudomonas, Salmonella, Serratia, etc. The most preferred prokaryotic host is *E. coli*. Bacterial hosts of particular interest include *E coli* K12 strain 294 (ATCC 31446), *E. coli* X1776 (ATCC 31537), *E. coli* W3110 (F⁻, lambda⁻, prototrophic (ATCC 27325)), and other enterobacteria (such as *Salmonella typhimurium* or *Serratia marcescens*), and various Pseudomonas species. The prokaryotic host must be compatible with the replicon and control sequences in the expression plasmid.

To express the desired TNF binding protein in a prokaryotic cell (such as, for example, *E. coli, B. subtilis,* Pseudomonas, Streptomyces, etc.), it is necessary to operably link the desired receptor molecule encoding sequence to a functional prokaryotic promoter. Such promoters may be either constitutive or, more preferably, regulatable (i.e., inducible or derepressible). Examples of constitutive promoters include the int promoter of bacteriophage λ, and the bla promoter of the β-lactamase gene of pBR322, etc. Examples of inducible prokaryotic promoters include the major right and left promoters of bacteriophage λ ($P_L$ and $P_R$), the trp, recA, lacZ, lacI, gal, and tac promoters of *E. coli*, the α-amylase (Ulmanen, I., et al., *J. Bacteriol.* 162:176–182 (1985)), the σ-28-specific promoters of *B. subtilis* (Gilman, M. Z., et al., *Gene* 32:11–20 (1984)), the promoters of the bacteriophages of Bacillus (Gryczan, T. J., In: *The Molecular Biology of the Bacilli*, Academic Press, Inc., N.Y. (1982)), and *Streptomyces* promoters (Ward, J. M., et al., *Mol. Gen. Genet.* 203:468–478 (1986)). Prokaryotic promoters are reviewed by Glick, B. R., (*J. Ind. Microbiol.* 1:277–282 (1987)); Cenatiempo, Y. (*Biochimie* 68:505–516 (1986)); and Gottesman, S. (*Ann. Rev. Genet.* 18:415–442 (1984)).

Proper expression in a prokaryotic cell also requires the presence of a ribosome binding site upstream from the gene-encoding sequence. Such ribosome binding sites are disclosed, for example, by Gold, L., et al. (*Ann. Rev. Microbiol.* 35:365–404 (1981)).

The desired TNF binding protein encoding sequence and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the desired receptor molecule may occur through the transient expression of the introduced sequence. Alternatively, permanent expression may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may complement an auxotrophy in the host (such as leu2, or ura3, which are common yeast auxotrophic markers), biocide resistance, e.g., antibiotics, or heavy metals, such as copper, or the like. The selectable marker gene can either be directly linked to the DNA gene sequences to be expressed, or introduced into the same cell by co-transfection.

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Any of a series of yeast gene expression systems can be utilized. Examples of such expression vectors include the yeast 2-micron circle, the expression plasmids YEP13, YCP and YRP, etc., or their derivatives. Such plasmids are well known in the art (Botstein, D., et al., *Miami Wntr. Symp.* 19:265–274 (1982); Broach, J. R., In: *The Molecular Biology of the Yeast Saccharomyces: Life Cycle and Inheritance*, Cold Spring Harbor Laboratory, Cold Spring Harbor, N.Y., p. 445–470 (1981); Broach, J. R., *Cell* 28:203–204 (1982)).

For a mammalian host, several possible vector systems are available for expression. One class of vectors utilize DNA elements which provide autonomously replicating extra-chromosomal plasmids, derived from animal viruses such as bovine papilloma virus, polyoma virus, adenovirus, or SV40 virus. A second class of vectors relies upon the integration of the desired gene sequences into the host chromosome. Cells which have stably integrated the introduced DNA into their chromosomes may be selected by also introducing one or more markers which allow selection of host cells which contain the expression vector. The marker may provide for prototropy to an auxotrophic host, biocide resistance, e.g., antibiotics, or heavy metals, such as copper or the like. The selectable marker gene can either be directly linked to the DNA sequences to be expressed, or introduced into the same cell by co-transformation. Additional elements may also be needed for optimal synthesis of mRNA. These elements may include splice signals, as well as transcription promoters, enhancers, and termination signals. The cDNA expression vectors incorporating such elements include those described by Okayama, H., *Mol. Cell. Biol.* 3:280 (1983), and others.

Preferred prokaryotic vectors include plasmids such as those capable of replication in *E. coli* such as, for example, pBR322, ColE1, pSC101, pACYC 184, πVX. Such plasmids are, for example, disclosed by Maniatis, T., et al. (In: *Molecular Cloning, A Laboratory Manual*, Cold Spring Harbor Press, Cold Spring Harbor, N.Y. (1982)). Bacillus plasmids include pC194, pC221, pT127, etc. Such plasmids are disclosed by Gryczan, T. (In: *The Molecular Biology of the Bacilli*, Academic Press, N.Y. (1982), pp. 307–329). Suitable Streptomyces plasmids include pIJ101 (Kendall, K. J., et al., *J. Bacteriol.* 169:4177–4183 (1987)), and Streptomyces bacteriophages such as ϕC31 (Chater, K. F., et al., In: *Sixth International Symposium on Actinomycetales Biology*, Akademiai Kaido, Budapest, Hungary (1986), pp. 45–54). Pseudomonas plasmids are reviewed by John, J. F., et al. (*Rev. Infect. Dis.* 8:693–704 (1986)), and Izaki, K. (*Jpn. J. Bacteriol.* 33:729–742 (1978)).

Once the vector or DNA sequence containing the constructs has been prepared for expression, the DNA constructs may be introduced into an appropriate host. Various techniques may be employed, such as protoplast fusion, calcium phosphate precipitation, electroporation or other conventional techniques. After the fusion, the cells are grown in media and screened for appropriate activities. Expression of the sequence results in the production of the TNF binding protein.

The TNF binding proteins of the invention may be isolated and purified from the above-described recombinant molecules in accordance with conventional methods, such as extraction, precipitation, chromatography, affinity chromatography, electrophoresis, or the like. By the term "substantially pure" is intended TNF binding proteins which are substantially one major band by SDS-PAGE polyacrylamide electrophoresis and which contain only minor amounts of other proteins which would normally contaminate a whole cell lysate containing native TNF receptor protein, as evidenced by the presence of other minor bands.

The recombinant TNF receptor (or fragments or functional derivatives thereof) can be used to investigate substances for their interaction with TNF or the TNF receptor or their influence on the signal transmission induced by TNF. Such screenings (using proteins/fragments/variants or suitably transformed higher eukaryotic cells) create the prerequisite for the identification of substances which substitute TNF, inhibit the bonding thereof to the receptor or those which are capable of blocking or intensifying the mechanism of signal transmission initiated by TNF.

One possible method of discovering agonists and antagonists of TNF or the TNF receptor is in the establishment of high capacity screening. A suitable cell line, preferably one which does not express endogenous human TNF receptor, is transformed with a vector which contains the DNA coding for a functional TNF receptor and optionally modified from the natural sequence. The activity of agonists or antagonists can be investigated in screening of this kind by monitoring the response to the interaction of the substance with the receptor using a suitable reporter (altered enzyme activity, e.g. protein kinase C, or gene activation, e.g. manganese superoxide dismutase, NF-KB). Investigations into the mechanisms and dynamics of the TNF/receptor interaction, signal transmission or the role of the receptor domains in this respect may also be carried out, for example, by combining DNA fractions coding for the extracellular domain of the TNF receptor (or parts thereof) with DNA fractions coding for various transmembrane domains and/or various cytoplasmatic domains and bringing them to expression in eukaryotic cells. The hybrid expression products which may be obtained in this way may be capable of giving conclusive information as to the relevance of the various receptor domains, on the basis of any changes in the properties for signal transduction, so that targeted screening is made easier.

The availability of the cDNA coding for the TNF receptor or fractions thereof is the prerequisite for obtaining the genomic DNA. Under stringent conditions, a DNA library is screened and the clones obtained are investigated to see whether they contain the regulatory sequence elements needed for gene expression in addition to the coding regions (e.g. checking for promoter function by fusion with coding regions of suitable reporter genes). Methods for screening DNA libraries under stringent conditions are taught, for example, in EPA 0 174 143, incorporated by reference herein. Obtaining the genomic DNA sequence makes it possible to investigate the regulatory sequences situated in the area which does not code for the TNF receptor, particularly in the 5'-flanking region, for any possible interaction with known substances which modulate gene expression, e.g. transcription factors or steroids, or possibly discover new substances which might have a specific effect on the expression of this gene. The results of such investigations provide the basis for the targeted use of such substances for modulating TNF receptor expression and hence for directly influencing the ability of the cells to interact with TNF. As a result, the specific reaction with the ligands and the resulting effects can be suppressed.

The scope of the present invention also includes DNAs which code for subtypes of the TNF receptor or its soluble forms, which may possibly have properties different from those of the present TNF receptor. These are expression products which are formed by alternative splicing and have modified structures in certain areas, e.g. structures which can bring about a change in the affinity and specificity for the ligand (TNF-α/TNF-β) or a change in terms of the nature and efficiency of signal transmission.

With the aid of the cDNA coding for the TNF receptor it is possible to obtain nucleic acids which hybridize with the cDNA or fragments thereof under conditions of low stringency and code for a polypeptide capable of binding TNF or contain the sequence coding for such a polypeptide.

According to a further aspect the invention relates to recombinant TNF-BP, preferably in a secretable form, which constitutes the soluble part of the TNF receptor according to the invention, and the DNA coding for it. By introducing a DNA construct containing the sequence coding for TNF-BP with a sequence coding for a signal peptide under the control of a suitable promoter into suitable host organisms, especially eukaryotic and preferably higher eukaryotic cells, it is possible to produce TNF-BP which is secreted into the cell supernatant.

If a signal peptide is used with regard to the secretion of the protein, the DNA coding for the signal peptide is conveniently inserted before the codon for Asp-12 in order to obtain a uniform product. Theoretically, any signal peptide is suitable which guarantees secretion of the mature protein in the corresponding host organism. If necessary, the signal sequence can also be placed in front of the triplet coding for Leu-1; in this case, it may be necessary to separate the form of TNF-BP produced by splitting off the peptide which consists of 11 amino acids at the N-terminus, from the unprocessed or incompletely processed TNF-BP in an additional purification step.

Since the cDNA after the codon for Asn-172, which represents the C-terminus on the basis of C-terminal analysis, does not contain a stop codon, a translation stop codon is expediently introduced, with respect to the expression of TNF-BP, after the codon for Asn-172, by controlled mutagenesis.

The DNA coding for TNF-BP can be modified by mutation, transposition, deletion, addition or truncation provided that DNAs modified in this way code for (poly) peptides capable of binding TNF. Such modifications may consist, for example, of changing one or more of the potential glycosylation sites which are not necessary for the biological activity, e.g. by replacing the Asn codon by a triplet which codes for a different amino acid. With a view to maintaining the biological activity, modifications which result in a change in the disulfide bridges (e.g. a reduction in their number) may also be carried out.

The DNA molecules referred to thus constitute the prerequisite for constructing recombinant DNA molecules, which are also an object of the invention. With recombinant DNA molecules of this kind in the form of expression vectors containing the DNA, optionally suitably modified, which codes for a protein with TNF-BP activity, preferably with a preceding signal sequence, and the control sequences needed for expression of the protein, it is possible to transform and cultivate suitable host organisms and obtain the protein.

Just like any modifications to the DNA sequence, host cells or organisms suitable for expression are selected particularly with regard to the biological activity of the protein in binding TNF. Furthermore, the criteria which are conventionally applied to the preparation of recombinant proteins such as compatibility with the chosen vector, processability, isolation of the protein, expression characteristics, safety and cost aspects are involved in the decision as to the host organism. The choice of a suitable vector arises from the host intended for transformation. In principle, all vectors which replicate and express the DNAs (or modifications thereof) coding for TNF-BP according to the invention are suitable.

With respect to the biological activity of the protein, in the expression of the DNA coding for TNF-BP, particular account should be taken of any relevance of the criteria, found in the natural protein, of glycosylation and a high proportion of cysteine groups to the property of binding TNF. Conveniently, therefore, eukaryotes, particularly suitable expression systems of higher eukaryotes, are used for the expression.

Within the scope of the present invention, both transient and permanent expression of TNF-BP were demonstrated in eukaryotic cells.

The recombinant TNF-BP according to the invention and suitable modifications thereof which have the capacity to bind TNF can be used in the prophylactic and therapeutic treatment of humans and animals for indications in which a harmful effect of TNFα occurs. Since TNF-BP has also been shown to have a TNF-β inhibiting activity, it (or the associated or modified polypeptides) can be used in suitable doses, possibly in a form modified to give a greater affinity for TNF-β, to inhibit the effect of TNF-β in the body.

The invention therefore also relates to pharmaceutical preparations containing a quantity of recombinant TNF-BP which effectively inhibits the biological activity of TNF-α and/or TNF-β, or a related polypeptide capable of binding TNF.

Pharmaceutical preparations are particularly suitable for parenteral administration for those indications in which TNF displays a harmful effect, e.g. in the form of lyophilized preparations or solutions. These contain TNF-BP or a therapeutically active functional derivative thereof in a therapeutically active amount, optionally together with physiologically acceptable additives such as stabilizers, buffers, preservatives, etc.

The dosage depends particularly on the indication and the specific form of administration, e.g. whether it is administered locally or systemically. The size of the individual doses will be determined on the basis of an individual assessment of the particular illness, taking into. account such factors as the patient's general health, anamnesis, age, weight, sex, etc. It is essential when determining the therapeutically effective dose to take into account the quantity of TNF secreted which is responsible for the disease as well as the quantity of endogenous TNF-BP. Basically, it can be assumed that, for effective treatment of a disease triggered by TNF, at least the same molar amount of TNF-BP is required as the quantity of TNF secreted, and possibly a multiple excess might be needed.

More specifically, the objective of the invention is achieved as follows:

The N-terminal amino acid sequence of the highly purified TNF-BP and the amino acid sequences of peptides obtained by tryptic digestion of the protein were determined. Moreover, the C-terminus was determined by carboxypeptidase P digestion, derivatization of the amino acids split off and chromatographic separation. From the peptide sequences obtained by tryptic digestion, with a view to their use in PCR for the preparation of oligonucleotides, regions were selected from the N-terminus on the one hand and from a tryptic peptide on the other hand such that the complexity of mixed oligonucleotides for hybridization with cDNA is kept to a minimum. A set of mixed oligonucleotides were prepared on the basis of these two regions, the set derived from the region located at the N-terminus being synthesized in accordance with mRNA, whilst the set derived from the tryptic peptide was synthesized in reverse, so as to be complementary to the mRNA. In order to facilitate the subsequent cloning of a segment amplified with PCR, the set of oligonucleotides derived from the tryptic peptide was given a BamHI restriction site. Then λ DNA was isolated from the TNF-α induced fibrosarcoma cDNA library and from this a TNF-BP sequence was amplified using PCR. The resulting fragment was cloned and sequenced; it comprises 158 nucleotides and contains the sequence coding for the tryptic peptide 20 between the two fragments of sequence originating from the primer oligonucleotides.

This DNA fragment was subsequently radioactively labelled and used as a probe for isolating cDNA clones from the fibrosarcoma library. The procedure involved first hybridizing plaques with the probe, separating phages from hybridizing plaques and obtaining λ DNA therefrom. Individual cDNA clones were subcloned and sequenced; two of the characterized clones contained the sequence coding for TNF-BP.

This sequence constitutes part of the sequence coding for a TNF receptor.

After shortening of the 5'-non-coding region and insertion of a stop codon after the codon for the C-terminal amino acid of the natural TNF-BP, the cDNA was inserted in a suitable expression plasmid, eukaryotic cells were transformed therewith and the expression of TNF-BP was demonstrated using ELISA. The still outstanding 3'-region of the TNF receptor was obtained by searching through a rat brain cDNA library from the rat glia tumour cell line C6 using a TNF-BP probe and isolating all the cDNA coding for the rat TNF receptor.

The fraction of this cDNA at the 3'-end, which was assumed to correspond to the missing 3'-region behind the EcoRI cutting site of the human TNF receptor, was used as a probe to search through the HS913T cDNA library once more. A clone was obtained which contains all the DNA coding for the TNF receptor.

After shortening of the 5'-non-coding region, the cDNA was inserted in an expression plasmid and the expression of human TNF receptor was demonstrated in eukaryotic cells by means of the binding of radioactively labelled TNF.

Northern blot analysis confirmed that the isolated cDNA corresponds substantially to all the TNF-R mRNA (the slight discrepancy arises from the absence of part of the 5'-non-coding region). From this it can be concluded that the expressed protein is the complete TNF receptor.

The invention is illustrated by means of the Examples which follow.

EXAMPLE 1
Preparation of Highly Purified TNF-BP
 a) Concentration of urine
 200 liters of dialyzed urine from uraemia patients, stored in flasks containing EDTA (10 g/l), Tris (6 g/l), NaN$_3$ (1 g/l) and benzamidine hydrochloride (1 g/l) and kept in a refrigerator were concentrated by ultrafiltration using a highly permeable haemocapillary filter with an asymmetric hollow fibre membrane (FH 88H, Gambro) down to 4.2 liters with a protein content of 567 g. The concentrated urine was dialyzed against 10 mM/l Tris HCl, pH 8. During this procedure, as in the following steps (except reverse phase chromatography), 1 mM/l of benzamidine hydrochloride were added in order to counteract proteolytic digestion. Unless otherwise stated, all the subsequent purification steps were carried out at 4° C.

b) Ion exchange chromatography
 This step was carried out by charging DEAE Sephacel columns (2.5×40 cm) with samples of concentrated and dialyzed urine containing about 75 g of protein. Elution was carried out with 800 ml of an NaCl/10 mM Tris/HCl pH 8 gradient, the NaCl concentration being 0 to 0.4 M. The fractions from seven columns contain the TNF-BP with a total protein content of 114 g were stored at −20° C.

c) Affinity chromatography
 In order to prepare the TNF Sepharose column, rTNF-α (15 mg) in 0.1 M NaHCO3, 1 M NaCl, pH 9 (coupling buffer) was coupled to 1.5 g of cyanogen bromide-activated Sepharose 4B (Pharmacia). The Sepharose was swelled in 1 mM HCl and washed with coupling buffer. After the addition of rTNF-α the suspension was left to rotate for 2 hours at ambient temperature. The excess CNBr groups were blocked by rotation for one and a half hours with 1M ethanolamine, pH 8. The TNF Sepharose was washed a few times alternately in 1M NaCl, 0.1 M sodium acetate pH 8 and 1 M NaCl, 0.1 M boric acid pH 4 and then stored in phosphate-buffered saline solution with 1 mM benzamidine hydrochloride. The fractions obtained from step b) were adjusted to a concentration of 0.2 M NaCl, 10 mM Tris/HCl, pH 8. The TNF-Sepharose was packed into a column and washed with 0.2 M NaCl, 10 mM Tris HCl, pH 8 and the TNF-BP-containing fractions, corresponding to about 30 g of protein, were applied at a throughflow rate of 10 ml/h and washed exhaustively with 0.2 M NaCl, 10 mM Tris HCl, pH 8, until no further absorption could be detected in the eluate at 280 nm. Then TNF-BP was eluted with 0.2 M glycine/HCl, pH 2.5. TNF-BP-containing fractions from 4 separations were combined and lyophilized after the addition of polyethylene glycol (MW 6000) up to a final concentration of 10 mg/ml. The lyophilized sample was dissolved in distilled water and dialyzed against distilled water. (The dialyzed sample (4 ml) was stored in deep-frozen state).

This purification step further concentrated the product by about 9000 times compared with the previous product. SDS-PAGE (carried out as described in preliminary test 2) of the TNF-BP containing fractions showed the elution of three main components with molecular weights of 28,000, 30,000 and 50,000.

d) Reverse Phase Chromatography
 An aliquot amount (1 ml) of the fractions obtained from step c) with the addition of 0.1% trifluoroacetic acid was applied to a ProRPC HR 5/10 column (Pharmacia), connected to an FPLC system (Pharmacia). The column was equilibrated with 0.1% trifluoroacetic acid and charged at ambient temperature with a linear 15 ml gradient of 10 vol % to 50 vol % acetonitrile containing 0.1% trifluoroacetic acid; the through-flow rate was 0.3 ml/min. Fractions of 0.5 ml were collected and the absorption at 280 nm was determined, as well as the activity of the TNF-α binding protein, using the competitive binding test as described in Example 5, using 0.01 μl of sample in each case. TNF-BP eluted as a single activity peak corresponding to a sharp UV absorption peak.

This last purification step brought an increase in specific activity of about 29 fold, whilst the total increase in activity compared with the starting material (concentrated dialysis urine) was about 1.1×106-fold. SDS-PAGE of the reduced and non-reduced samples, carried out as described in preliminary test 2, resulted in a diffuse band, indicating the presence of a single polypeptide with a molecular weight of about 30,000. The diffused appearance of the band may be due to the presence of one of more heterogeneous glycosylations and/or a second polypeptide present in a smaller amount. The assumption that it might be a polypeptide with the N-terminus found to be a secondary sequence in preliminary test 3d), which is longer than TNF-BP at the end terminus, was confirmed by the sequence of the cDNA, according to which there is a fraction of 11 amino acids between the signal sequence and Asn (position 12), the sequence of which coincides with the N-terminal secondary sequence and which is obviously split off from the processed protein.

EXAMPLE 2
SDS Polyacrylamide Gel Electrophoresis (SDS-PAGE)

SDS-PAGE was carried out using the method of Laemmli (Laemmli, U. K., *Nature* 227:680–4 (1970)) on flat gels measuring 18 cm long, 16 cm wide and 1.5 mm thick, with 10 pockets, by means of an LKB 2001 electrophoresis unit. The protein content of the samples from the purification steps c) and d) (preliminary test 1) was determined by Bio-Rad Protein Assay or calculated from the absorption at 280 nm, an absorption of 1.0 being recognized to be equivalent to a content of 1 mg TNF-BP/ml.

The samples containing about 25 $\mu$g of protein (from preliminary test 1c) or about 5 $\mu$g (from 1d) in reduced form (β-mercaptoethanol) and non-reduced form, were applied to a 3% collecting gel and a 5 to 20% linear polyacrylamide gradient gel. Electrophoresis was carried out at 25 mA/gel without cooling. The molecular weight markers used (Pharmacia) were phosphorylase B (MW 94,000), bovine serum albumin (MW 67,000), ovalbumin (MW 43,000), carboanhydrase (MW 30,000), soya bean trypsin inhibitor (MW 20,100) and a-lactalbumin (MW 14,400). The gels were stained with Coomassie Blue in 7% acetic acid/40% ethanol and decolorized in 7% acetic acid/25% ethanol.

The results of the SDS-PAGE showed TNF-BP to be a polypeptide chain with a molecular weight of about 30,000.

EXAMPLE 3 a) Preparation of samples

15 $\mu$g of the protein purified according to preliminary test 1d) were desalinated using reverse phase HPLC and further purified. To do this a Bakerbond WP C18 column was used (Baker; 4.6×250 mm) and 0.1% trifluoroacetic acid in water (eluant A) or in acetonitrile (eluant B) as the mobile phase. The increase in the gradient was 20 to 68% eluant B in 24 minutes. Detection was carried out in parallel at 214 nm and 280 nm. The fraction containing TNF-BP was collected, dried and dissolved in 75 $\mu$l of 70% formic acid and used directly for the amino acid sequence analysis.

b) Amino acid sequence analysis

The automatic amino acid sequence analysis was carried out with an Applied Biosystems 477 A liquid phase sequenator by on-line determination of the phenylthiohydantoin derivatives released, using an Applied Biosystems Analyser, Model 120 A PTH. It gave the following N-terminal sequence as the main sequence (about 80% of the quantity of protein): Asp-Ser-Val-Xaa-Pro-Gln-Gly-Lys-Tyr-Ile-His-Pro-Gln-. In addition, the following secondary sequence was detected: Leu-(Val)-(Pro)-(His)-Leu-Gly-Xaa-Arg-Glu-. (The amino acids shown in brackets could not be clearly identified.)

EXAMPLE 4
SDS-PAGE

The sample was prepared as described in Example 3 with the difference that the quantity of sample was 10 $\mu$g. The sample was taken up in 50 $\mu$l of water and divided into 4 portions. One of the four aliquot parts was reduced in order to determine its purity by SDS-PAGE according to the method of Laemmli (24) with DTT (dithiothreitol) and separated on minigels (Höfer, 55×80×0.75 mm, 15%); the molecular weight marker used was the one specified in Example 2. Staining was carried out using the Oakley method (Oakley, B. R., et al., *Analyt. Biochem.* 105:361–363 (1986)). The electropherogram is shown in FIG. 9. This shows a single band as a molecular weight of about 30,000.

EXAMPLE 5 a) Tryptic Peptide Mapping

About 60 $\mu$g of the protein purified in Example 1d) was desalinated by reverse phase HPLC and further purified thereby. A Bakerbond WP C18 column (Baker; 4.6×250 mm) was used, and 0.1% trifluoroacetic acid in water (eluant A) or in acetonitrile (eluant B) was used as the mobile phase. The increase in gradient amounted to 20 to 68% eluant B in 24 minutes. Detection was carried out in parallel at 214 nm and at 280 nm. The fraction containing TNF-BP (retention time about 13.0 min.) was collected, dried and dissolved in 60 $\mu$l of 1% ammonium bicarbonate.

1% w/w, corresponding to 0.6 $\mu$g of trypsin (Boehringer Mannheim) was added to this solution and the reaction mixture was incubated for 6 hours at 37° C. Then a further 1% w/w of trypsin were added and incubation was continued overnight.

In order to reduce the disulfide bridges, the reaction mixture was then combined with 60 $\mu$l of 6 M urea and with 12 $\mu$l of 0.5 M dithiothreitol and left to stand for 2 hours at ambient temperature.

The tryptic cleavage peptides produced were separated by reverse phase HPLC, using a Delta Pak C18 column (Waters, 3.9×150 mm, 5 $\mu$m particle diameter, 100 A pore diameter) at 30° C. and 0.1% trifluoroacetic acid in water (eluant A) or in acetonitrile (eluant B) as the mobile phase. The gradient was increased from 0 to 55% of eluant B in 55 minutes, then 55% B was maintained for 15 minutes. The flow rate was 1 ml/min. and detection was carried out in parallel at 214 nm (0.5 AUFS) and at 280 nm (0.05 AUFS).

b) Sequence analysis of tryptic peptides

Some of the tryptic cleavage peptides of TNF-BP obtained in a) were subjected to automatic amino acid sequence analysis. The corresponding fraction from reverse phase HPLC were collected, dried and dissolved in 75 $\mu$l of 70% formic acid. These solutions were used directly for sequencing in an Applied Biosystems 477 A Pulsed Liquid Phase Sequenator. Table 1 contains the results of the sequence analysis of the tryptic peptides (the amino acids shown in brackets could not be identified with certainty). The letters "Xaa" indicate that at this point the amino acid could not be identified. In fraction 8 the amino acid in position 6 could not be identified. The sequence -Xaa-Asn-Ser- for position 6–8 leads one to suppose that the amino acid 6 is present in glycosylated form.

In fraction 17 the amino acid in position 6 could not be identified either. The sequence -Xaa-Asn-Ser- (already occurring in fraction 8) for positions 6–8 leads one to suppose that amino acid 6 is present in glycosylated form. The first 13 amino acids of fraction 17 are substantially identical to fraction 8; fraction 17 should thus be a peptide formed by incomplete tryptic cleavage.

It is striking that fraction 21 is identical to positions 7 to 14 of fraction 27. Both in fraction 21 and in fraction 27 the sequence suddenly breaks off after the amino acid asparagine (position 8 or 14), even though no tryptic cleavage can be expected here. This indicates that the amino acid asparagine (position 8 in fraction 21 or position 14 in fraction 27) could be the C-terminal amino acid of TNF-BP.

It is noticeable that the sequence of fraction 12 which occurs only in small amounts, is substantially identical to the secondary sequence of the N-terminus found in preliminary test 10. The fact that the proteins of the main and subsidiary sequence could not be separated on an analytical reverse phase HPLC column (Example 3b) indicated that the protein with the subsidiary sequence was a form of TNF-BP extended at the N-terminus, which was largely converted by processing into the protein with the main sequence.

TABLE 1

Amino acid sequence of the analyzed tryptic peptides of TNF-BP

| Fraction | Amino acid sequence |
|---|---|
| 1 | Asp-Ser-Val-Cys-Pro-Gln-Gly-Lys |
| 2 | Xaa-Xaa-Leu-Ser-(Cys)-Ser-Lys |
| 3 | Asp-Thr-Val-(Cys)-Gly-(Cys)-Arg |
| 4 | Glu-Asn-Glu-(Cys)-Val-Ser-(Cys)-Ser-Asn-(Cys)-Lys |
| 5 | Glu-Asn-Glu-(Cys)-Val-Ser-(Cys)-(Ser)-Asn-(Cys)-Lys-(Lys) |
| 8 | Tyr-Ile-His-Pro-Gln-Xaa-Asn-Ser-Ile-Xaa-Xaa-Xaa-Lys |
| 11 | Glu-Cys-Glu-Ser-Gly-Ser-Phe-Thr-Ala-Ser-Glu-Asn-(Asn)-(Lys) |
| 12 | Leu-Val-Pro-His-Leu-Gly-Asp-Arg |
| 13 | Lys-Glu-Met-Gly-Gln-Val-Glu-Ile-Ser-Ser-(Cys)-Thr-Val-Asp-(Arg) |
| 14/I | Gly-Thr-Tyr-Leu-Tyr-Asn-Asp-Cys-Pro-Gly-Pro-Gly-Gln- |
| 14/II | (Glu)-Met-Gly-Gln-Val-(Glu)-(Ile)-(Ser)-Xaa-Xaa-Xaa-(Val)-(Asp)- |
| 15 | Lys-Glu-Met-Gly-Gln-Val-Glu-Ile-Ser-Ser-(Cys)-Thr-VAl-Asp-Arg Asp-Thr-Val-(Cys)-Gly- |
| 17 | Tyr-Ile-His-Pro-Gln-Xaa-Asn-Ser-Ile-(Cys)-(Cys)-Thr-Lys-(Cys) His-Lys-Gly-Xaa-Tyr- |
| 20 | Gly-Thr-Tyr-Leu-Tyr-Asn-Asp-Cys-Pro-Gly-Pro-Gly-Gln-Asp-Thr-Xaa-Xaa-Arg |
| 21 | Leu-(Cys)-Leu-Pro-Gln-Ile-Glu-Asn |
| 26 | Gln-Asn-Thr-Val-(Cys)-Thr-Xaa-(His)-Ala-Gly-Phe-(Phe)-Leu-(Arg) |

TABLE 1-continued

Amino acid sequence of the analyzed tryptic peptides of TNF-BP

| Fraction | Amino acid sequence |
|---|---|
| 27 | Ser-Leu-Glu-(Cys)-Thr-Lys-Leu-(Cys)-Leu-Pro-Gln-Ile-Glu-Asn |

EXAMPLE 6

Analysis of the C-terminus

This analysis was carried out on the principle of the method described in (Hsieng, S. L., et al., *J. Chromatography* 447:351–364 (1988)).

About 60 µg of the protein purified in Example 2d were desalinated and thus further purified by reverse phase HPLC. A Bakerbond WP C18 column (Baker; 4.6×250 mm) was used and 0.1% trifluoroacetic acid in water (eluant A) or in acetonitrile (eluant B) was used as the mobile phase. The gradient was increased from 20 to 68% eluant B in 24 minutes. Detection was carried out in parallel at 214 nm and at 280 nm. The fraction containing TNF-BP (retention time about 13.0 min.) was collected, dried and dissolved in 120 µl of 10 mM sodium acetate (adjusted to pH 4 with 1 N HCl).

To this solution were added 6 µl of Brij 35 (10 mg/ml in water) and 1.5 µl of carboxypeptidase P (0.1 mg/ml in water, Boehringer Mannheim, No. 810142). This corresponds to a weight ratio of enzyme to protein of 1 to 400 (Frohman, M. A., et al., *Proc. Natl. Acad. Sci.* 85:8998–9002 (1988)).

Immediately after the addition of the enzyme a sample of 20 µl of the reaction mixture was taken and the enzymatic reaction therein was stopped by acidifying with 2 µl of concentrated trifluoroacetic acid and by freezing at –20° C.

The reaction mixture was left to stand in a refrigerator (about 8° C.) and samples of 20 µl were taken after 10, 20, 60 and 120 minutes. The remainder of the reaction mixture was left at ambient temperature for another 120 minutes. Immediately after being taken, all the samples were acidified by the addition of 2 µl of concentrated trifluoroacetic acid and frozen at –20° C., thereby interrupting the enzymatic reaction.

Parallel to the sample mixture described, containing about 60 µg of TNF-BP, a reagent double blind control was set up under identical conditions but with no protein added.

After the last sample had been taken all the samples were dried for 30 minutes in a Speed Vac Concentrator, mixed with 10 µl of a solution of 2 parts of ethanol, 2 parts of water and 1 part of triethylamine (="Redrying solution" of the Picotag amino acid analysis system of Messrs. Waters) and briefly dried again. Then the samples were each mixed with 20 µl of the derivatization reagent (7:1:1:1=ethanol:water:-triethylamine:phenylisothiocyanate; Picotag system) in order to derivatize the amino acids split off from the C-terminus, then left to stand for 20 minutes at ambient temperature and then dried for 1 hour in a Speed Vac Concentrator.

In order to analyze the derivatized amino acids the samples were dissolved in 100 µl of "Sample Diluent" (Picotag system made by Waters). Of these solutions, 50 µl was analyzed by reverse phase HPLC (column, mobile phase and gradient according to the original specifications of the Picotag system made by Waters). The chromatograms of the samples and reagent double blind controls were compared with the chromatogram of a similarly derivatized mixture (100 pmol/amino acid) of standard amino acids (Messrs. Beckman).

As can be seen from the quantitative results of the Picotag amino acid analysis (Table 2), asparagine is very likely the C-terminal amino acid of TNF-BP. Apart from asparagine, glutamic acid and a smaller amount of isoleucine were also detected after 240 minutes' reaction. Quantities of other amino acids significantly above the reagent double blind value could not be found even after 240 minutes reaction. This result (-Ile-Glu-Asn as the C-terminus) confirms the supposition made from the N-terminal sequencing of the tryptic peptides 21 and 27, to the effect that the amino acids identified at the C-terminus in these peptides-Ile-Glu-Asn (Example 5b)—constitute the C-terminus of TNF-BP.

TABLE 2

Quantitative evaluation of the Picotag amino acid analysis after reaction of carboxypeptidase P with TNF-BP

| Reaction time | Integrator units for the amino acids | | |
|---|---|---|---|
| | Isoleucine | Glutamic acid | Asparagine |
| 0 | — | — | |
| 10 | — | — | |
| 20 | — | — | 83.304 |
| 60 | — | — | 168.250 |
| 120 | — | — | 319.470 |
| 240 | 85.537 | 52.350 | 416.570 |

METHODS USED IN EXAMPLES 7 TO 21

In the Examples which follow, standard molecular biological methods were used unless expressly stated otherwise, which can be found in the relevant textbooks or which correspond to the conditions recommended by the manufacturers. To simplify the description of the Examples which follow, frequently recurring methods or designations are abbreviated:

"Cutting" or "digestion" of DNA refers to the catalytic cleaving of the DNA using restriction endonucleases (restriction enzymes) at sites specific to them (restriction sites). Restriction endonucleases are commercially available and are used under the conditions recommended by the manufacturers (buffer, bovine serum albumin (BSA) as carrier protein, dithiothreitol (DTT) as antioxidant). Restriction endonucleases are designated by a capital letter, usually followed by small letters and normally a Roman numeral. The letters depend on the microorganism from which the restriction endonuclease in question was isolated (e.g.: Sma I: *Serratia marcescens*). Usually, about 1 μg of DNA is cut with one or more units of the enzyme in about 20 μl of buffer solution. Normally, an incubation period of 1 hour at 37° C. is used, but this can be varied in accordance with the manufacturer's instructions for use. After cutting, the 5'-phosphate group is sometimes removed by incubation with alkaline phosphatase from calves intestines (CIP). This serves to prevent an undesirable reaction of the specific site in a subsequent ligase reaction (e.g. circularization of a linearized plasmid without the insertion of a second DNA fragment). Unless otherwise stated, DNA fragments are normally not dephosphorylated after cutting with restriction endonucleases. Reaction conditions for incubation with alkaline phosphatase can be found for example in the M13 Cloning and Sequencing Handbook (Amersham, PI/129/83/12). After the incubation protein is removed by extraction with phenol and chloroform and the DNA is precipitated from the aqueous phase by the addition of ethanol.

"Isolation" of a specific DNA fragment means the separation of the DNA fragments obtained by restriction digestion, e.g. on a 1% agarose gel. After electrophoresis and rendering the DNA visible in UV light by staining with ethidium bromide (EtBr) the desired fragment is located by means of molecular weight markers which had been applied and bound by further electrophoresis on DE 81 paper (Schleicher and Schüll). The DNA is washed by rinsing with low salt buffer (200 mM NaCl, 20 mM Tris pH=7.5, 1 mM EDTA) and then eluted with a high salt buffer (1 M NaCl, 20 mM Tris pH=7.5, 1 mM EDTA). The DNA is precipitated by the addition of ethanol.

"Transformation" means the introduction of DNA into an organism so that the DNA can be replicated therein, either extrachromosomally or chromosomally integrated. Transformation of *E. coli* follows the method specified in the M13 Cloning and Sequencing Handbook (Amersham, PI/129/83/12).

"Sequencing" of a DNA means the determination of the nucleotide sequence. To do this, first of all the DNA which is to be sequenced is cut with various restriction enzymes and the fragments are introduced into suitably cut M13 mp8, mp9, mp18 or mp19 double stranded DNA, or the DNA is fragmented by ultrasound, the ends repaired and the size-selected fragments introduced into Sma I cut, dephosphorylated M13 mp8 DNA (Shotgun method). After transformation of *E. coli* JM 101, single stranded DNA is isolated from recombinant M13 phages in accordance with the M13 Cloning and Sequencing Handbook (Amersham, PI/129/83/12) and sequenced by the dideoxy method (Sanger et al., *Proc. Natl. Acad. Sci.* 74:5463–5467 (1977)). As an alternative to the use of the klenow fragment of *E. coli* DNA polymerase I it is possible to use T7-DNA polymerase ("Sequenase," made by United States Biochemical Corporation). The sequence reactions are carried out in accordance with the manual "Sequenase: Step-by-Step Protocols for DNA Sequencing With Sequenase" (Version 2.0).

Another method of sequencing consists in cloning the DNA which is to be sequenced into a vector which carries, inter alia, a replication origin of a DNA single-strand phage (M13, fl) (e.g. Bluescribe or Bluescript M13 made by Stratagene). After transformation of *E. coli* JM101 with the recombinant molecule, the transformants can be infected with a helper phage, e.g. M13K07 or R408 made by Promega). As a result, a mixture of helper phages and packaged, single-stranded recombinant vector is obtained. The sequencing template is worked up analogously to the M13 method. Double-stranded plasmid DNA is denatured by alkali treatment and directly sequenced in accordance with the above-mentioned sequencing handbook.

The sequences were evaluated using the computer programs originally developed by R. Staden (Staden, R., *Nucleic Acid Res.* 10:4731–4751 (1982)) and modified by Ch. Pieler (Pieler Ch., Dissertation, Universitat Wien (1987)). "Ligating" refers to the process of forming phosphodiester bonds between two ends of double strand DNA fragments. Usually, between 0.02 and 0.2 μg of DNA fragments in 10 μl are ligated with about 5 units of T4DNA ligase ("ligase") in a suitable buffer solution (Maniatis, T., et al., *Molecular Cloning A laboratory Manual. Cold Spring Harbor Laboratory*, p. 474 (1982)). "Excising" of DNA from transformants refers to the isolation of the plasmid DNA from bacteria by the alkaline SDS method, modified according to Birnboim and Doly, leaving out the lysozyme. The bacteria are used from 1.5 to 50 ml of culture.

"Oligonucleotides" are short polydeoxynucleotides which are chemically synthesized. The Applied Systems Synthesizer Model 381A is used for this. The oligonucleotides are worked up in accordance with the Model 381A User Manual (Applied Biosystems). Sequence primers are used directly without any further purification. Other oligonucleotides are purified up to a chain length of 70 by the OPC method (OPC=Oligonucleotide purification column, Applied Biosystems, Product Bulletin, January 1988). Longer oligonucleotides are purified by polyacrylamide gel electrophoresis (6% acrylamide, 0.15% bisacrylamide, 6 M urea, TBE buffer) and after elution from the gel, desalinated over a G-25 sepharose column.

EXAMPLE 7
Preparation of TNF-BP-specific Hybridization Probes

The oligonucleotides were selected, with a view to using them to amplify cDNA, by PCR:

a) From the N-terminal amino acid sequence of the TNF-binding protein (main sequence, obtained from preliminary test 3 and Example 5, fraction 1)

Asp-Ser-Val-Cys-Pro-Gln-Gly-Lys-Tyr-Ile-His-Pro-Glna heptapeptide region was selected which permits the lowest possible complexity of a mixed oligonucleotide for hybridizing to cDNA: these are amino acids 6 to 12. In order to reduce the complexity of the mixed oligonucleotide, four mixed oligonucleotides were prepared each having a complexity of 48. The oligonucleotides were prepared in the direction of the mRNA and are thus oriented towards the 3' end of the sequence and are identical to the non-coding strand of the TNF-BP gene:

```
Gln-Gly-Lys-Tyr-Ile-His-Pro

5'CAA GGT AAA TAT ATT CAT CC 3'TNF-BP #3/1 EBI-1639
     G       G   C   C   C
                     A

5'CAA GGC AAA TAT ATT CAT CC 3'TNF-BP #3/2 EBI-1640
     G       G   C   C   C
                     A

5'CAA GGA AAA TAT ATT CAT CC 3'TNF-BP #3/3 EBI-1641
     G       G   C   C   C
                     A

5'CAA GGG AAA TAT ATT CAT CC 3'TNF-BP #3/4 EBI-1642
     G       G   C   C   C
                     A
``` b) From the amino acid sequence of a tryptic peptide (fraction 11 of the tryptic digestion) of the amino acid sequence Glu-Cys-Gl u-Ser-Gly-Ser-Phe-Thr-Ala-Ser-(Glu/Cys)-Asn-Asn-Lys (cf. Example 5)

a peptide region was selected and another set of mixed oligonucleotides were synthesized:

```
-Phe-Thr-Ala-Ser-Glu-Asn-ASn-Lys
                 Cys

TFN-BP #4/5 (EBI-1653):
3'AAA TGA CGG AGA CTC TTG TTG TT CCTAGGG 5'
     G   G   T   T   T
         T

TNF-BP #4/6 (EBI-1654):
3'AAA TGA CGG TCA CTC TTG TTG TT CCTAGGG 5'
     G   G   T   T   T
         T

TNF-BP #4/7 (EBI-1657):
3'AAA TGA CGG AGA ACA TTG TTG TT CCTAGGG 5'
```
     G   G   T   T   T
         T

TNF-BP #4/8 (EBI-1658):
3'AAA TGA CGG TCA ACA TTG TTG TT CCTAGGG 5'
     G   G   T   T   T
         T
```

The oligonucleotides were synthesized complementarily to mRNA and are thus oriented towards the 5' end of the sequence. In order to allow efficient cloning of the amplified DNA fragment following the PCR, a BamHI linker was also provided at the 5' end of the oligonucleotides. If for example oligonucleotides TNF-BP Nos. 4/5–8 together with TNF-BP No. 3/1–4 are used for the PCR on-the entire λ DNA of a library, any DNA fragment which results can be subsequently cut with BamHI. The partner oligonucleotides yield a straight end at the 5' terminus and consequently the fragment can be cloned into the SmaI-BamHI sites of a suitable vector.

Each mixed oligonucleotide TNF-BP No. 4/5 to 8 is a mixture of 48 individual nucleotides and does not take into account a few codons, namely:

Thr ACG

Ala GCG and GCT

Ser TCG and TCC

Asn AAT

In the case of GCT the possibility that the triplet CGG complementary to GCC (Ala) can be effective by forming a G-T bridge is taken into consideration, while in the case of TCG (Ser) and MAT (Asn) the same applies with regard to AGT and TTG, respectively.

ACG, GCG and TCG are extremely rare codons (CG rule) and are therefore not taken into consideration.

EXAMPLE 8
Amplification of a Partial Sequence Coding for TNF-BP from a cDNA Library a) Isolation of λ-DNA of a cDNA library The cDNA library was prepared using the method described in EP-A1–0293 567 for the human placental cDNA, with the difference that the starting material used was 109 fibrosarcoma cells of the cell line HS 913 T, which had been grown by stimulation with human TNF-α (10 ng/ml). Instead of λ gt10, λ gt11 was used (cDNA synthesis: Amersham RPN 1256; EcoRI digested λ gt11 arms: Promega Biotech; in vitro packaging of the ligated DNA: Gigapack Plus, Stratagene).

5 ml of the phage supernatant of the amplified cDNA library of the human fibrosarcoma cell line HS913T in λ gt11 were mixed with 0.5 µg of RNase A and 0.5 µg of DNase I and incubated for 1 hour at 37° C. The mixture was centrifuged for 10 minutes at 5000×g, the supernatant was freed from protein by extraction with phenol and chloroform and the DNA was precipitated from the aqueous phase by the addition of ethanol. The λ-DNA was dissolved in TE buffer (10 mM Tris pH 7.5; 1 mM EDTA).

b) PCR amplification of a TNF-BP seguence from a cDNA library

For the application of PCR (Saiki et al., *Science* 239:487–491 (1988)) to DNA from the HS913T cDNA library, 16 individual reactions were carried out, in each of which one of the 4 mixed oligonucleotides EBI-1639, EBI- 1640, EBI-1641, EBI-1642 were used as first primers and one of the four mixed oligonucleotides EBI-1653, EBI-1654, EBI-1657 and EBI-1658 was used as the second primer. Each of these mixed oligonucleotides contains 48 different oligonucleotides of equal length.

Amplification by means of PCR took place in 50 µl reaction volume, containing 250 ng of λ-DNA from the cDNA library, 50 mM KCl, 10 mM Tris pH=8.3, 1.5 mM MgCl$_2$, 0.01% gelatine, 0.2 mM of each of the 4 deoxynucleoside triphosphates (dATP, dGTP, dCTP, dTTP), 200 pmol of each of first and second primer and 1.25 units of Taq polymerase [Perkin-Elmer Cetus]. To prevent evaporation the solution was coated with a few drops of mineral oil (0.1 ml) the PCR was carried out in a DNA Thermal Cycler (Perkin Elmer Cetus) as follows: the samples were heated to 94° C. for 5 minutes in order to denature the DNA, and then subjected to 40 amplification cycles. One cycle consisted of 40 seconds' incubation at 94° C., 2 minutes incubation at 55° C. and 3 minutes incubation at 72° C. At the end of the last cycle the samples were incubated at 72° C. for a further 7 minutes to ensure that the last primer lengthening had been completed. After cooling to ambient temperature, the samples were freed from protein with phenol and chloroform and the DNA was precipitated with ethanol.

5 µl of each of the 16 PCR samples were applied to an agarose gel and the length of the amplified DNA fragments was determined after electrophoretic separation. The most intense DNA band, a fragment 0.16 kb long, could be seen in the PCR samples which had been amplified with the oligonucleotide EBI-1653 as the first primer and one of the oligonucleotides EBI-1639, EBI-1640, EBI-1641 or EBI-1642 as the second primer. Since the sample amplified with the pair of primers EBI-1653 and EBI-1642 contained the largest amount of this 0.16 kb DNA fragment, this sample was selected for further processing.

EXAMPLE 9

Cloning and Sequencing of a DNA Fragment Obtained by PCR Amplification

The PCR product of primers EBI-1642 and EBI-1653 obtained was cut with BamHI and subsequently separated by electrophoresis in an agarose gel (1.5% NuSieve GTG agarose plus 1% Seakem GTG agarose, FMC Corporation) according to size. The main band, a DNA fragment 0.16 kb long, was electroeluted from the gel and precipitated with ethanol. This DNA fragment was ligated with BamHI/SmaI cut plasmid pUC18 (Pharmacia) and E. coli JM101was transformed with the ligation mixture. The plasmids prepared by the mini-preparation method were characterized by cutting with the restriction enzymes PvuII and EcoRI-BamHI and subsequent electrophoresis in agarose gels. The plasmid pUC18 contains two cutting sites for PvuII which flank the polycloning site in a 0.32 kb DNA fragment. Very short DNA inserts in the polycloning site of the plasmid can be made visible more easily in agarose gel after cutting with PvuII since the length is extended by 0.32 kb. By cutting with EcoRI and BamHI the DNA fragment ligated into. the plasmid vector cut with BamHI and SmaI, including some base pairs of the polylinker sequence, can be obtained. A clone with the desired insert has been designated pTNF-BP3B. The entire DNA insert of this clone was sequenced after subcloning of an EcoRI-BamHI fragment in M13mp18 (Pharmacia) by the modified dideoxy method using sequenase (United States Biochemical Corporation).

Analysis of the PCR-amplified DNA gave the following sequence (only the non-coding strand is shown, and above it the derived amino acid sequence):

```
                          5                         10
         Gln Gly Lys Tyr Ile His Pro Gln Asn Asn Ser Ile Cys
         CAG GGG AAA TAT ATT CAC CCT CAA AAT AAT TCG ATT TGC 15                       20                      25
         Cys Thr Lys Cys His Lys Gly Thr Tyr Leu Tyr Asn Asp
         TGT ACC AAG TGC CAC AAA GGA ACC TAC TTG TAC AAT GAC 30                     35
         Cys Pro Gly Pro Gly Gln Asp Thr Asp Cys Arg Glu Cys
         TGT CCA GGC CCG GGG CAG GAT ACG GAC TGC AGG GAG TGT 40                      45                     50
         Glu Ser Gly Ser Phe Thr Ala Ser Glu Asn Asn Lys
         GAG AGC GGC TCC TTC ACA GCC TCA GAA AAC AAC AAG GAT CC
```

The first 20 and last 29 nucleotides (underlined script) correspond to the sequences of the primer oligonucleotides EBI-1642 and the complement of EBI-1653, respectively. Amino acids 38 to 43 confirm the remaining sequence of the tryptic peptide 11. Furthermore, the DNA fragment produced by PCR contains the sequence of the peptide of fraction 20 of the tryptic digestion (amino acids 20 to 34, underlined). This shows that the clone pTNF-BP3B was derived from a cDNA which codes for TNF binding protein. pTNF-BP3B therefore constitutes a probe, e.g. for searching for TNF-BP cDNAs in cDNA libraries.

EXAMPLE 10

Isolation of TNF-BP cDNA Clones

About 720,000 phages of the HS913T cDNA library inλ gt11 were plated on E. coli Y1088 (ΔlacU169, pro::Tn5, tonA2, hsdR, supE, supF, metB, trpR, F-,λ-, (pMC9)) (about 60,000 phages per 14.5 cm petri dish, LB-agar: 10 g/l tryptone, 5 g/l of yeast extract, 5 g/l of NaCl, 1.5% agar, plating in top agarose: 10 g/l of tryptone, 8 g/l of NaCl, 0.8% agarose). Two nitrocellulose filter extracts were prepared from each plate. The filters were prewashed (16 hours at 65° C.) in:

| 50 mM | Tris/HCl pH = 8.0 |
|---|---|
| 1 M | NaCl |
| 1 mM | EDTA |
| 0.1% | SDS |

The filters were pre-hybridized for two hours at 65° C. in:

| | |
|---|---|
| 6x | SSC (0.9 M NaCl, 0.09 M trisodium citrate) |
| 5x | Denhardt's (0.1% Ficoll, 0.1% polyvinylpyrrolidone, 0.1% BSA (= bovine serum albumin) |
| 0.1% | SDS |

Preparation of the radioactively labelled probe: pTNF-BP 3B was doubly cut with BamHI and EcoRI and the approximately 0.16 kb insert was isolated. 0.6 μg of the insert in 32 μl were denatured at 100° C. and primed with 60 pmol each of EBI-1642 and EBI-1653 by cooling to 80° C. over 10 minutes and rapid cooling in ice water. After the addition of

| | |
|---|---|
| 10 μl | α-$^{32}$P-dCTP (100 μCi, 3.7 MBq) |
| 5 μl | 10x priming buffer (0.1 M Tris/HCl pH = 8.0, 50 mM MgCl$_2$) |
| 2 μl | 1 mM dATP, dGTP, dTTP |
| 1 μl | PolIK (Klenow fragment of E. coli DNA polymerase I, 5 units) |

Incubation was carried out for 90 minutes at ambient temperature. After heat inactivation (10 minutes at 70° C.), the non-incorporated radioactivity was removed by chromatography on Biogel P6DG (Biorad) in TE buffer (10 mM Tris/HCl pH=8, 1 mM EDTA). 65×10$^6$ cpm were incorporated. The hybridization of the filters was carried out in a total volume of 80 ml of 6×SSC/5× Denhardt's/0.1% SDS plus heat-denatured hybridizing probe for 16 hours at 65° C. The filters were washed twice for 30 minutes at ambient temperature in 6×SSC/0.01% SDS and once for 45 minutes at ambient temperature in 2×SSC/0.01% SDS and three times for 30 minutes at 65° C. in 2×SSC/0.01% SDS. The filters were dried in air and then exposed to Amersham Hyperfilm for 16 hours using an intensifier film at −70° C. In all, 30 hybridizing plaques were identified (λ-TNF-BP No. 1-30). The regions with the hybridizing plaques were pricked out as precisely as possible and the phages were eluted in 300 μl of SM buffer plus 30 μl of chloroform. By plaque purification (plating of about 200 phages per 9 cm petri dish on the second passage, or about 20 phages per 9 cm petri dish on the third passage, filter extracts doubled, preparation, hybridization and washing (as described in the first search) 25 hybridizing phages were finally separated (λ-TNF-BP #1–10, 12–24, 29,30).

Preparation of the Recombinant λ-DNA from the Clones λ-TNF-BP Nos. 13, 15, 23, 30:

2×10$^6$ phages were plated on E. coli Y1088 in top agarose (10 g/l tryptone, 8 g/l NaCl, 0.8% agarose) (14.5 cm petri dish) with LB agarose (1.5% agarose, 0.2% glucose, 10 mM MgSO4, 10 g/l tryptone, 5 g/l yeast extract, 5 g/l NaCl) and incubated at 37° C. for 6 hours. After the plates had been cooled (30 minutes at 4° C.) they were coated with 10 ml of λ-diluent (10 mM Tris/HCl pH=8.0, 10 mM MgCl$_2$, 0.1 mM EDTA) and eluted for 16 hours at 4° C. The supernatant was transferred into 15 ml Corex test tubes and centrifuged for 10 minutes at 15000 rpm and at 4° C. (Beckman J2-21 centrifuge, JA20 rotor). The supernatant was decanted into 10 ml polycarbonate test tubes and centrifuged at 50000 rpm at 20° C. until ω$^2$t=3×10$^{10}$ (Beckman L8-70, 50 Ti rotor). The pellet was resuspended in 0.5 ml of λ-diluent and transferred into Eppendorf test tubes (1.4 ml). After the addition of 5 μg of RNase A and 0.5 μg DNaseI and incubation at 37° C. for 30 minutes and the addition of 25 μl of 0.5 M EDTA, 12.5 μl of 1 M Tris/HCl pH=8.0, 6.5 μl of 20% SDS, incubation was continued at 70° C. for 30 minutes. The λ-DNA was purified by phenol/chloroform extraction and precipitated with ethanol. Finally, the DNA was dissolved in 100 μl of TE buffer.

EXAMPLE 11

Subcloning and Sequencing of TNF-BP cDNA Clones 15 and 23

In order to characterize the cDNAs of the clones λTNF-BP15 and λTNF-BP23, which showed the strongest signals during hybridization, the cDNA inserts were cut out of the λ-DNA with EcoRI, then after electrophoretic separation eluted from an agarose gel and precipitated with ethanol. The DNA fragments of 1.3 kb (from λTNF-BP15) and 1.1 kb (from λTNF-BP23) were cut with EcoRI and ligated with alkaline phosphatase from calves' intestines dephosphorylated plasmid vector pT7/T3α-18 (Bethesda Research Laboratories) with T4 DNA ligase and E. coli JM101 was transformed. From individual colonies of bacteria which showed no blue staining after selection on agarose plates with ampicillin and X-gal, plasmid DNA was prepared in a mini preparation process and the presence and orientation of the cDNA insert was determined by cutting with EcoRI and HindIII. Plasmids which contained the EcoRI insert of the phages λTNF-BP15 or λTNF-BP23 oriented in such a way that the end corresponding to the 5'-end of the mRNA is facing the T7 promotor were designated pTNF-BP15 and pTNF-BP23, respectively. The EcoRI inserts of λTNF-BP15 and λTNFBP23 were also ligated in M13mp19 vector which had been cut with EcoRI and dephosphorylated, and E. coli JM101 was transformed. From a few randomly selected M13 clones, single-stranded DNA was prepared and used as the basis for sequencing by the dideoxy method. On M13 clones which contained the cDNA inserts in the opposite orientation, both DNA strands were fully sequenced using the universal sequencing primer and specifically synthesized oligonucleotide primers which bind to the cDNA insert.

The complete nucleotide sequence of 1334 bases of the cDNA insert of λTNF-BP15 or pTNF-BP15 is shown in FIG. 1. Bases 1–6 and 1328–1334 correspond to the EcoRI linkers which had been added to the cDNA during the preparation of the cDNA library. The nucleotide sequence of the cDNA insert of λTNF-BP23 corresponds to that of λTNF-BP15 (bases 22–1100), flanked by EcoRI linkers.

The clone λTNF-BP30 was also investigated; its sequence corresponds to λ-TNF-BP15, except that the sequence has a deletion of 74 bp (nucleotide 764 to 837).

EXAMPLE 12

Construction of the Expression Plasmid pAD-CMV1 and pADCMV2

From parts of the expression plasmids pCDM8 (Seed and Aruffo, Proc. Natl. Acad. Sci. 84:8573–8577 (1987); Seed , B. Nature 329:840–842 (1987)); Invitrogen), pSV2gptDHFR20 (EP-A1 0321 842) and the plasmid Bluescript SK+ (Short, J. M., et al., Nucl. Acids Res. 11:5521–5540 (1988); Stratagene) a new plasmid was constructed which has a multi-cloning site for the directed insertion of heterologous DNA sequences and which can be replicated in E. coli by means of ampicillin resistance with a high copy number. The intergenic region of M13 makes it possible to produce single-stranded plasmid DNA by superinfection of the transformed bacteria with a helper phage (e.g. R408 or M13K07) to facilitate sequencing and mutagenesis of the plasmid DNA. The T7 promotor which precedes the multi-cloning site makes it possible to prepare RNA transcripts in vitro. In mammalian cells heterologous genes are expressed, driven by cytomegalovirus (CMV) promotor/enhancer (Boshart, M., et al., *Cell* 41:521–530 (1985)). The SV40 replication origin makes it possible, in suitable cell lines (e.g. SV40 transformed cells such as COS-7, adenovirus transformed cell line 293 (ATCC CRL1573)), to carry out autonomous replication of the expression plasmid at high copy numbers and thus at high rates in transient expression. For preparing permanently transformed cell lines and subsequently amplifying the expression cassette by means of methotrexate, a modified hamster minigene is used (promotor with coding region and the first intron) for dihydrofolate reductase (DHFR) as the selection marker.

a) Preparation of the vector and promotor sections by PCR

The plasmid Bluescript SK+ was linearized with HindIII and 5 ng of DNA was used in a 100 μl PCR mixture (reaction buffer: 50 mM KCl, 10 mM Tris-Cl pH=8.3, 1.5 mM MgCl$_2$, 0.01% (w/v) gelatine, 0.2 mM of the four deoxynucleotide triphosphates (dATP, dGTP, dCTP, dTTP), 2.5 units of Taq polymerase per 100 μl. The primers used were 50 pmol of the synthetic oligonucleotides EBI1786 (5'-GGAATTCAGCCTGAATGGCGAATGGG-3'; binds just outside the M13 ori-region in Bluescript position 475, independently of the M13 ori-orientation) and EBI-1729 (5'-CCTCGAGCGTTGCTGGCGTTTTTCC-3'; binds to Bluescript at position 1195 in front of ori, corresponds to the start of the Bluescript sequence in pCDM8, 6 bases 5' yield XhoI). After 5 minutes denaturing at 94° C. PCR was carried out over 20 cycles (40 seconds at 94° C., 45 seconds at 55° C., 5 min at 72° C., Perkin Elmer Cetus Thermal Cycler). The oligonucleotides flank the intergenic region of M13 or the replication origin (ori) with the intermediate gene for β-lactamase. At the same time, at the end of the replication origin an XhoI cutting site is produced and at the other end an EcoRI cutting site. The reaction mixture was freed from protein by extraction with phenol/chloroform and the DNA was precipitated with ethanol. The DNA obtained was cut with XhoI and EcoRI and after electrophoresis in an agarose gel a fragment of 2.3 kb was isolated.

5 ng of plasmid pCDM8 linearized with SacII was amplified by PCR with the oligonucleotides EBI-1733 (5'GGTCGACATTGATTATTGACTAG-3'; binds to CMV promotor region (position 1542) of pCDM8, corresponding to position 1 in pAD-CMV, SalI site for cloning) and EBI-1734 (5'GGAATTCCCTAGGAATACAGCGG-3'; binds to polyoma origin of 3'SV40 polyA region in pCDM8 (position 3590)) under identical conditions to those described for Bluescript SK+. The oligonucleotides bind at the beginning of the CMV promotor/enhancer sequence and produce an SalI cutting site (EBI-1733) or bind to the end of the SV40 poly-adenylation site and produce an EcoRI cutting site (EBI-1734). The PCR product was cut with SalI and EcoRI and a DNA fragment of 1.8 kb was isolated from an agarose gel.

Figure 3A:
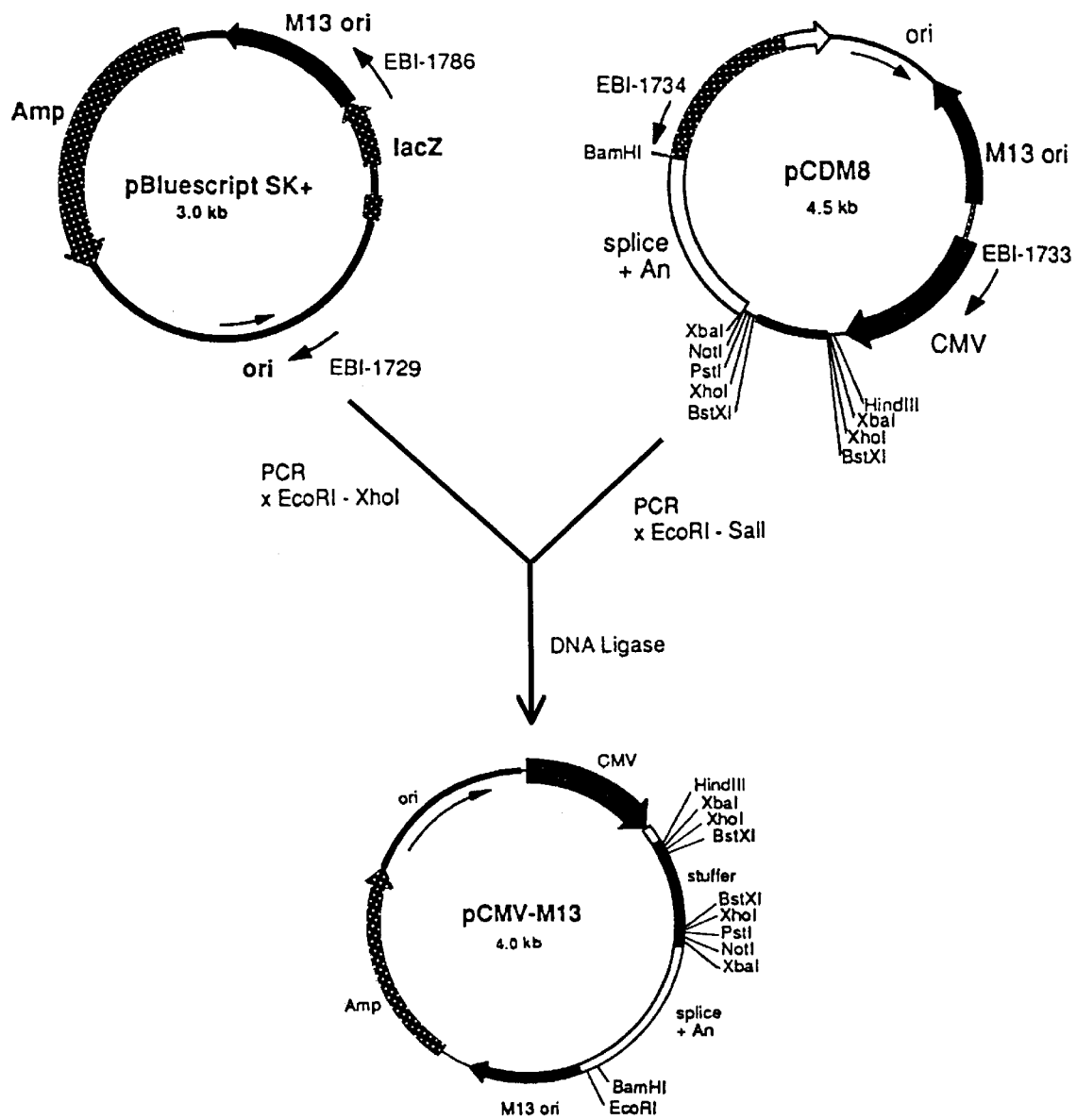
Figure 3B:
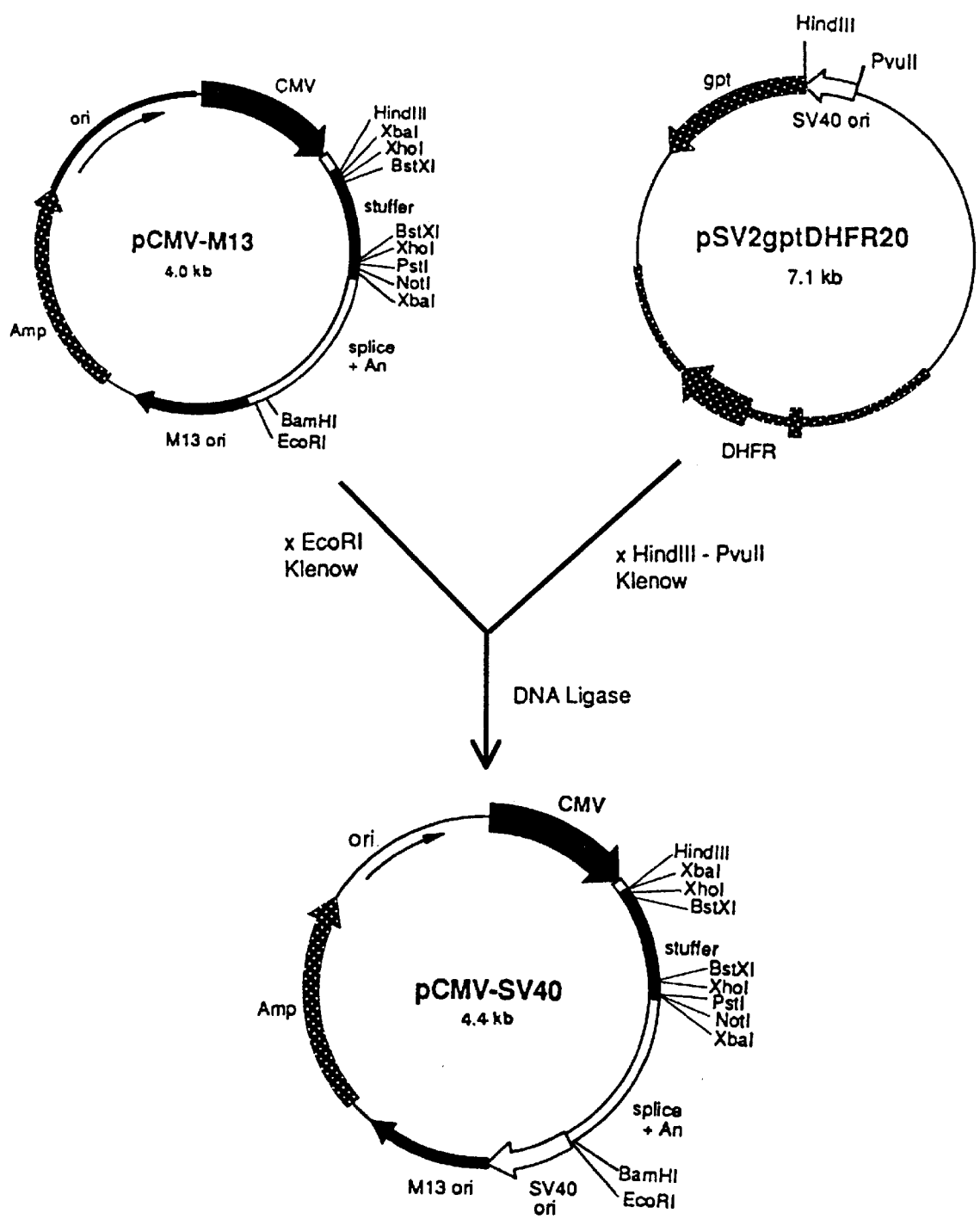

The two PCR products were ligated with T4 DNA ligase, *E. coli* HB101 transformed with the resulting ligation product and plasmid DNA was amplified and prepared using standard methods. The plasmid of the desired nature (see FIG. 3) was designated pCMV-M13. The SV40 replication origin (SV40 ori) was isolated from the plasmid pSV2gptDHFR20 (EP-A1 0321842). To do this, this plasmid was doubly cut with HindIII and PvuII and the DNA ends were blunted by subsequent treatment with the large fragment of the *E. coli* DNA polymerase (klenow enzyme) in the presence of the four deoxynucleotide triphosphates. A 0.36 kb DNA fragment thus obtained was isolated from an agarose gel and ligated into pCMV-M13 linearized with EcoRI. A plasmid obtained after transformation of *E. coli* HB11, with the SV40 ori in the same orientation as the β-lactamase gene and the CMV promotor, was designated pCMV-SV40. The construction of this plasmid is shown in FIG. 3.

b) Mutagenesis of the DHFR gene

In order to prepare an expression plasmid with a versatile multicloning site, two restriction enzyme cutting sites were removed from the DHFR minigene by directed mutagenesis and three such sites were removed by deletion. To do this, a 1.7 kb BglII fragment from the plasmid pSV2gptDHFR20, containing the entire coding region of the hamster DHFR gene, was cloned into the BglII site of the plasmid pUC219 (IBI) and the plasmid pUCDHFR was obtained. *E. coli* JM109 (Stratagene) cells transformed with pUCDHFR were infected with an approximately 40-fold excess of the helper phage R408 (Stratagene) and shaken in LB medium for 16 hours at 37° C. Single stranded plasmid DNA was isolated from the bacterial supernatant.

Controlled mutagenesis was carried out in two successive steps, using the in vitro mutagenesis system RPN1523 (Amersham). The EcoRI site located at the beginning of Exon 2 was destroyed by exchanging a base from GAATTC to GAGTTC. This base exchange does not result in any change in the coded amino acid sequence and furthermore corresponds to the nucleotide sequence in the natural murine DHFR gene (McGrogan, M., et al., *J. Biol. Chem.* 260:2307–2314 (1985); Mitchell, P. J., et al., *Mol. Cell. Biol.* 6:425–440 (1986)). An oligonucleotide (Antisense orientation) of the sequence 5'-GTACTTGAACTCGTTCCTG-3' (EBI-1751) was used for the mutagenesis. A plasmid with the desired mutation was prepared as single strand DNA as described above and the PstI site located in the first intron was removed by mutagenesis with the oligonucleotide EBI-1857 (Antisense orientation, 5'-GGCAMGGGCAGCAGCCGG-3') from CTGCAG into CTGCTG. The mutations were confirmed by sequencing and the resulting plasmid was designated pUCDHFR-Mut2.

The 1.7 kb BglII fragment was isolated from the plasmid pUCDHFR-Mut2 and ligated into plasmid pSV2gptDHFR20, doubly cut with BglII and BamHI. After transformation of *E. coli*, amplification and DNA isolation, a plasmid of the desired nature was obtained, which was designated pSV2gptDHFR-Mut2. By cutting with BamHI, in the 3'-non-coding region of the DHFR gene a 0.12 kb DNA fragment following the BglII site was removed, which also contains a KpnI cutting site. By linking the overhanging DNA ends formed with BglII and BamHI, the recognition sequences for these two enzymes were also destroyed.

The plasmid pCMV-SV40 was doubly cut with EcoRI and BamHI and the DNA ends were then blunted with Klenow enzyme. The DNA was purified by extraction with phenol chloroform and ethanol precipitation, then dephosphorylated by incubation with alkaline phosphatase and the 4.4 kb long vector DNA was isolated from an agarose gel.

Figure 4A:
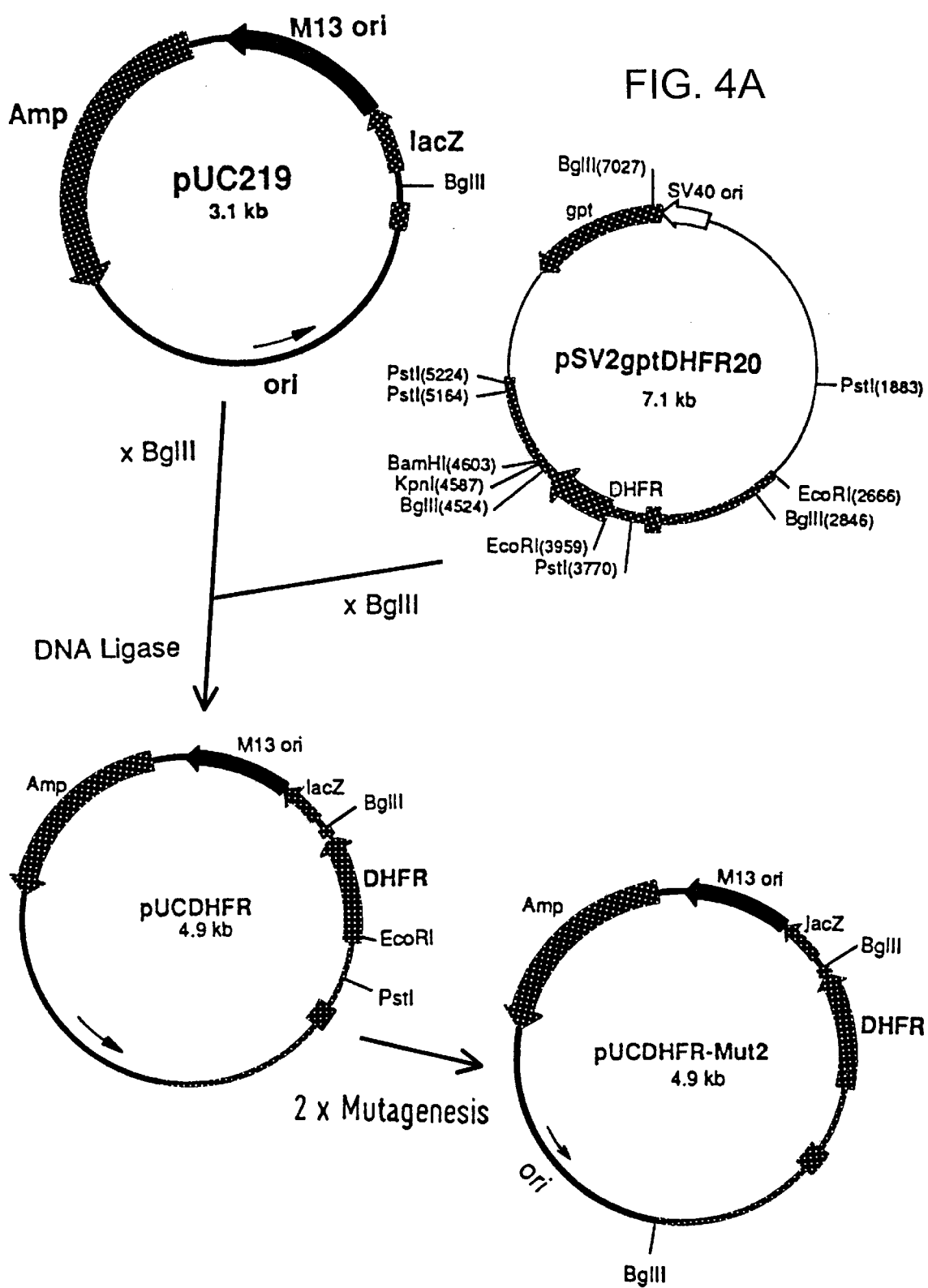
Figure 4B:
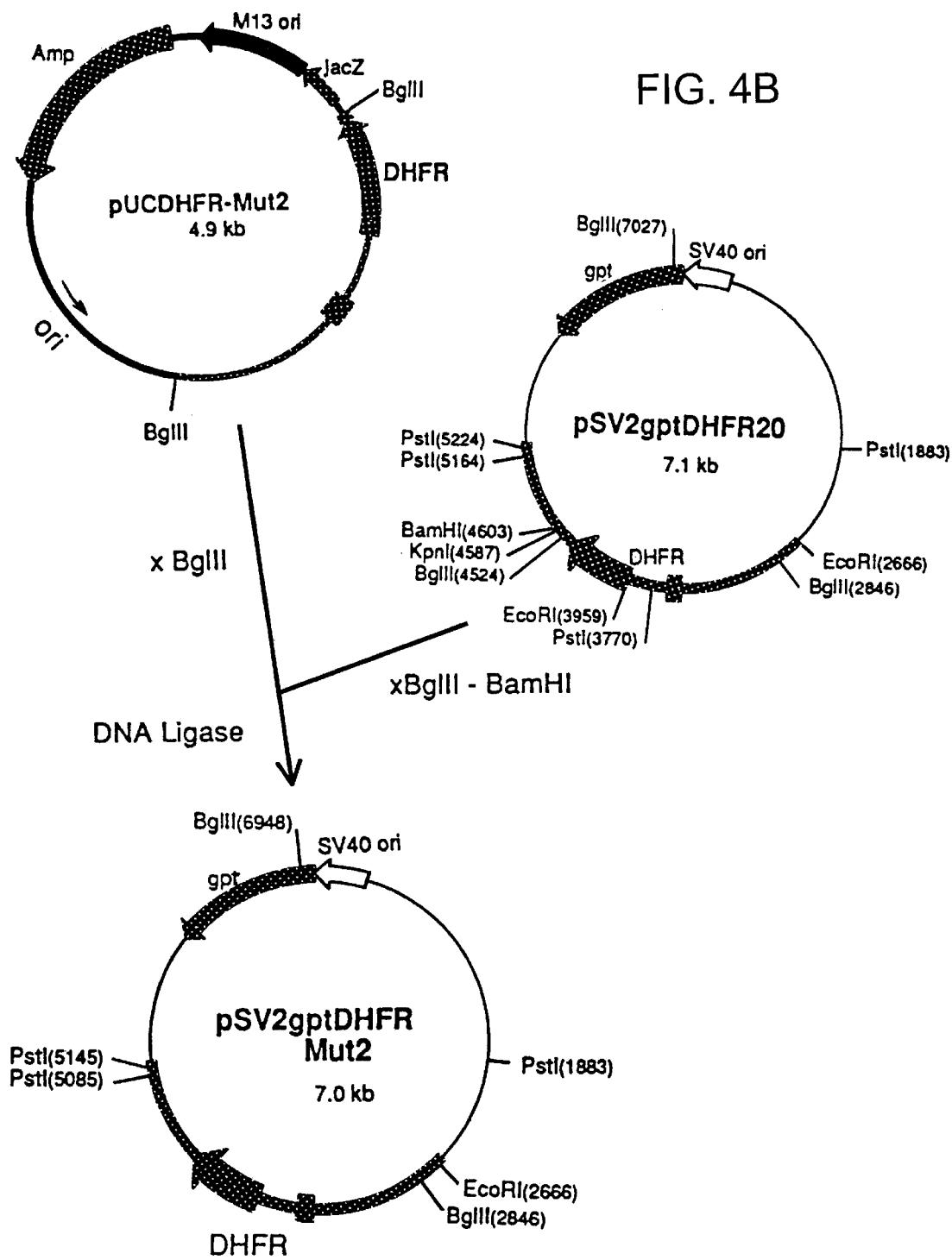

The plasmid pSV2gptDHFR-Mut2 (FIG. 4) was doubly cut with EcoRI and PstI and the DNA ends were blunted by 20 minutes' incubation at 11° C. with 5 units of T4 DNA polymerase (50 mM Tris HCl pH=8.0, 5 mM MgCl$_2$, 5 mM dithiothreitol, 0.1 mM of each of the four deoxynucleotide triphosphates and 50 μg/ml of bovine serum albumin). The 2.4 kb long DNA fragment with the mutated DHFR gene was isolated from an agarose gel and ligated with the pCMV-SV40 prepared as described above. A plasmid obtained after transformation of *E. coli* and containing the DHFR gene in the same orientation as the CMV promotor was designated pCMV-SV40DHFR.

In the last step the 0.4 kb stuffer fragment after the CMV promotor, which originated from the original plasmid pCDM8, was exchanged for a multicloning site. To do this, the plasmid pCMV-SV40DHFR was doubly cut with HindIII and XbaI and the vector part was isolated from an agarose gel. The multicloning site formed from the two oligonucleotides EBI-1823 (5'-AGCTTCTGCAGGTCGACATCGATGGATCCGGTA CCTCGAGCGGCCGCGAATTCT-3') and EBI-1829 (5'-CTAGAGAMTTCGCGGCCGCTCGAGGTACCGGA TCCATCGATGTCGACCTGCAGA-3'), contains, including the ends which are compatible for cloning in HindIII-XbaI, restriction cutting sites for the enzymes PstI, SalI, ClaI, BamHI, KpnI, XhoI, NotI and EcoRI.

1 μg of each of the two oligonucleotides was incubated for 1 hour at 37° C. in 20 μl of reaction buffer (70 mM Tris-Cl pH=7.6, 10 mM $MgCl_2$, 5 mM dithiothreitol, 0.1 mM ATP) with 5 units of T4 polynucleotide kinase in order to phosphorylate the 5' ends. The reaction was stopped by heating to 70° C. for 10 minutes and the complementary oligonucleotides were hybridized with one another by incubating the sample for a further 10 minutes at 56° C. and then slowly cooling it to ambient temperature. 4 μl of the hybridized oligonucleotides (100 ng) were ligated with about 100 ng of plasmid vector and *E. coli* HB101 was transformed. A plasmid which was capable of being linearized with the enzymes of the multicloning site (with the exception of NotI) was designed pAD-CMV1. Of a number of clones tested, it was not possible to identify any one the plasmids which could be cut with NotI. Sequencing always showed the deletion of some bases within the NotI recognition sequence.

In the same way, the expression plasmid pAD-CMV2 which contains the restriction cutting sites within the multicloning site in the reverse order was obtained with the oiigonucleotide pair EBI-1820 (5'-AGCTCTAGAGAATTCGCGGCCGCTCGAGGT ACCGGATCCATCGATGTCGACCTGCAGAAGCTTG-3') and EBI-1821 (5'-CTAGCAAGCTTCTGCAGGTCGACATCGATGGATC CGGTACCTCGAGCGGCCGCGAATTCTCTAG-3'). The plasmid pAD-CMV2 was obtained which was capable of being linearized with all the restriction enzymes, including NotI.

The nucleotide sequence of the 6414 bp plasmid pAD-CMV1 (FIG. 5) is shown in full in FIG. 6.

The sections of the plasmid (specified in the numbering of the bases) correspond to the following sequences:

| | |
|---|---|
| 1–21 | EBI-1733, beginning of CMV enhancer-promotor (from CDM8) |
| 632–649 | T7 promotor |
| 658–713 | Multicloning site (HindIII to XbaI from EBI-1823, EBI-1829) |
| 714–1412 | SV40 intron and poly-adenylation site (from CDM8) |
| 1413–2310 | 5'-non-coding region and promotor of the hamster DHFR gene (from pSV2gptDHFR20) |
| 2311–2396 | Hamster DHFR: Exon 1 |
| 2516 | A to T mutation destroys PstI site in DHFR intron 1 |
| 2701–3178 | DHFR Exons 2–6 (coding region) |
| 2707 | A to G mutation destroys EcoRI site |
| 3272–3273 | Deletion between BglII and BamHI in DHFR 3'-non-coding region |

| | |
|---|---|
| 3831 | End of DHFR gene (from pSV2gptDHFR20) |
| 3832–4169 | SV40 ori (from pSV2gptDHFR20) |
| 4170–4648 | M13 ori (from pBluescript Sk+) |
| 4780–5640 | β-lactamase (coding region) |
| 6395–6414 | EBI-1729, end of the pBluescript vector sequence |

Figure 5A:
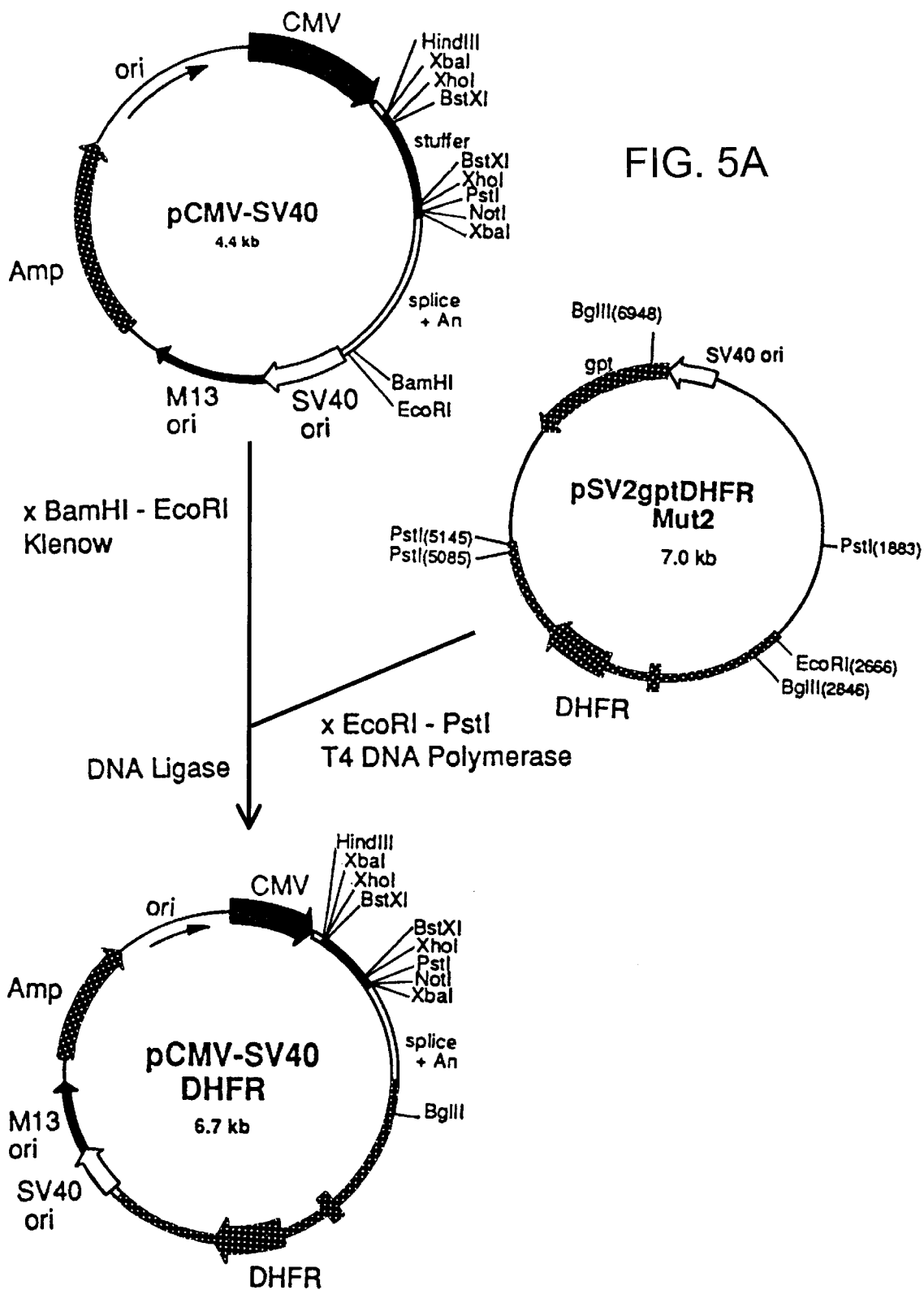
Figure 5B:
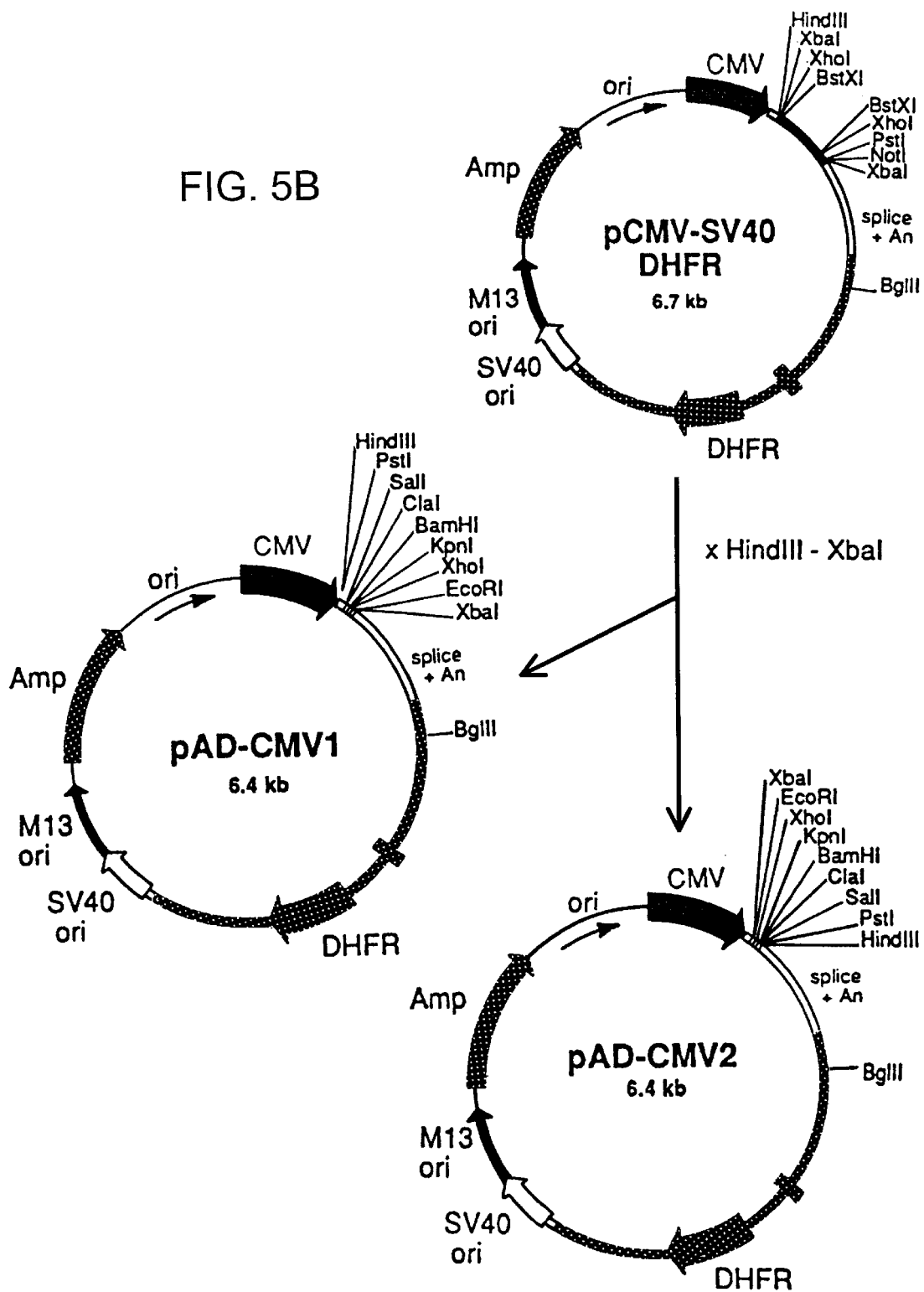

The preparation of the plasmids pAD-CMV1 and pAD-CMV2 is shown in FIG. 5.

EXAMPLE 13
Construction of the Plasmid PADTNF-BP for the Expression of the Soluble Form of TNF-BP In order to prepare the secreted form of TNF-BP by the direct method, a translation stop codon was inserted in the cDNA coding for part of the TNF receptor (see Example 11; hereinafter designated TNF-R cDNA) after the codon of the C-terminal amino acid of the natural TNF-BP (AAT, Asn-172; corresponding to position 201 in FIG. 9). In this way the protein synthesis is broken off at this point and makes it possible to secrete TNF-BP directly into the cell supernatant without having to undergo a subsequent reaction, which might possibly be rate determining of proteolytic cleaving of sections of the TNF receptor located in the C-terminal direction.

At the same time as the stop codon was inserted by PCR the 5'-non-coding region of the TNF-R cDNA was shortened in order to remove the translation start codon of another open reading frame (bases 72–203 in FIG. 9), which is located 5' from that of the TNF-R, and a BamHI or EcoRI cutting site is inserted at the 5' or 3'-end of the cDNA.

Figure 7A:
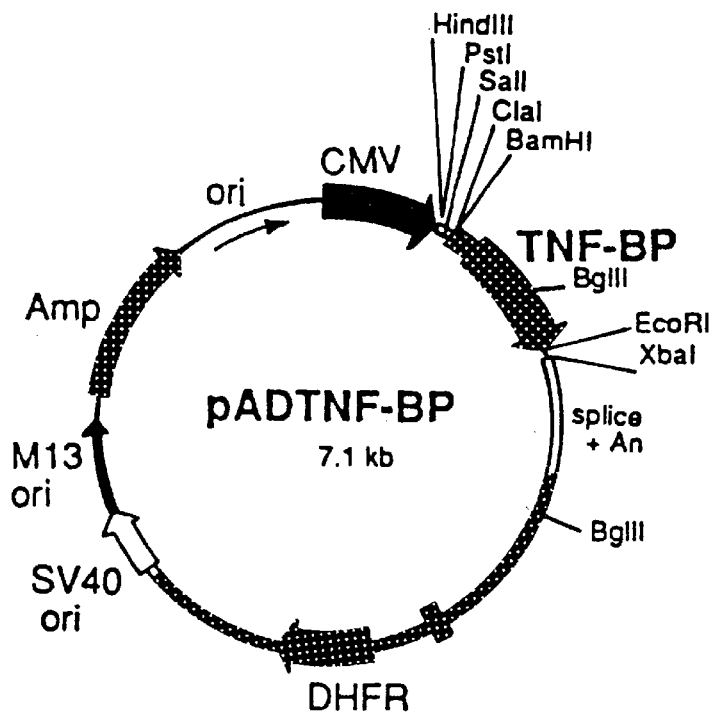

100 ng of plasmid pTNF-BP15 linearized with XmnI (see Example 11) were amplified with 50 pmol of oligonucleotides EBI-1986 (Sense, 5'-CAGGATCCGAGTCTCAACCCTCAAC-3') and EBI-1929 (Antisense, 5'-GGGAATTCCTTATCMTTCTCMTCTGGGGTAGGC ACMCTTC-3'; insertion of two stop codons and an EcoRI site) in a 100 μl PCR mixture over 10 cycles. The cycle conditions were 40 minutes at 94° C., 45 seconds at 55° C. and 5 minutes at 72° C. After the last cycle incubation was continued for a further 7 minutes at 72° C. ani the reaction was stopped by extracting with phenol chloroform. The DNA was precipitated with ethanol and then doubly cut with BamHI and EcoRI. The resulting 0.75 kb DNA fragment was isolated from an agarose gel and cloned into plasmid pT7/T3α-19 (BRL) doubly cut with BamHI and EcoRI. One of the plasmids obtained, which was found to have the desired sequence, when the entire insert was sequenced, was designated pTNF-BP.

pTNF-BP was cut with BamHI and EcoRI and the 0.75 kb DNA insert was cloned into the expression plasmid pAD-CMV1 cut with BamHI and EcoRI. A plasmid obtained with the desired composition was designated pADTNF-BP (FIG. 7A).

Figure 7B:
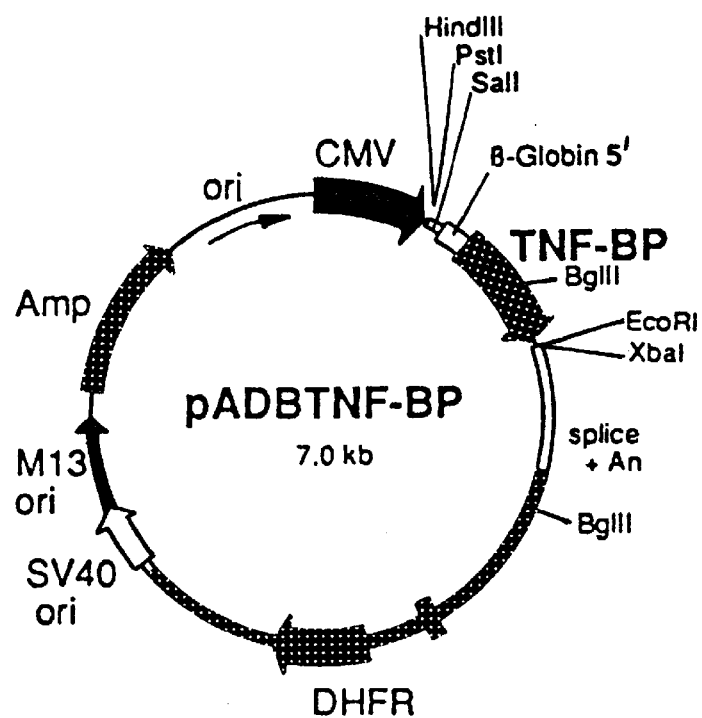

EXAMPLE 14
Construction of the Plasmid pADBTNF-BP for the Expression of the Soluble Form of TNF-BP For another variant of an expression plasmid for the production of secreted TNF-BP, the 5'-non-coding region of TNF-R cDNA was exchanged for the 5-non-coding region of human β-globin mRNA. The reason for this was the finding that the nucleotide sequence immediately before the translation start codon of the TNF-R sequence differs significantly from the concensus sequence found for efficient expression of eukaryotic genes (Kozak, 1987), whereas the 5'-non-coding region of the β-globin mRNA corresponds extremely well to this concensus sequence (Lawn et al., 1980). By means of the oligonucleotide EBI-2452 (5'-CACAGTCGACTTACATTTGCTTCTGACA-CAACTGTGTTCACTAGCMCCTCA AACAGACACCATGGGCCTCTCCACCGTGC-3'), which contained after a SalI restriction cutting site the authentic 5'-noncoding sequence, corresponding to the human β-globin mRNA sequence, followed by 20 bases of the coding region of TNF-BP, the TNF-R sequence was modified in a PCR. 100 ng of plasmid pTNF-BP linearized with EcoRI were amplified in 100 µl of reaction mixture with 50 pmol each of the oligonucleotides EBI-2452 and EBI-1922 (Antisense, 5'-GAGGCTGCAATTGAAGC3'; binds to the huTNF-R sequence at position 656) in 20 PCR cycles (40 seconds at 94° C., 45 seconds at 55° C., 90 seconds at 72° C.). After the PCR product has been purified by extraction with phenolchloroform and ethanol precipitation, the DNA was doubly cut with SalI and BglII and the resulting 0.51 kb DNA fragment was isolated from an agarose gel. The corresponding part of the TNF-R sequence was removed from the plasmid pTNF-BP by cutting with SalI and BglII, the 3.1 kb long plasmid portion was isolated from an agarose gel and ligated with the 0.51 kb long PCR product. After transformation of E. coli, seven of the resulting plasmids were sequenced. One of these plasmids contained precisely the desired sequence. This plasmid was designated pBTNF-BP. The entire SalI-EcoRI insert of pBTNF-BP was cloned into the similarly cut expression plasmid pAD-CMV1 and the resulting plasmid was designated pADBTNF-BP (FIG. 7B).

EXAMPLE 15
Isolation of Rat TNF-R cDNA Clones

First of all, rat brain cDNA was prepared analogously to the HS913T cDNA library (see Example 4) from the rat Glia tumour cells lines C6 (ATCC No. CCL107) in λ-gt11.

600,000 phages of the rat brain cDNA library in λgt11 were screened by hybridization as described in Example 6. The probe used was the purified EcoRI insert of pTNF-BP30 (cf. Example 6). About 100 ng of DNA were radioactively labelled with 1 µg of random hexamer primer instead of the specific oligonucleotides, as described in Example 6, using [α-$^{32}$P]dCTP. 25×10$^6$ cpm were incorporated. Hybridization of the filters was carried out under the same conditions as in Example 6. The filters were washed twice for 30 minutes at ambient temperature in 2×SSC/0.1% SDS and three times for 30 minutes at 65° C. in 2×SSC/0.1% SDS and twice for 30 minutes at 65° C. in 0.5×SSC/0.5% SDS. The air dried filters were then exposed to Kodak XAR X-ray film for 16 hours using an intensifier film at −70° C. A total of 10 hybridizing plaques were identified and separated by plaque purification. After plaque purification had been carried out three times, three λ clones (λ-raTNF-R Nos. 3, 4 and 8) were finally separated out and the phage DNA was prepared as described.

The length of the cDNA insert was determined after cutting the λ-DNA with EcoRI and separation in an agarose gel at 2.2 kb for the clones raTNF-R3 and raTNF-R8 and 2.1 kb for clone raTNF-R4. The EcoRI inserts of clones λraTNF-R3 and 8 were cloned into similarly cut M13mp19 and the DNA sequence was determined with universal sequencing primers and specifically synthesized oligonucleotide primers.

The complete nucleotide sequence of raTNF-R8 is shown in FIG. 8. The first and last seven bases correspond to the EcoRI linkers which had been added during the preparation of the cDNA library.

EXAMPLE 16
Isolation of a Clone Containing the Complete cDNA Coding for the Human TNF Receptor The complete cDNA of the rat TNF-R made it easier to search for the missing 3' part of human TNF-R cDNA. The probe used for the hybridization was the 0.4 kb long PCR product of the primers EBI-2316 (5'-ATTCGTGCGGCGCCTAG-3'; binds to TNF-R with the 2nd base of EcoRI, breaks off at the TNF-R cDNA) and EBI-2467 (5'GTCGGTAGCACCAAGGA-3'; binds about 400 bases before poly-A to cDNA clone, corresponds to position 1775 in raTNF-R) with λraTNF-R8 as starting material. This DNA fragment corresponds to the region of rat TNF-R cDNA which had been assumed to follow the internal EcoRI site in human TNF-R.

2.5×10$^6$ cpm of the raTNF-R probe were used to hybridize 600,000 plaques of the HS913T cDNA library. The hybridization conditions corresponded to those specified in Example 10. The filters were washed twice for 30 minutes at ambient temperature in 2×SSC/0.1% SDS and twice for 30 minutes at 65° C. in 2×SSC/0.1% SDS, dried in the air and exposed to Kodak XAR X-ray film using an intensifier film for a period of 3 days at −70° C. Six positive plaques were identified purified to two further rounds of plaques and λ-DNA was prepared (λTNF-R Nos. 2, 5, 6, 8, 11 and 12). After the λ-DNA had been cut with EcoRI all the clones had a DNA band about 0.8 kb long. λ-TNF-R2 and 11 additionally contained an EcoRI fragment of 1.3 kb. The two EcoRI inserts from λTNF-R2 were subcloned into the EcoRI site of plasmid pUC218 (IBI) and then sequenced. The sequence of the 1.3 kb EcoRI fragment corresponded to that of cDNA clone pTNF-BP15, the 0.8 kb EcoRI fragment corresponds to the 3' part of TNF-R mRNA and contains, in front of the EcoRI linker sequence, a poly-A tail with 16 A residues. λTNF-R2 therefore contains the complete coding region for human TNF-R, shown in FIG. 9.

EXAMPLE 17
Construction of the Plasmids pADTNF-R and PADBTNF-R for Expression of the Entire Human TNF Receptor First of all, as described in Example 13 for pTNF-BP or pADTNF-BP, a plasmid was constructed in which the 5' non-coding region of pTNF-BP15 had been shortened, but, unlike the plasmids described in Example 13, the 3'-end of pTNF-BP15 had been kept. For this purpose, under identical conditions to those described in Example 13, pTNF-BP15 was amplified with PCR using the oligonucleotide EBI-1986 and the M13-40 universal primer (5'-GTTTTCCCAGTCACGAC-3'). The PCR product was doubly cut with BamHI and EcoRI and cloned into the plasmid pT7/T3α-19. One of the plasmids obtained was designated pTNF-BP15B.

pTNF-BP15B was cut with BamHI and EcoRI and the 1.26 kb DNA insert was cloned into expression plasmid pAD-CMV1 cut with BamHI and EcoRI. A plasmid of the desired composition thus obtained was designated pADTNFBP15.

Figure 7C:
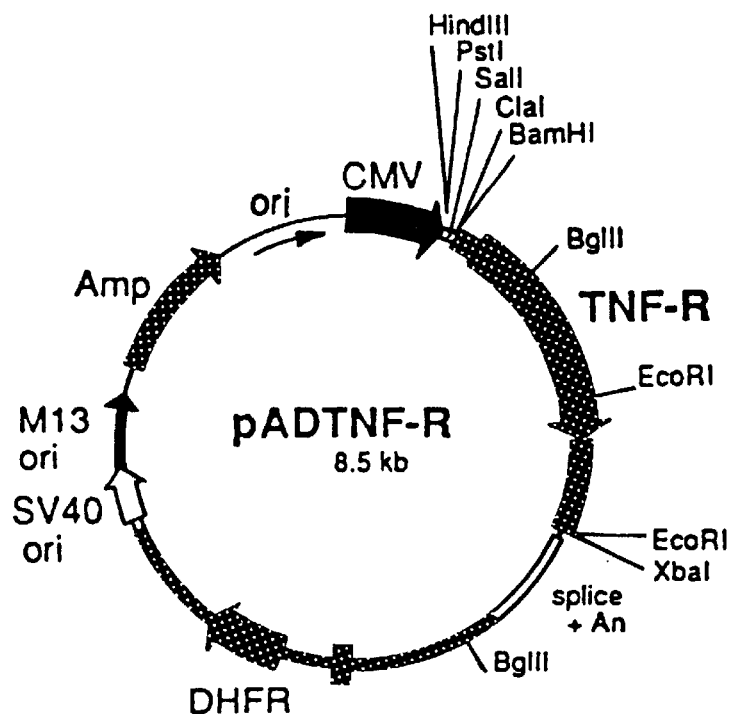

This plasmid was linearized with EcoRI and the 0.8 kb EcoRI fragment isolated from λTNF-R2 was cloned into the cutting site. After transformation of E. coli, a few randomly isolated plasmids were checked, by cutting with various restriction enzymes, for the correct orientation of the EcoRI fragment used. A plasmid designated pADTNF-R (FIG. 7C) was investigated more accurately for correct orientation by sequencing the insert, starting from the 3'-end of the inserted cDNA with the oligonucleotide EBI-2112 (5'GTCCAATTATGTCACACC-3'), which binds to the plasmid pAD-CMV1 and its derivatives after the multicloning site.

Figure 7D:
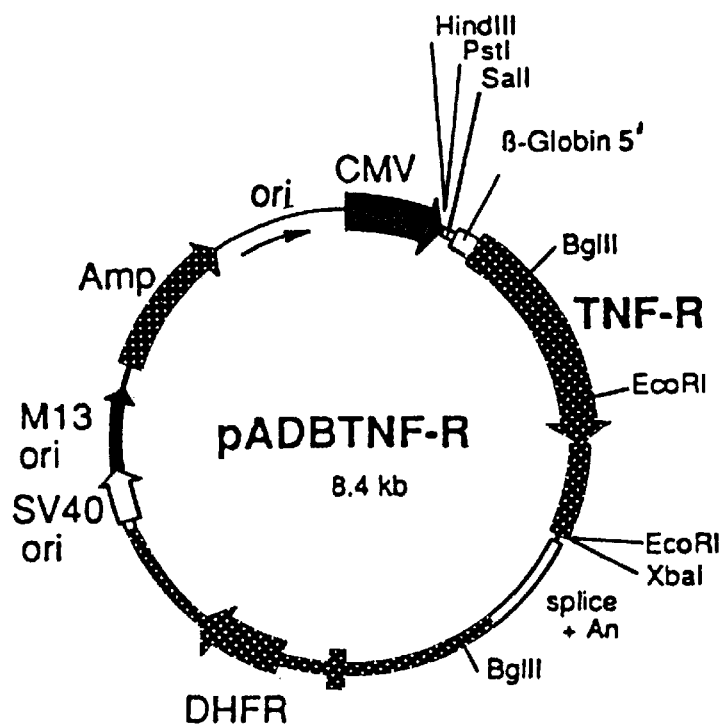

Another expression plasmid in which the 5'-noncoding region of the TNF-R is exchanged for that of β-globin was constructed. Plasmid pADBTNF-BP was cut completely in order to remove the 1.1 kb BglII fragment, the DNA ends were then dephosphorylated with calves' intestinal alkaline phosphatase and the plasmid vector (5.9 kb) with the β-globin 5'-non-coding region of the β-globin gene and the 5' part of the TNF-R coding region was isolated from an agarose gel. Plasmid pADTNF-R was cut with BglII and the 2.5 kb DNA fragment containing the 3' section of the TNF-R cDNA as far as the promotor region of the following DHFR gene, was isolated from an agarose gel and cloned into the plasmid vector which had been prepared beforehand. A plasmid obtained after transformation of E. coli having the BglII fragment inserted in the correct orientation was designated pADBTNF-R (FIG. 7D).

EXAMPLE 19
Expression of Soluble TNF-BP in Eukaryotic Cell Lines a) ELISA test In this Example TNF-BP was detected by the ELISA test as follows:

96 well microtitre plates were coated in each well with 50 µl of 1:3000 diluted polyclonal rabbit serum (polyclonal rabbit antibodies, prepared by precipitation of antiserum with ammonium sulphate, final concentration 50% saturation) against natural TNF-BP for 18 hours at 4° C., washed once with 0.05% Tween 20 in PBS and free binding sites were blocked with 150 to 200 µl of 0.5% bovine serum albumin, 0.05% Tween 20 in PBS (PBS/BSS/Tween) for one hour at ambient temperature. The wells were washed once with 0.05% Tween 20 in PBS and 50 µl of cell supernatant or known quantities of natural TNF-BP (see Tables 3 and 4) and 50 µl of a 1:10,000-fold dilution of a polyclonal mouse serum against TNF-BP was applied and incubated for two hours at ambient temperature. Then the wells were washed three times with 0.05% Tween 20 in PBS and 50 µl of rabbit anti-mouse Ig-peroxidase conjugate (Dako P161; 1:5000 in PBS/BSA/Tween) were added and incubation was continued for a further two hours at ambient temperature. The wells were washed three times with Tween/PBS and the staining reaction was carried out with orthophenylenediamine (3 mg/ml) and Naperborate (1 mg/ml) in 0.067M potassium citrate, pH 5.0, 100 µl per well, for 20 minutes at ambient temperature away from the light. After the addition of 100 µl of 4N H2SO4 the color intensity at a wavelength of 492 nm was measured photometrically in a microfilm plate photometer.

b) Transient expression of soluble TNF-BP in eukaryotic cell lines

About 106 cells (COS-7) per 80 mm petri dish were mixed with 10% heat inactivated fetal calves' serum 24 hours before transfection in RPMI-1640 medium and incubated at 37° C. in a 5% CO2 atmosphere. The cells were separated from the petri dish using a rubber spatula and centrifuged for 5 minutes at 1200 rpm at ambient temperature (Heraeus minifuge, swing-out rotor 3360), washed once with 5 ml of serum-free medium, centrifuged for 5 minutes at 1200 rpm and suspended in 1 ml of medium mixed with 250 µg/ml of DEAE dextran and 10 µg of plasmid DNA (see Table 3), purified by carrying out CsCl density gradient centrifugation twice). The cells were incubated for 40 minutes at 37° C., washed once with 5 ml of medium containing 10% calves' serum and suspended in 5 ml of medium with 100 µg/ml of chloroquin. The cells were incubated for one hour at 37° C., washed once with medium and incubated with 10 ml of fresh medium at 37° C. After 72 hours the cell supernatant was harvested and used to detect the secreted TNF-BP.

TABLE 3

| Cell line | COS-7 |
|---|---|
| without plasmid | <5 ng/ml |
| pADTNF-BP | 7.5 ng/ml |
| pADBTNF-BP | 146 ng/ml | c) Preparations of cell lines which permanently produce TNF-BP

The dihydrofolate reductase (DHFR)-deficient hamster ovarial cell line CHO DUKX BII (Urlaub and Chasin, 1980) was transfected with plasmid pADBTNF-BP by calcium phosphate precipitation (Current Protocols in Molecular Biology, 1987). Four thickly grown cell culture flasks (25 cm$^2$, 5 ml of culture medium per flask) were transfected with 5 µg of DNA; after four hours incubation at 37° C. the medium was removed and replaced by 5 ml of selection medium (MEM alpha medium with 10% dialyzed fetal calves' serum). After incubation overnight the cells were detached using trypsin solution; the cells from each flask were divided between two 96-well tissue culture plates (100 µl per well in selection medium). Fresh medium was added at about weekly intervals. After about four weeks cell clones could be observed in 79 wells. The supernatants were tested for TNF-BP activity by the ELISA test. 37 supernatants showed activity in ELISA. The results of the ELISA test of some positive clones are shown in Table 4.

TABLE 4

| Sample | Absorption at 492 nm |
|---|---|
| TNF-BP Standard | |
| 1 ng/ml | 0.390 |
| 10 ng/ml | 1.233 |
| 100 ng/ml | 1.875 |
| Culture medium (negative control) | 0.085 |
| Clone | |
| A1G3 | 0.468 |
| A2F5 | 0.931 |
| A3A12 | 0.924 |
| A4B8 | 0.356 |
| A5A12 | 0.806 |
| A5B10 | 0.915 |
| A5C1 | 0.966 |

EXAMPLE 20
RNA Analysis (Northern Blot) of the Human TNF Receptor

1 µg of poly-A+ RNA (isolated from HS913T (fibrosarcoma)), placenta and spleen were separated by electrophoresis in a 1.5% vertical agarose gel (10 mM Na phosphate buffer pH=7.0, 6.7% formaldehyde). The size marker used was a kilobase ladder radioactively labelled by a fill-in reaction with ($\alpha$-$^{32}$P)dCTP and Klenow enzyme (Bethesda Research Laboratories). The formaldehyde was removed from the gel by irrigation and the RNA was transferred in 20× SSC to a nylon membrane (Genescreen plus, NEN-DuPont). The RNA was covalently bonded on the membrane by UV irradiation (100 seconds). The membrane was prehybridized for 2 hours at 65° C. in Church buffer (Church and Gilbert, 1984) (0.5 M Na-phosphate pH=7.2, 7% SDS, 1 mM EDTA) and hybridized for 19 hours at 65° C. in fresh Church buffer with 3×10$^6$ cpm P-32 labelled DNA probe (EcoRI insert of pTNF-BP30). The filter was washed three times for 10 minutes at ambient temperature in washing buffer (40 mM Na phosphate pH=7.2, 1% SDS) and then four times for 30 minutes at 65° C. in washing buffer and exposed to Kodak XAR X-ray film for 18 hours using an intensifier film at −70° C.

Figure 10:
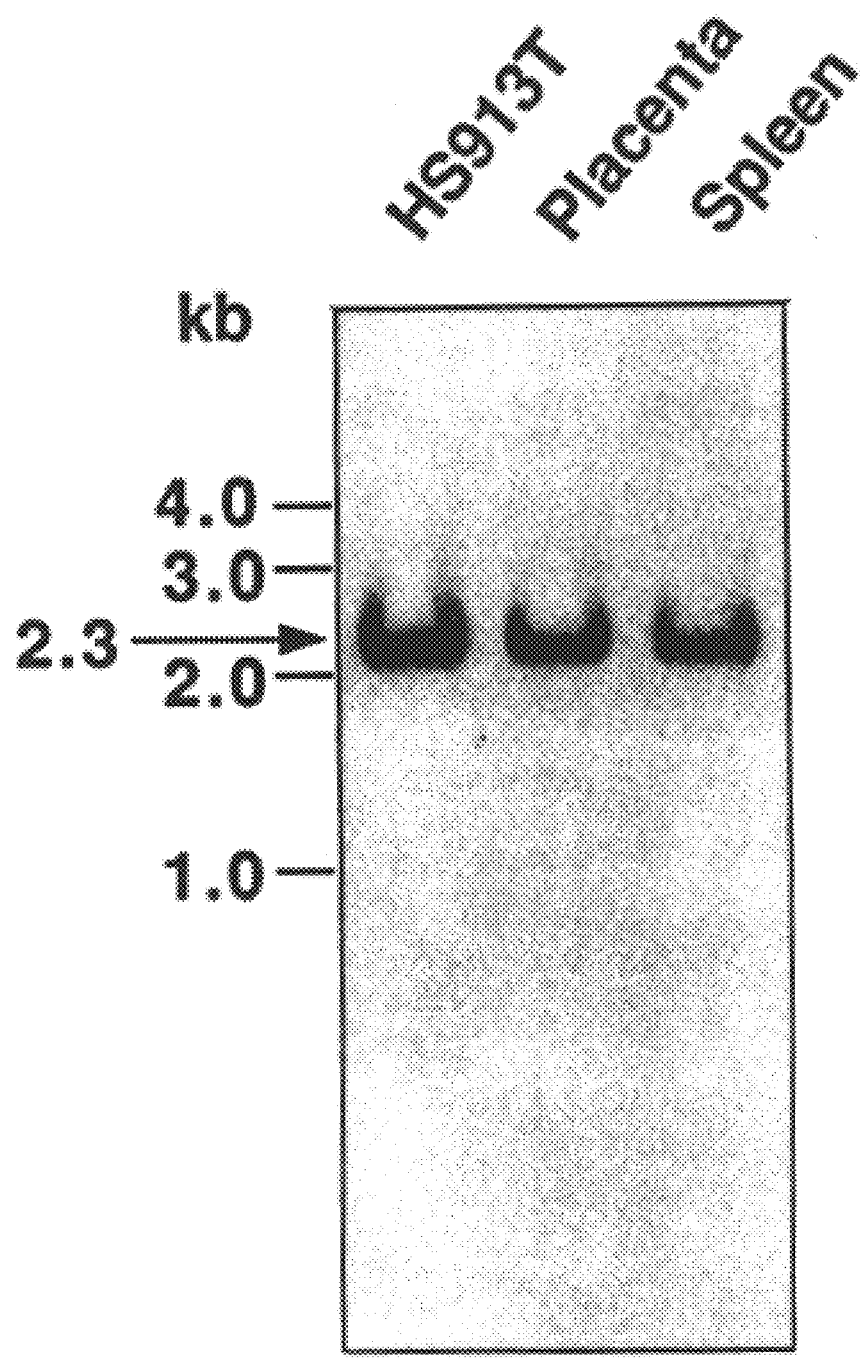

The autoradiogram (FIG. 10) shows a singular RNA band with a length of 2.3 kb for the human TNF receptor in the analyzed tissues or cell line HS913T.

EXAMPLE 21

Expression of the TNF Receptor

For transient expression 5–10×10⁷ COS-7 cells were incubated for 40 minutes with 10 μg of pADTNF-R plasmid DNA in a solution containing 250 μg/mi of DEAE dextran and 50 μg/ml of chloroquin. pADCMV-1-DNA was used as control. After transfection the cells were washed and then cultured for 48 hours. The expression of the TNF receptor was demonstrated by the binding ¹²⁵I-TNF. For the binding tests the cells were washed, incubated for one hour at 4° C. with 10 mg of ¹²⁵I-TNF (specific radioactivity 38,000 cpm/ng) with or without a 200 fold excess of unlabelled TNF and the radioactivity bound to the cells was measured in a gamma-counter. The specific binding in the control sample was 2062 cpm and in the samples transformed with TNF receptor DNA it was 6150 cpm (the values are expressed as the average bound cpm; the standard deviation determined from parallel tests is taken into account. The non-specific background in the presence of unlabelled TNF was subtracted from the values).

We claim:

1. An isolated DNA molecule coding for a polypeptide having the ability to bind TNF, wherein said polypeptide is selected from the group consisting of:

A) a polypeptide comprising the amino acid sequence:

```
asp ser val cys pro gln gly lys tyr ile his pro gln
asn asn ser ile cys cys thr lys cys his lys gly thr
tyr leu tyr asn asp cys pro gly pro gly gln asp thr
asp cys arg glu cys glu ser gly ser phe thr ala ser
glu asn his leu arg his cys leu ser cys ser lys cys
arg lys glu met gly gln val glu ile ser ser cys thr
val asp arg asp thr val cys gly cys arg lys asn gln
tyr arg his tyr trp ser glu asn leu phe gln cys phe
asn cys ser leu cys leu asn gly thr val his leu ser
cys gln glu lys gln asn thr val cys thr cys his ala
gly phe phe leu arg glu asn glu cys val ser cys ser
asn cys lys lys ser leu glu cys thr lys leu cys leu
pro gln ile glu asn
```

B) a polypeptide comprising the amino acid sequence:

```
leu val pro his leu gly asp arg glu lys arg asp
ser val cys pro gln gly lys tyr ile his pro gln
asn asn ser ile cys cys thr lys cys his lys gly
thr tyr leu tyr asn asp cys pro gly pro gly gln
asp thr asp cys arg glu cys glu ser gly ser phe
thr ala ser glu asn his leu arg his cys leu ser
cys ser lys cys arg lys glu met gly gln val glu
ile ser ser cys thr val asp arg asp thr val cys
gly cys arg lys asn gln tyr arg his tyr trp ser
glu asn leu phe gln cys phe asn cys ser leu cys
leu asn gly thr val his leu ser cys gln glu lys
gln asn thr val cys thr cys his ala gly phe phe
leu arg glu asn glu cys val ser cys ser asn cys
lys lys ser leu glu cys thr lys leu cys leu pro
gln ile glu asn
```

C) a polypeptide comprising the amino acid sequence:

```
asp ser val cys pro gln gly lys tyr ile his pro
gln asn asn ser ile cys cys thr lys cys his lys
```

-continued
```
gly thr tyr leu tyr asn asp cys pro gly pro gly
gln asp thr asp cys arg glu cys glu ser gly ser
phe thr ala ser glu asn his leu arg his cys leu
ser cys ser lys cys arg lys glu met gly gln val
glu ile ser ser cys thr val asp arg asp thr val
cys gly cys arg lys asn gln tyr arg his tyr trp
ser glu asn leu phe gln cys phe asn cys ser leu
cys leu asn gly thr val his leu ser cys gln glu
lys gln asn thr val cys thr cys his ala gly phe
phe leu arg glu asn glu cys val ser cys ser asn
cys lys lys ser leu glu cys thr lys leu cys leu
pro gln ile glu asn val lys gly thr glu asp ser
gly thr thr
``` and

D) a polypeptide comprising the amino acid sequence:

```
leu val pro his leu gly asp arg glu lys arg asp
ser val cys pro gln gly lys tyr ile his pro gln
asn asn ser ile cys cys thr lys cys his lys gly
thr tyr leu tyr asn asp cys pro gly pro gly gln
asp thr asp cys arg glu cys glu ser gly ser phe
thr ala ser glu asn his leu arg his cys leu ser
cys ser lys cys arg lys glu met gly gln val glu
ile ser ser cys thr val asp arg asp thr val cys
gly cys arg lys asn gln tyr arg his tyr trp ser
glu asn leu phe gln cys phe asn cys ser leu cys
leu asn gly thr val his leu ser cys gln glu lys
gln asn thr val cys thr cys his ala gly phe phe
leu arg glu asn glu cys val ser cys ser asn cys
lys lys ser leu glu cys thr lys leu cys leu pro
gln ile glu asn val lys gly thr glu asp ser gly
thr thr
```

E) a polypeptide comprising the amino acid sequence of A, B, C or D with at least one conservative amino acid substitution;

F) a polypeptide comprising the amino acid sequence of A, B, C or D with at least one amino acid substitution at a glycosylation site;

G) a polypeptide comprising the amino acid sequence of A, B, C or D with at least one amino acid substitution at a proteolytic cleavage site; and H) a polypeptide comprising the amino acid sequence of A, B, C or D with at least one amino acid substitution at a cysteine residue.

2. An isolated DNA molecule coding for a polypeptide having the ability to bind TNF selected from the group consisting of:

A) a polypeptide comprising the amino acid sequence:

```
met asp ser val cys pro gln gly lys tyr ile his pro gln asn asn ser ile cys cys thr lys cys his lys gly thr tyr leu tyr asn asp cys pro gly pro gly gln asp thr asp cys arg glu cys glu ser gly ser phe thr ala ser glu asn his leu arg his cys leu ser cys ser lys cys arg lys glu met gly gln val glu ile ser ser cys thr val asp arg asp thr val cys gly cys arg lys asn gln tyr arg his tyr trp ser glu asn leu phe gln cys phe asn cys ser leu cys leu asn gly thr val his leu ser cys gln glu lys gln asn thr val cys thr cys his
```

-continued ala gly phe phe leu arg glu asn glu cys val ser cys ser asn cys lys lys ser leu glu cys thr lys leu cys leu pro gln ile glu asn B) a polypeptide comprising the amino acid sequence:

met leu val pro his leu gly asp arg g-
lu lys arg asp ser val cys pro gln gly lys tyr ile-
his pro gln asn asn ser ile cys cys thr lys cy-
s his lys gly thr tyr leu tyr asn asp cys progly pro gly gln asp thr asp cys arg glu cys glu ser gly ser phe t-
hr ala ser glu asn his leu arg his cys leu ser cys-
ser lys cys arg lys glu met gly gln val glu-
ile ser ser cys thr val asp arg asp thr val cys gly cys ar-
g lys asn gln tyr arg his tyr trp ser glu asn le-
u phe gln cys phe asn cys ser leu cys leu asn gly thr val-
his leu ser cys gln glu lys gln asn thr val cys thr-
cys his ala gly phe phe leu arg glu asn glu cys-
val ser cys ser as -continued gln tyr arg his tyr trp ser glu asn leu phe gln cys
phe asn cys ser leu cys leu asn gly thr val his leu
ser cys gln glu lys gln asn thr val cys thr cys his
ala gly phe leu arg glu asn glu cys val ser cys
ser asn cys lys lys ser leu glu cys thr lys leu cys
leu pro gln ile glu asn F) a polypeptide comprising the amino acid sequence:

met gly leu ser thr val pro asp leu leu leu pro leu
val leu leu glu leu leu val gly ile tyr pro ser gly
val ile gly leu val pro his leu gly asp arg glu lys
arg asp ser val cys pro gln gly lys tyr ile his pro
gln asn asn ser ile cys cys thr lys cys his lys gly
thr tyr leu tyr asn asp cys pro gly pro gly gln asp
thr asp cys arg glu cys glu ser gly ser phe thr ala
ser glu asn his leu arg his cys leu ser cys ser lys
cys arg lys glu met gly gln val glu ile ser ser cys
thr val asp arg asp thr val cys gly cys arg lys asn
gln tyr arg his tyr trp ser glu asn leu phe gln cys
phe asn cys ser leu cys leu asn gly thr val his leu
ser cys gln glu lys gln asn thr val cys thr cys his
ala gly phe leu arg glu asn glu cys val ser cys
ser asn cys lys lys ser leu glu cys thr lys leu cys
leu pro gln ile glu asn val lys gly thr glu asp ser
gly thr thr G) a polypeptide comprising the amino acid sequence:

met gly leu ser thr val pro asp leu leu leu pro
leu val leu leu glu leu leu val gly ile tyr pro
ser gly val ile gly asp ser val cys pro gln gly
lys tyr ile his pro gln asn asn ser ile cys cys
thr lys cys his lys gly thr tyr leu tyr asn asp
cys pro gly pro gly gln asp thr asp cys arg glu
cys glu ser gly ser phe thr ala ser glu asn his
leu arg his cys leu ser cys ser lys cys arg lys
glu met gly gln val glu ile ser ser cys thr val
asp arg asp thr val cys gly cys arg lys asn gln
tyr arg his tyr trp ser glu asn leu phe gln cys
phe asn cys ser leu cys leu asn gly thr val his
leu ser cys gln glu lys gln asn thr val cys thr cys his ala gly phe phe leu arg glu asn glu cys
val ser cys ser asn cys lys lys ser leu glu cys
thr lys leu cys leu pro gln ile glu asn H) a polypeptide comprising the amino acid sequence:

met gly leu ser thr val pro asp leu leu leu pro leu
val leu leu glu leu leu val gly ile tyr pro ser gly
val ile gly asp ser val cys pro gln gly lys tyr ile
his pro gln asn asn ser ile cys cys thr lys cys his
lys gly thr tyr leu tyr asn asp cys pro gly pro gly
gln asp thr asp cys arg glu cys glu ser gly ser phe
thr ala ser glu asn his leu arg his cys leu ser cys
ser lys cys arg lys glu met gly gln val glu ile ser
ser cys thr val asp arg asp thr val cys gly cys arg
lys asn gln tyr arg his tyr trp ser glu asn leu phe
gln cys phe asn cys ser leu cys leu asn gly thr val
his leu ser cys gln glu lys gln asn thr val cys thr
cys his ala gly phe phe leu arg glu asn glu cys val
ser cys ser asn cys lys lys ser leu glu cys thr lys
leu cys leu pro gln ile glu asn val lys gly thr glu
asp ser gly thr thr and I) a polypeptide comprising the amino acid sequence:

met gly leu ser thr val pro asp leu leu leu pro leu
val leu leu glu leu leu val gly ile tyr pro ser gly
val ile gly leu val pro his leu gly asp arg glu lys
arg asp ser val cys pro gln gly lys tyr ile his pro
gln asn asn ser ile cys cys thr lys cys his lys gly
thr tyr leu tyr asn asp cys pro gly pro gly gln asp
thr asp cys arg glu cys glu ser gly ser phe thr ala
ser glu asn his leu arg his cys leu ser cys ser lys
cys arg lys glu met gly gln val glu ile ser ser cys -continued thr val asp arg asp thr val cys gly cys arg lys asn gln tyr arg his tyr trp ser glu asn leu phe gln cys phe asn cys ser leu cys leu asn gly thr val his leu ser cys gln glu lys gln asn thr val cys thr cys his ala gly phe phe leu arg glu asn glu cys val ser cys ser asn cys lys lys ser leu glu cys thr lys leu cys leu pro gln ile glu asn val lys gly thr glu asp ser gly thr thr val leu leu pro leu val ile phe phe gly leu cys leu leu ser leu leu phe ile gly leu met tyr arg tyr gln arg trp lys ser lys leu tyr ser ile val cys gly lys ser thr pro glu lys glu gly glu leu glu gly thr thr thr lys pro leu ala pro asn pro ser phe -continued ser pro thr pro gly phe thr pro thr leu gly phe ser pro val pro ser ser thr phe thr ser ser ser thr tyr thr pro gly asp cys pro asn phe ala ala pro arg arg glu val ala pro pro tyr gln gly ala asp pro ile leu ala thr ala leu ala ser asp pro ile pro asn pro leu gln lys trp glu asp ser ala his lys pro gln ser leu asp thr asp asp pro ala thr leu tyr ala val val glu asn val pro pro leu arg trp lys glu phe val arg arg leu gly leu ser asp his glu ile asp arg leu glu leu -continued gln asn gly arg cys leu arg glu ala gln tyr ser met leu ala thr trp arg arg arg thr pro arg arg glu ala thr leu glu leu leu gly arg val leu arg asp met asp leu leu gly cys leu glu asp ile glu glu ala leu cys gly pro ala ala leu pro pro ala pro ser leu leu arg I) a polypeptide comprising the amino acid sequence of A, B, C, D, E, F, G, H or I with at least one conservative amino acid substitution;

J) a polypeptide comprising the amino acid sequence of A, B, C, D, E, F, G, H or I with at least one amino acid substitution at a glycosylation site;

K) a polypeptide comprising the amino acid sequence of A, B, C, D, E, F, G, H or I with at least one amino acid substitution at a proteolytic cleavage site; and L) a polypeptide comprising the amino acid sequence of A, B, C, D, E, F, G, H or I with at least one amino acid substitution at a cysteine residue.

3. An isolated DNA molecule, wherein said DNA is selected from the group consisting of:
A) DNA comprising the sequence:
B) DNA comprising the sequence:

CTG GTC CCT CAC CTA GGG GAC AGG GAG AAG AGA GAT AGT

GTG TGT CCC CAA GGA AAA TAT ATC CAC CCT CAA AAT AAT

TCG ATT TGC TGT ACC AAG TGC CAC AAA GGA ACC TAC TTG

TAC AAT GAC TGT CCA GGC CCG GGG CAG GAT ACG GAC TGC

AGG GAG TGT GAG AGC GGC TCC TTC ACC GCT TCA GAA AAC

CAC CTC AGA CAC TGC CTC AGC TGC TCC AAA TGC CGA AAG

GAA ATG GGT GAC GTG GAG ATC TCT TCT TGC ACA GTG GAC

CGG GAC ACC GTG TGT GGC TGC AGG AAG AAC CAG TAC CGG

CAT TAT TGG AGT GAA AAC CTT TTC CAG TGC TTC AAT TGC

AGC CTC TGC CTC AAT GGG ACC GTG CAC CTC TCC TGC CAG

GAG AAA CAG AAC ACC GTG TGC ACC TGC CAT GCA GGT TTC TTT

CTA AGA GAA AAC GAG TGT GTC TCC TGT AGT AAC TGT

AAG AAA AGC CTG GAG TGC ACG AAG TTG TGC CTA CCC CAG

ATT GAG AAT

CTG GTC CCT CAC CTA GGG GAC AGG GAG AAG AGA GAT AGT

GTG TGT CCC CAA GGA AAA TAT ATC CAC CCT CAA AAT AAT

TCG ATT TGC TGT ACC AAG TGC CAC AAA GGA ACC TAC TTG

TAC AAT GAC TGT CCA GGC CCG GGG CAG GAT ACG GAC TGC

AGG GAG TGT GAG AGC GGC TCC TTC ACC GCT TCA GAA AAC

CAC CTC AGA CAC TGC CTC AGC TGC TCC AAA TGC CGA AAG

GAA ATG GGT GAC GTG GAG ATC TCT TCT TGC ACA GTG GAC

CGG GAC ACC GTG TGT GGC TGC AGG AAG AAC CAG TAC CGG

CAT TAT TGG AGT GAA AAC CTT TTC CAG TGC TTC AAT TGC

AGC CTC TGC CTC AAT GGG ACC GTG CAC CTC TCC TGC CAG

GAG AAA CAG AAC ACC GTG TGC ACC TGC CAT GCA GGT TTC TTT

CTA AGA GAA AAC GAG TGT GTC TCC TGT AGT AAC TGT AAG

AAA AGC CTG GAG TGC ACG AAG TTG TGC CTA CCC CAG ATT

GAG AAT GTT AAG GGC ACT GAG GAC TCA GGC ACC ACA

C) DNA comprising the sequence:

GAT AGT GTG TGT CCC CAA GGA AAA TAT ATC CAC CCT CAA

AAT AAT TCG ATT TGC TGT ACC AAG TGC CAC AAA GGA ACC

TAC TTG TAC AAT GAC TGT CCA GGC CCG GGG CAG GAT ACG

GAC TGC AGG GAG TGT GAG AGC GGC TCC TTC ACC GCT TCA

GAA AAC CAC CTC AGA CAC TGC CTC AGC TGC TCC AAA TGC

CGA AAG GAA ATG GGT CAG GTG GAG ATC TCT TCT TGC ACA

GTG GAC CGG GAC ACC GTG TGT GGC TGC AGG AAG AAC CAG

TAC CGG CAT TAT TGG AGT GA

-continued

CGG CAT TAT TGG AGT GAA AAC CTT TTC CAG TGC TTC AAT

TGC AGC CTC TGC CTC AAT GGG ACC GTG CAC CTC TCC TGC

CAG GAG AAA CAG AAC ACC GTG TGC ACC TGC CAT GCA GGT

TTC TTT CTA AGA GAA AAC GAG TGT GTC TCC TGT AGT AAC

TGT AAG AAA AGC CTG GAG TGC ACG AAG TTG TGC CTA CCC

CAG ATT GAG AAT

B) DNA comprising the sequence:

ATG CTG GTC CCT CAC CTA GGG GAC AGG GAG AAG AGA GAT

AGT GTG TGT CCC CAA GGA AAA TAT ATC CAC CCT CAA AAT

AAT TGC ATT TGC TGT ACC AAG TGC CAC AAA GGA ACC TAC

TTG TAC AAT GAC TGT CCA GGC CCG GGG CAG GAT ACG GAC

TGC AGG GAG TGT GAG AGC GGC TCC TTC ACC GCT TCA GAA

AAC CAC CTC AGA CAC TGC CTC AGC TGC TCC AAA TGC CGA

AAG GAA ATG GGT CAG GTG GAG ATC TCT TCT TGC ACA GTG

GAC CGG GAC ACC GTG TGT GGC TGC AGG AAG AAC CAG TAC

CGG CAT TAT TGG AGT GAA AAC CTT TTC CAG TGC TTC AAT

TGC AGC CTC TGC CTC AAT GGG ACC GTG CAC CTC TCC TGC

CAG GAG AAA CAG AAC ACC GTG TGC ACC TGC CAT GCA GGT

TTC TTT CTA AGA GAA AAC GAG TGT GTC TCC TGT AGT AAC

TGT AAG AAA AGC CTG GAG TGC ACG AAG TTG TGC CTA CCC

CAG ATT GAG AAT GTT AAG GGC ACT GAG GAC TCA GGC ACC

ACA

C) DNA comprising the sequence:

ATG GAT AGT GTG TGT CCC CAA GGA AAA TAT ATC CAC CCT

CAA AAT AAT TCG ATT TGC TGT ACC AAG TGC CAC AAA GGA

ACC TAC TTG TAC AAT GAC TGT CCA GGC CCG GGG CAG GAT

ACG GAC TGC AGG GAG TGT GAG AGC GGC TCC TTC ACC GCT

TCA GAA AAC CAC CTC AGA CAC TGC CTC AGC TGC TCC AAA

TGC CGA AAG GAA ATG GGT CAG GTG GAG ATC TCT TCT TGC

ACA GTG GAC CGG GAC ACC GTG TGT GGC TGC AGG AAG AAC

CAG TAC CGG CAT TAT TGG AGT GAA AAC CTT TTC CAG TGC

TTC AAT TGC AGC CTC TGC CTC AAT GGG ACC GTG CAC CTC

TCC TGC CAG GAG AAA CAG AAC ACC GTG TGC ACC TGC CAT

GCA GGT TTC TTT CTA AGA GAA AAC GAG TGT GTC TCC TGT

AGT AAC TGT AAG AAA AGC CTG GAG TGC ACG AAG TTG TGC

CTA CCC CAG ATT GAG AAT

D) DNA comprising the sequence:

ATG GAT AGT GTG TGT CCC CAA GGA AAA TAT ATC CAC CCT

CAA AAT AAT TCG ATT TGC TGT ACC AAG TGC CAC AAA GGA

ACC TAC TTG TAC AAT GAC TGT CCA GGC CCG GGG CAG GAT

ACG GAC TGC AGG GAG TGT GAG AGC GGC TCC TTC ACC GCT

TCA GAA AAC CAC CTC AGA CAC TGC CTC AGC TGC TCC AAA

TGC CGA AAG GAA ATG GGT CAG GTG GAG ATC TCT TCT TGC

ACA GTG GAC CGG GAC ACC GTG TGT GGC TGC AGG AAG AAC

CAG TAC CGG CAT TAT TGG AGT GAA AAC CTT TTC CAG TGC

TTC AAT TGC AGC CTC TGC CTC AAT GGG ACC GTG CAC CTC

TCC TGC CAG GAG AAA CAG AAC ACC GTG TGC ACC TGC CAT

GCA GGT TTC TTT CTA AGA GAA AAC GAG TGT GTC TCC TGT

AGT AAC TGT AAG AAA AGC CTG GAG TGC ACG AAG TTG TGC

CTA CCC CAG ATT GAG AAT GTT AAG GGC ACT GAG GAC TCA

GGC ACC ACA

E) DNA comprising the sequence:

ATG GGC CTC TCC ACC GTG CCT GAC CTG CTG CTG CCA

CTG GTG CTC CTG GAG CTG TTG GTG GGA ATA TAC CCC

TCA GGG GTT ATT GGA CTG GTC CCT CAC CTA GGG GAC

AGG GAG AAG AGA GAT AGT GTG TGT CCC CAA GGA AAA

TAT ATC CAC CCT CAA AAT AAT TCG ATT TGC TGT ACC

AAG TGC CAC AAA GGA ACC TAC TTG TAC AAT GAC TGT

CCA GGC CCG GGG CAG GAT ACG GAC TGC AGG GAG TGT

GAG AGC GGC TCC TTC ACC GCT TCA GAA AAC CAC CTC

AGA CAC TGC CTC AGC TGC TCC AAA TGC CGA AAG GAA

ATG GGT CAG GTG GAG ATC TCT TCT TGC ACA GTG GAC

CGG GAC ACC GTG TGT GGC TGC AGG AAG AAC CAG TAC

CGG CAT TAT TGG AGT GAA AAC CTT TTC CAG TGC TTC

AAT TGC AGC CTC TGC CTC AAT GGG ACC GTG CAC CTC

TCC TGC CAG GAG AAA CAG AAC ACC GTG TGC ACC TGC

CAT GCA GGT TTC TTT CTA AGA GAA AAC GAG TGT GTC

TCC TGT AGT AAC TGT AAG AAA AGC CTG GAG TGC ACG

AAG TTG TGC CTA CCC CAG ATT GAG AAT

F) DNA comprising the sequence:

ATG GGC CTC TCC ACC GTG CCT GAC CTG CTG CTG CCA

CTG GTG CTC CTG GAG CTG TTG GTG GGA ATA TAC CCC

TCA GGG GTT ATT GGA CTG GTC CCT CAC CTA GGG GAC

AGG GAG AAG AGA GAT AGT GTG TGT CCC CAA GGA AAA

TAT ATC CAC CCT CAA AAT AAT TCG ATT TGC TGT ACC

-continued

AAG TGC CAC AAA GGA ACC TAC TTG TAC AAT GAC TGT
CCA GGC CCG GGG CAG GAT ACG GAC TGC AGG GAG TGT
GAG AGC GGC TCC TTC ACC GCT TCA GAA AAC CAC CTC
AGA CAC TGC CTC AGC TGC TCC AAA TGC GAA AAG GAA
ATG GGT CAG GTG GAG ATC TCT TCT TGC ACA GTG GAC
CGG GAC ACC GTG TGT GGC TGC AGG AAG AAC CAG TAC
CGG CAT TAT TGG AGT GAA AAC CTT TTC CAG TGC TTC
AAT TGC AGC CTC TGC CTC AAT GGG ACC GTG CAC CTC
TCC TGC CAG GAG AAA CAG AAC ACC GTG TGC ACC TGC
CAT GCA GGT TTC TTT CTA AGA GAA AAC GAG TGT GTC
TCC TGT AGT AAC TGT AAG AAA AGC CTG GAG TGC ACG
AAG TTG TGC CTA CCC CAG ATT GAG AAT GTT AAG GGC
ACT GAG GAC TCA GGC ACC ACA

G) DNA comprising the sequence:

ATG GGC CTC TCC ACC GTG CCT GAC CTG CTG CTG CCA
CTG GTG CTC CTG GAG CTG TTG GTG GGA ATA TAC CCC
TCA GGG GTT ATT GGA GAT AGT GTG TGT CCC CAA GGA
AAA TAT ATC CAC CCT CAA AAT AAT TCG ATT TGC TGT
ACC AAG TGC CAC AAA GGA ACC TAC TTG TAC AAT GAC
TGT CCA GGC CCG GGG CAG GAT ACG GAC TGC AGG GAG
TGT GAG AGC GGC TCC TTC ACC GCT TCA GAA AAC CAC
CTC AGA CAC TGC CTC AGC TGC TCC AAA TGC GAA AAG
GAA ATG GGT CAG GTG GAG ATC TCT TCT TGC ACA GTG
GAC CGG GAC ACC GTG TGT GGC TGC AGG AAG AAC CAG
TAC CGG CAT TAT TGG AGT GAA AAC CTT TTC CAG TGC
TTC AAT TGC AGC CTC TGC CTC AAT GGG ACC GTG CAC
CTC TCC TGC CAG GAG AAA CAG AAC ACC GTG TGC ACC
TGC CAT GCA GGT TTC TTT CTA AGA GAA AAC GAG TGT
GTC TCC TGT AGT AAC TGT AAG AAA AGC CTG GAG TGC
ACG AAG TTG TGC CTA CCC CAG ATT GAG AAT

H) DNA comprising the sequence:

ATG GGC CTC TCC ACC GTG CCT GAC CTG CTG CTG CCA
CTG GTG CTC CTG GAG CTG TTG GTG GGA ATA TAC CCC
TCA GGG GTT ATT GGA GAT AGT GTG TGT CCC CAA GGA
AAA TAT ATC CAC CCT CAA AAT AAT TCG ATT TGC TGT
ACC AAG TGC CAC AAA GGA ACC TAC TTG TAC AAT GAC
TGT CCA GGC CCG GGG CAG GAT ACG GAC TGC AGG GAG
TGT GAG AGC GGC TCC TTC ACC GCT TCA GAA AAC CAC

-continued

CTC AGA CAC TGC CTC AGC TGC TCC AAA TGC GAA AAG
GAA ATG GGT CAG GTG GAG ATC TCT TCT TGC ACA GTG
GAC CGG GAC ACC GTG TGT GGC TGC AGG AAG AAC CAG
TAC CGG CAT TAT TGG AGT GAA AAC CTT TTC CAG TGC
TTC AAT TGC AGC CTC TGC CTC AAT GGG ACC GTG CAC
CTC TCC TGC CAG GAG AAA CAG AAC ACC GTG TGC ACC
TGC CAT GCA GGT TTC TTT CTA AGA GAA AAC GAG TGT
GTC TCC TGT AGT AAC TGT AAG AAA AGC CTG GAG TGC
ACG AAG TTG TGC CTA CCC CAG ATT GAG AAT GTT AAG
GGC ACT GAG GAC TCA GGC ACC ACA and I) DNA comprising the sequence:

ATG GGC CTC TCC ACC GTG CCT GAC CTG CTG CTG CCA CTG
GTG CTC CTG GAG CTG TTG GTG GGA ATA TAC CCC TCA GGG
GTT ATT GGA CTG GTC CCT CAC CTA GGG GAC AGG GAG AAG
AGA GAT AGT GTG TGT CCC CAA GGA AAA TAT ATC CAC CCT
CAA AAT AAT TCG ATT TGC TGT ACC AAG TGC CAC AAA GGA
ACC TAC TTG TAC AAT GAC TGT CCA GGC CCG GGG CAG GAT
ACG GAC TGC AGG GAG TGT GAG AGC GGC TCC TTC ACC GCT
TCA GAA AAC CAC CTC AGA CAC TGC CTC AGC TGC TCC AAA
TGC CGA AAG GAA ATG GGT CAG GTG GAG ATC TCT TCT TGC
ACA GTG GAC CGG GAC ACC GTG TGT GGC TGC AGG AAG AAC
CAG TAC CGG CAT TAT TGG AGT GAA AAC CTT TTC CAG TGC
TTC AAT TGC AGC CTC TGC CTC AAT GGG ACC GTG CAC CTC
TCC TGC CAG GAG AAA CAG AAC ACC GTG TGC ACC TGC CAT
GCA GGT TTC TTT CTA AGA GAA AAC GAG TGT GTC TCC TGT
AGT AAC TGT AAG AAA AGC CTG GAG TGC ACG AAG TTG TGC
CTA CCC CAG ATT GAG AAT GTT AAG GGC ACT GAG GAC TCA
GGC ACC ACA GTG CTG TTG CCC CTG GTC ATT TTC TTT GGT
CTT TGC CTT TTA TCC CTC CTC TTC ATT GGT TTA ATG TAT
CGC TAC CAA CGG TGG AAG TCC AAG CTC TAC TCC ATT GTT
TGT GGG AAA TCG ACA CCT GAA AAA GAG GGG GAG CTT GAA
GGA ACT ACT ACT AAG CCC CTG GCC CCA AAC CCA AGC TTC
AGT CCC ACT CCA GGC TTC ACC CCC ACC TGG GGC TTC AGT
CCC GTG CCC AGT TCC ACC TTC ACC TCC AGC TCC ACC TAT
ACC CCC GGT GAC TGT CCC AAC TTT GCG GCT CCC CGC AGA
GAG GTG GCA CCA CCC TAT CAG GGG CTG ACC CCC ATC TTT
GCG ACA GCC CTC GCC TCC GAC CCC ATC CCC AAC CCC CTT
CAG AAG TGG GAG GAC AGC GCC CAC AAG CCA CAG AGC CTA

-continued

```
GAC ACT GAT GAC CCC GCG ACG CTG TAC GCC GTG GTG GAG
AAC GTG CCC CCG TTG CGC TGG AAG GAA TTC GTG CGG CGC
CTA GGG CTG AGC GAC CAC GAG ATC GAT CGG CTG GAG CTG
CAG AAC GGG CGC TGC CTG CGC GAG GCG CAA TAC AGC ATG
CTG GCG ACC TGG AGG CGG CGC ACG CCG CGG CGC GAG GCC
ACG CTG GAG CTG CTG GGA CGC GTG CTC CGC GAC ATG GAC
CTG CTG GGC TGC CTG GAG GAC ATC GAG GAG GCG CTT TGC
GGC CCC GCC GCC CTC CCG CCC GCG CCC AGT CTT CTC AGA
```

J) a DNA sequence of A, B, C, D, E, F, G, H or I encoding at least one conservative amino acid substitution;

K) a DNA sequence of A, B, C, D, E, F, G, H or I encoding at least one amino acid substitution at a glycosylation site;

L) a DNA sequence of A, B, C, D, E, F, G, H or I encoding at least one amino acid substitution at a proteolytic cleavage site; and M) a DNA sequence of A, B, C, D, E, F, G, H or I encoding at least one amino acid substitution at a cysteine residue.

5. A recombinant host cell containing a DNA molecule comprising a DNA coding for a polypeptide having the ability to bind TNF selected from the group consisting of:

A) a polypeptide comprising the amino acid sequence:

```
met gly leu ser thr val pro asp leu leu leu pro leu
val leu leu glu leu leu val gly ile tyr pro ser gly
val ile gly leu val pro his leu gly asp arg glu lys
arg asp ser val cys pro gln gly lys tyr ile his pro
gln asn asn ser ile cys cys thr lys cys his lys gly
thr tyr leu tyr asn asp cys pro gly pro gly gln asp
thr asp cys arg glu cys glu ser gly ser phe thr ala
ser glu asn his leu arg his cys leu ser cys ser lys
cys arg lys glu met gly gln val glu ile ser ser cys
thr val asp arg asp thr val cys gly cys arg lys asn
gln tyr arg his tyr trp ser glu asn leu phe gln cys
phe asn cys ser leu cys leu asn gly thr val his leu
ser cys gln glu lys gln asn thr val cys thr cys his
ala gly phe phe leu arg glu asn glu cys val ser cys
ser asn cys lys lys ser leu glu cys thr lys leu cys
leu pro gln ile glu asn val lys gly thr glu asp ser
gly thr thr val leu leu pro leu val ile phe phe gly
leu cys leu leu ser leu leu phe ile gly leu met tyr
arg tyr gln arg trp lys ser lys leu tyr ser ile val
cys gly lys ser thr pro glu lys glu gly glu leu glu
gly thr thr thr lys pro leu ala pro asn pro ser phe
ser pro thr pro gly phe thr pro thr leu gly phe ser
pro val pro ser ser thr phe thr ser ser ser thr tyr
thr pro gly asp cys pro asn phe ala ala pro arg arg
glu val ala pro pro tyr gln gly ala asp pro ile leu
ala thr ala leu ala ser asp pro ile pro asn pro leu
gln lys trp glu asp ser ala his lys pro gln ser leu
asp thr asp asp pro ala thr leu tyr ala val val glu
asn val pro pro leu arg trp lys glu phe val arg arg
leu gly leu ser asp his glu ile asp arg leu glu leu
gln asn gly arg cys leu arg glu ala gln tyr ser met
leu ala thr trp arg arg arg thr pro arg arg glu ala
thr leu glu leu leu gly arg val leu arg asp met asp
leu leu gly cys leu glu asp ile glu glu ala leu cys
gly pro ala ala leu pro pro ala pro ser leu leu
arg;
```

B) a polypeptide comprising the amino acid sequence:

```
asp ser val cys pro gln gly lys tyr ile his pro gln
asn asn ser ile cys cys thr lys cys his lys gly thr
tyr leu tyr asn asp cys pro gly pro gly gln asp thr
asp cys arg glu cys glu ser gly ser phe thr ala ser
glu asn his leu arg his cys leu ser cys ser lys cys
arg lys glu met gly gln val glu ile ser ser cys thr
val asp arg asp thr val cys gly cys arg lys asn gln
tyr arg his tyr trp ser glu asn leu phe gln cys phe
asn cys ser leu cys leu asn gly thr val his leu ser
cys gln glu lys gln asn thr val cys thr cys his ala
gly phe phe leu arg glu asn glu cys val ser cys ser
asn cys lys lys ser leu glu cys thr lys leu cys leu
pro gln ile glu asn.
```

C) a polypeptide comprising the amino acid sequence of A, B, C or D with at least one conservative amino acid substitution;

D) a polypeptide comprising the amino acid sequence of A, B, C or D with at least one amino acid substitution at a glycosylation site;

E) a polypeptide comprising the amino acid sequence of A, B, C or D with at least one amino acid substitution at a proteolytic cleavage site; and F) a polypeptide comprising the amino acid sequence of A, B, C or D with at least one amino acid substitution at a cysteine residue.

6. A recombinant host cell according to claim 5, which is a mammalian cell.

7. A process for preparing a recombinant host cell containing polypeptide having TNF inhibitory activity comprising producing the polypeptide in a recombinant host cell according to claim 5, under suitable conditions to express the DNA molecule contained therein to produce the polypeptide.

8. A process according to claim 7, wherein said host cell is a prokaryotic cell.

9. A process according to claim 8, wherein said host cell is *E. Coli.*

10. A process according to claim 7, wherein said host cell is a eukaryotic cell.

11. A process according to claim 10, wherein said host cell is a mammalian cell.

12. A process according to claim 11, wherein said host cell is a Chinese Hamster Ovary cell.

13. A process according to claim 11, wherein said host cell is a COS cell.

14. A process according to claim 7, wherein the DNA molecule comprises promoter DNA, other than the promoter DNA for the native polypeptide having TNF inhibitory activity, operatively linked to the nucleic acid encoding the native polypeptide having TNF inhibitory activity.

15. A process according to claim 7, wherein the host cell is grown under suitable nutrient conditions to amplify the nucleic acid sequence.

16. An isolated DNA molecule wherein said DNA comprises a sequence selected from the group consisting of:

A)

$R^2$ GAT AGT GTG TGT CCC CAA GGA AAA TAT ATC CAC CCT

CAA AAT AAT TCG ATT TGC TGT ACC AAG TGC CAC AAA GGA

ACC TAC TTG TAC AAT GAC TGT CCA GGC CCG GGG CAG GAT

ACG GAC TGC AGG GAG TGT GAG AGC GGC TCC TTC ACC GCT

TCA GAA AAC CAC CTC AGA CAC TGC CTC AGC TGC TCC AAA

TGC CGA AAG GAA ATG GGT CAG GTG GAG ATC TCT TCT TGC

ACA GTG GAC CGG GAC ACC GTG TGT GGC TGC AGG AAG AAC

CAG TAC CGG CAT TAT TGG AGT GAA AAC CTT TTC CAG TGC

TTC AAT TGC AGC CTC TGC CTC AAT GGG ACC GTG CAC CTC

TCC TGC CAG GAG AAA CAG AAC ACC GTG TGC ACC TGC CAT

GCA GGT TTC TTT CTA AGA GAA AAC GAG TGT GTC TCC TGT

AGT AAC TGT AAG AAA AGC CTG GAG TGC ACG AAG TTG TGC

CTA CCC CAG ATT GAG AAT wherein $R^2$ is absent or is a DNA comprising a sequence coding for a polypeptide which can be cleaved in vivo;

B) a fragment or degenerate variant of the polypeptide of A;

C) a polypeptide comprising the amino acid sequence of A or B with at least one conservative amino acid substitution;

D) a polypeptide comprising the amino acid sequence of A or B with at least one amino acid substitution at a glycosylation site;

E) a polypeptide comprising the amino acid sequence of A or B with at least one amino acid substitution at a proteolytic cleavage site; and F) a polypeptide comprising the amino acid sequence of A or B with at least one amino acid substitution at a cysteine residue.

17. An isolated DNA molecule according to claim 16, wherein $R^2$ is a DNA comprising a sequence which codes entirely or partly for a signal sequence.

18. An isolated DNA molecule according to claim 16, wherein $R^2$ is a DNA comprising the sequence CTG GTC CCT CAC CTA GGG GAC AGG GAG AAG AGA or a fragment thereof.

19. An isolated DNA molecule according to claim 17, wherein $R^2$ is a DNA comprising the sequence $R^3$ CTG GTC CCT CAC CTA GGG GAC AGG GAG AAG AGA, wherein $R^3$ is a DNA molecule coding for a signal peptide, or a fragment thereof.

20. An isolated DNA molecule according to claim 19, wherein $R^3$ is a DNA comprising the sequence:

ATG GGC CTC TCC ACC GTG CCT GAC CTG CTG CTG CCA CTG GTG CTC CTG GAG CTG TTG GTG GGA ATA TAC CCC TCA GGG GTT ATT GGA, or a fragment thereof.

21. A nucleic acid which hybridizes with DNA complementary to the DNA defined in claim 16 under conditions of low stringency such that the nucleic acid is useful as a hybridization probe to detect DNA encoding the polypeptide of A or B.

22. A recombinant DNA molecule, which is replicable in procaryotic or eukaryotic host organisms, wherein said DNA molecule contains expression control sequences functionally linked to the DNA sequence defined in claim 16, or a degenerate variant or a fragment thereof.

23. An isolated DNA molecule coding for a polypeptide selected from the group consisting of:

A) a polypeptide comprising the amino acid sequence:

met gly leu ser thr val pro asp leu leu leu pro leu val leu leu glu leu leu val gly ile tyr pro ser gly val ile gly leu val pro his leu gly asp arg glu lys arg asp ser val cys pro gln gly lys tyr ile his pro gln asn asn ser ile cys cys thr lys cys his lys gly thr tyr leu tyr asn asp cys pro gly pro gly gln asp thr asp cys arg glu cys glu ser gly ser phe thr ala ser glu asn his leu arg his cys leu ser cys ser lys cys arg lys glu met gly gln val glu ile ser ser cys thr val asp arg asp thr val cys gly cys arg lys asn gln tyr arg his tyr trp ser glu asn leu phe gln cys phe asn cys ser leu cys leu asn gly thr val his leu ser cys gln glu lys gln asn thr val cys thr cys his ala gly phe phe leu arg glu asn glu cys val ser cys ser asn cys lys lys ser leu glu cys thr lys leu cys leu pro gln ile glu asn val lys gly thr glu asp ser gly thr thr val leu leu pro leu val ile phe phe gly leu cys leu leu ser leu leu phe ile gly leu met tyr arg tyr gln arg trp lys -continued

```
ser lys leu tyr ser ile val cys gly lys ser thr
pro glu lys glu gly glu leu glu gly thr thr thr
lys pro leu ala pro asn pro ser phe ser pro thr
pro gly phe thr pro thr leu gly phe ser pro val
pro ser ser thr phe thr ser ser thr tyr thr
pro gly asp cys pro asn phe ala ala pro arg arg
glu val ala pro pro tyr gln gly ala asp pro ile
leu ala thr ala leu ala ser asp pro ile pro asn
pro leu gln lys trp glu asp ser ala his lys pro
gln ser leu asp thr asp asp pro ala thr leu tyr
ala val val glu asn val pro pro leu arg trp lys
glu phe val arg arg leu gly leu ser asp his glu
ile asp arg leu glu leu gln asn gly arg cys leu
arg glu ala gln tyr ser met leu ala thr trp arg
arg arg thr pro arg arg glu ala thr leu glu leu
leu gly arg val leu arg asp met asp leu leu gly
cys leu glu asp ile glu glu ala leu cys gly pro
ala ala leu pro pro ala pro ser leu leu arg;
```

B) a polypeptide comprising the amino acid sequence:

```
asp ser val cys pro gln gly lys tyr ile his pro
gln asn asn ser ile cys cys thr lys cys his lys
gly thr tyr leu tyr asn asp cys pro gly pro gly
gln asp thr asp cys arg glu cys glu ser gly ser
phe thr ala ser glu asn his leu arg his cys leu
ser cys ser lys cys arg lys glu met gly gln val
glu ile ser ser cys thr val asp arg asp thr val
cys gly cys arg lys asn gln tyr arg his tyr trp
ser glu asn leu phe gln cys phe asn cys ser leu
cys leu asn gly thr val his leu ser cys gln glu
lys gln asn thr val cys thr cys his ala gly phe
phe leu arg glu asn glu cys val ser cys ser asn
cys lys lys ser leu glu cys thr lys leu cys leu
pro gln ile glu asn;
```

C) a fragment of A or B complementary to the DNA encoding the polypeptide of A or B and is useful as a hybridization probe to detect the DNA encoding the polypeptide of A or B;

D) a polypeptide comprising the amino acid sequence of A, B or C with at least one conservative amino acid substitution;

E) a polypeptide comprising the amino acid sequence of A, B or C with at least one amino acid substitution at a glycosylation site;

F) a polypeptide comprising the amino acid sequence of A, B or C with at least one amino acid substitution at a proteolytic cleavage site; and G) a polypeptide comprising the amino acid sequence of A, B or C with at least one amino acid substitution at a cysteine residue.

24. A DNA according to claim 23, wherein said polypeptide is selected from the group consisting of:

A) a polypeptide comprising the amino acid sequence:

```
R² asp ser val cys pro gln gly lys tyr ile his
pro gln asn asn ser ile cys cys thr lys cys his
lys gly thr tyr leu tyr asn asp cys pro gly pro
gly gln asp thr asp cys arg glu cys glu ser gly
ser phe thr ala ser glu asn his leu arg his cys
leu ser cys ser lys cys arg lys glu met gly gln
val glu ile ser ser cys thr val asp arg asp thr
val cys gly cys arg lys asn gln tyr arg his tyr
trp ser glu asn leu phe gln cys phe asn cys ser
leu cys leu asn gly thr val his leu ser cys gln
glu lys gln asn thr val cys thr cys his ala gly
phe phe leu arg glu asn glu cys val ser cys ser
asn cys lys lys ser leu glu cys thr lys leu cys
leu pro gln ile glu asn;
``` wherein $R^2$ is absent or is a polypeptide which can be cleaved in vivo;

B) a fragment or functional derivative of the polypeptide of A which binds TNF;

C) a polypeptide comprising the amino acid sequence of A or B with at least one conservative amino acid substitution;

D) a polypeptide comprising the amino acid sequence of A or B with at least one amino acid substitution at a glycosylation site;

E) a polypeptide comprising the amino acid sequence of A or B with at least one amino acid substitution at a proteolytic cleavage site; and F) a polypeptide comprising the amino acid sequence of A or B with at least one amino acid substitution at a cysteine residue.

25. A DNA according to claim 24, wherein said polypeptide includes at least one additional amino acid at the amino-terminus, at the carboxyl-terminus, or at both the amino-terminus and at the carboxyl-terminus.

26. A DNA according to claim 25, wherein said polypeptide includes at least one additional amino acid at the amino-terminus and at the carboxyl-terminus.

27. A DNA according to claim 25, wherein said polypeptide includes at least one additional amino acid at the amino-terminus.

28. A DNA according to claim 27, wherein said polypeptide includes a methionine at the amino-terminus.

29. A DNA according to claim 28, wherein said polypeptide includes at least one additional amino acid at the carboxyl-terminus.

30. A nucleic acid that hybridizes to a DNA complementary to the DNA defined in claim 24 under conditions of low stringency such that the nucleic acid is useful as a hybridization probe to detect DNA encoding the polypeptide of A or B.

31. A vector comprising a DNA sequence of claims 1, 2, 3, 4, 16 or 23, coding for a TNF binding protein which binds TNF.

32. A vector comprising a DNA sequence defined in claim 24.

33. A vector according to claim 32, which is replicable in a prokaryotic and/or a eukaryotic host cell.

34. A vector according to claim 33, which is replicable in a prokaryotic cell.

35. A vector according to claim 34, wherein said DNA sequence encodes ATG at the amino terminus of the peptide.

36. A vector according to claim 34, which is replicable in *Escherichia coli.*

37. A vector according to claim 33, which is replicable in a eukaryotic cell.

38. A vector according to claim 37, which is replicable in a mammalian cell.

39. A vector according to claim 38, which is replicable in a Chinese Hamster Ovary cell.

40. A vector according to claim 38, which is replicable in a COS cell.

41. A host cell containing a recombinant DNA molecule comprising a DNA sequence defined in claim 25.

42. A host cell according to claim 41, which is a prokaryotic cell.

43. A host cell according to claim 42, which is *Escherichia coli.*

44. A host cell according to claim 41, which is a eukaryotic cell.

45. A host cell according to claim 44, which is a mammalian cell.

46. A host cell according to claim 45, which is a Chinese Hamster Ovary cell.

47. A host cell according to claim 45, which is a COS cell.

48. A recombinant host cell according to claim 5, wherein the DNA molecule comprises promoter DNA, other than the promoter DNA for the native polypeptide having the ability to bind TNF, operatively linked to the DNA sequence encoding the polypeptide.

49. A process for preparing a polypeptide having the ability to bind TNF comprising producing the polypeptide in a recombinant host cell according to claim 48 under suitable conditions to express the DNA molecule contained therein to produce the polypeptide, and recovering the polypeptide.

50. A process for preparing a polypeptide having the ability to bind TNF comprising producing the polypeptide in a recombinant host cell according to claim 48 under suitable conditions to express the DNA molecule contained therein to produce the polypeptide, and recovering the polypeptide.

51. A process according to claim 50, further comprising combining the recovered recombinant polypeptide with a pharmaceutically acceptable carrier to form a pharmaceutical composition.

52. A process according to claim 51, further comprising chemically derivatizing the harvested polypeptide.

53. A process according to claim 52, further comprising combining the chemically derivatized recombinant polypeptide with a pharmaceutically acceptable carrier to form a pharmaceutical composition.

54. A process according to claim 53, wherein said recombinant DNA molecule is contained in an expression vector.

55. A process for preparing a recombinant TNF receptor protein, comprising cultivating the host cell of claim 42 and isolating the expressed protein.

56. An isolated DNA molecule according to one of claims 1, 2, 3, 4, 16, 23 or 24 wherein said polypeptide includes at least one additional amino acid at the amino-terminus, at the carboxyl-terminus, or at both the amino-terminus and at the carboxyl-terminus.

57. An isolated DNA molecule according to claim 56, wherein said polypeptide includes at least one additional amino acid at the amino-terminus and at the carboxyl-terminus.

58. An isolated DNA molecule according to claim 56, wherein said polypeptide includes at least one additional amino acid at the amino-terminus.

59. An isolated DNA molecule according to claim 58, wherein said polypeptide includes a methionine at the amino-terminus.

60. An isolated DNA molecule according to claim 56, wherein said polypeptide includes at least one additional amino acid at the carboxyl-terminus.

61. An isolated DNA molecule according to claim 1, 2, 3, 4, 16, 23 or 24, wherein said polypeptide includes a methionine at the amino-terminus and said amino acid substitution is at a glycosylation site.

62. An isolated DNA molecule according to claim 1, 2, 3, 4, 16, 23 or 24, wherein said polypeptide includes an amino acid substitution is at a glycosylation site.

63. A recombinant DNA molecule, which is replicable in prokaryotic or eukaryotic host organisms, wherein said DNA molecule contains expression control sequences functionally linked to the DNA sequence defined in claim 16, or a degenerate variant thereof or a fragment thereof.

* * * * *

UNITED STATES PATENT AND TRADEMARK OFFICE
CERTIFICATE OF CORRECTION

PATENT NO. : 6,294,352 B1
DATED : September 25, 2001
INVENTOR(S) : Rudolf Hauptmann et al.

It is certified that error appears in the above-identified patent and that said Letters Patent is hereby corrected as shown below:

Column 8,
Line 51, delete "$131_I$" and insert therefor -- $^{131}I$ --.

Column 31,
Line 49, delete "Glu-Cys-Gl u-Ser-Gly-Ser-Phe-Thr-Ala-Ser-(Glu/Cys)- " and insert therefor -- Glu-Cys-Glu-Ser-Gly-Ser-Phe-Thr-Ala-Ser-(Glu/Cys)- --.
Line 55, delete "-Phe-Thr-Ala-Ser-Glu-Asn-ASn-Lys" and insert therefor -- -Phe-Thr-Ala-Ser-Glu-Asn-Asn-Lys --

Column 32,
Line 35, delete "MAT" and insert therefor -- AAT --.

Column 38,
Line 3, delete "HB11" and insert therefor -- HB101 --.
Line 37, delete "GGCAMGGGCAGCAGCCGG-3')" and insert therefor
-- GGCAAGGGCAGCAGCCGG-3') --.

Column 39,
Line 12, delete "CTAGAGAMTTCGCGGCCGCTCGGGTACCGGA"
and insert therefor -- CTAGAGAATTCGCGGCCGCTCGAGGTACCGGA --.
Line 38, delete "oiigonucleotide" and insert therefor -- oligonucleotide --.

Column 40,
Lines 37-38, delete
"5'-GGGAATTCCTTATCMTTCTCMTCTGGGGTAGGCACMCTTC-3 '" and insert therefor -- 5'-GGGAATTCCTTATCAATTCTCAATCTGGGGTAGGCACAACTTC-3' --
Line 41, delete "72° C. ani" and insert therefor -- 72° C and --.

Column 41,
Lines 1-4, delete "(5'-CACAGTCGACTTACATTTGCTTCTGACACA
ACTGTGTTCACTAGCMCCTCAAACAGACACCATGGGCCTCTCCACCGTG-3')"
and insert therefor --
(5'-CACAGTCGACTTACATTTGCTTCTGACACAACTGTGTTCACTAGC
AACCTCAAACAGACACCATGGGCCTCTCCACCGTGC-3') --

UNITED STATES PATENT AND TRADEMARK OFFICE
CERTIFICATE OF CORRECTION

PATENT NO.   : 6,294,352 B1
DATED        : September 25, 2002
INVENTOR(S)  : Rudolf Hauptmann et al.

It is certified that error appears in the above-identified patent and that said Letters Patent is hereby corrected as shown below:

<u>Column 45,</u>
Line 13, delete "250 □g/mi" and insert therefor -- 250 □g/ml --.

Signed and Sealed this

Ninth Day of September, 2003

JAMES E. ROGAN
*Director of the United States Patent and Trademark Office*